United States Patent
Kohno et al.

(10) Patent No.: US 9,216,172 B2
(45) Date of Patent: Dec. 22, 2015

(54) METHOD FOR DETERMINING EFFECTIVENESS OF CANCER TREATMENT BY ASSESSING THE PRESENCE OF A KIF5B-RET CHIMERIC GENE

(75) Inventors: Takashi Kohno, Tokyo (JP); Koji Tsuta, Tokyo (JP)

(73) Assignees: National Cancer Center, Toyko (JP); LSIP, LLC, Tokyo (JP)

( * ) Notice: Subject to any disclaimer, the term of this patent is extended or adjusted under 35 U.S.C. 154(b) by 0 days.

(21) Appl. No.: 14/236,900

(22) PCT Filed: Aug. 3, 2012

(86) PCT No.: PCT/JP2012/069799
§ 371 (c)(1),
(2), (4) Date: Apr. 8, 2014

(87) PCT Pub. No.: WO2013/018882
PCT Pub. Date: Feb. 7, 2013

(65) Prior Publication Data
US 2014/0221404 A1    Aug. 7, 2014

(30) Foreign Application Priority Data

Aug. 4, 2011   (JP) ................................ 2011/171256

(51) Int. Cl.
| | | |
|---|---|---|
| *A61P 35/00* | (2006.01) | |
| *A61K 31/4412* | (2006.01) | |
| *C07K 14/82* | (2006.01) | |
| *G01N 33/574* | (2006.01) | |
| *C12Q 1/68* | (2006.01) | |
| *A61K 31/517* | (2006.01) | |
| *C12N 9/12* | (2006.01) | |
| *C12N 9/14* | (2006.01) | |
| *A61K 31/44* | (2006.01) | |
| *C07K 14/71* | (2006.01) | |
| *A61K 38/00* | (2006.01) | |

(52) U.S. Cl.
CPC ............ *A61K 31/4412* (2013.01); *A61K 31/44* (2013.01); *A61K 31/517* (2013.01); *C07K 14/71* (2013.01); *C07K 14/82* (2013.01); *C12N 9/1205* (2013.01); *C12N 9/14* (2013.01); *C12Q 1/6886* (2013.01); *G01N 33/57407* (2013.01); *G01N 33/57423* (2013.01); *A61K 38/00* (2013.01); *C07K 2319/00* (2013.01); *C12Q 2600/106* (2013.01); *C12Q 2600/156* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2008/0044824 A1* | 2/2008 | Giordano et al. ................. 435/6 |
| 2009/0136502 A1 | 5/2009 | Arai et al. | |
| 2010/0143459 A1 | 6/2010 | Liepold et al. | |
| 2013/0137111 A1* | 5/2013 | Shindo et al. ................ 435/6.12 |

FOREIGN PATENT DOCUMENTS

| | | |
|---|---|---|
| EP | 1920767 A1 | 5/2008 |
| EP | 1941909 A1 | 7/2008 |
| JP | 2010-509289 A | 3/2010 |
| WO | WO-2007/049624 A1 | 5/2007 |
| WO | WO-2008/055966 A1 | 5/2008 |
| WO | WO-2010/000012 A1 | 1/2010 |
| WO | PCT/JP2011/066661 * | 2/2012 ............... C12Q 1/68 |
| WO | WO-2012/014795 A1 | 2/2012 |
| WO | WO-2012/053606 A1 | 4/2012 |

OTHER PUBLICATIONS

Yokota et al. KIF5B/RET fusion gene in surgically-treated adenocarcinoma of the lung. Oncology reports, 28, 1187-1192, 2012.*

Takeuchi et al., KIF5B-ALK, a Novel Fusion Oncokinase Identified by an Immunohistochemistry-based Diagnostic System for ALK-positive Lung Cancer, Clin. Cancer Res., 15, 3143-3149, 2009.*

Ju et al., A transforming KIF5B and RET gene fusion in lung adenocarcinoma revealed from whole-genome and transcriptome sequencing. Genome Res., 22, 436-445, 2012.*

Lipson et al. Identification of new ALK and RET gene fusions from colorectal and lung cancer biopsies. Nat. Med. 18, 382-384, 2012.*

(Continued)

*Primary Examiner* — Elly-Gerald Stoica

(74) *Attorney, Agent, or Firm* — Mintz Levin Cohn Ferris Glovsky and Popeo, P.C.; David G. Conlin; Joohee Lee

(57) ABSTRACT

In order to identify a gene that can serve as an indicator for predicting the effectiveness of a drug treatment of cancer and to provide a novel method for predicting the effectiveness of a drug treatment targeting said gene, lung adenocarcinomas were subjected to whole-transcriptome sequencing. As a result, in-frame fusion transcripts between the KIF5B gene and the RET gene were identified. The KIF5B-RET gene fusions were detected in 6 out of 319 (2%) LADC specimens from Japanese individuals and 1 out of 80 (1%) LADC specimens from U.S.A. individuals. None of the seven subjects revealed known activating mutations such as EGFR, KRAS or ALK oncogenes; thus, said gene fusions were found to be responsible mutations (driver mutations) for oncogenesis. Since said gene fusions are considered to induce constitutive activation of RET tyrosine kinase protein, it was found that treatments with RET tyrosine kinase inhibitors are effective in patients with detection of said gene fusions.

1 Claim, 17 Drawing Sheets

(56) References Cited

OTHER PUBLICATIONS

De Groot et al., RET as a Diagnostic and Therapeutic Target in Sporadic and Hereditary Endocrine Tumors. Endocrine Rev., 27, 535-560, 2006.*

Lips et al., Clinical screening as compared with DNA analysis in families with multiple endocrine neoplasia type 2A. N. Engl. J. Med., 331, 828-835, 1994.*

English translation of the ISR of PCT/JP2012/069799, issued Oct. 9, 2012.

Herbst, R. S., et al., "Molecular Origins of Cancer: Lung Cancer". NEJM, 2008, vol. 359, p. 1367-1380.

Janku, F., et al., "Targeted therapy in non-small-cell lung cancer-is it becoming a reality?" *Nat Rev Clin Oncol*, 2010, vol. 7, p. 401-414.

Lovly, C. M., et al., "One size does not fit all." *Nat Rev Clin Oncol*, 2011, vol. 8, p. 68-70.

Paez, J. G., et al., "EGFR Mutaions in Lung Cancer: Correlation with Clinical Response to Gefitinib Therapy." *Science*, 2004, vol. 304, p. 1497-1500.

Soda, M., et al., "Identification of the transforming *EML4-ALK* fusion gene in non-small-cell lung cancer". *Nature*, 2007, vol. 448, p. 561-566.

Takeuchi, K., et al., "*KIF5B-ALK*, a Novel Fusion Oncokinase Identified by an Immunohistochemistry-based Diagnostic System for ALK-positive Lung Cancer". *Clin Cancer Res*, 2009, vol. 15, p. 3143-3149.

Supplementary European Search Report mailed May 15, 2015 in corresponding European Patent Application No. 12820601.8.

M. Takahashi et al., Activation of a Novel Human Transforming Gene, ret, by DNA Rearrangement, Cell, vol. 42, pp. 581-588 (Sep. 1985).

* cited by examiner

METHOD FOR DETERMINING EFFECTIVENESS OF CANCER TREATMENT BY ASSESSING THE PRESENCE OF A KIF5B-RET CHIMERIC GENE

TECHNICAL FIELD

The present invention relates to a fusion gene between the KIF5B gene and the RET gene, and a method for determining the effectiveness of a cancer treatment with a RET protein tyrosine kinase inhibitor targeting said fusion gene. This invention also relates to a method for treatment of cancer utilizing said effectiveness determination. This invention further relates to molecules for use in these methods.

BACKGROUND ART

Cancer is the first-ranked disease among causes of death in Japan, and its therapies are in need of improvement. In particular, lung cancer is at the top of the causes of cancer death not only in Japan but also throughout the world, causing over a million deaths each year. Lung cancer is broadly divided into small-cell lung carcinoma and non-small-cell lung carcinoma, and the non-small-cell lung carcinoma is subdivided into three subgroups: lung adenocarcinoma (LADC), lung squamous cell carcinoma, and large-cell carcinoma. Among these subgroups, LADC accounts for about 50% of all cases of non-small-cell lung carcinoma, and besides its frequency is elevated (Non-patent Document 1).

It has been found that a considerable proportion of LADCs develop through activation of oncogenes. It has also been revealed that when the activation of oncogenes occurs, somatic mutations in the EGFR gene (10-40%) or the KRAS gene (10-20%), fusion between the ALK gene and the EML4 (echinoderm microtubule-associated protein-like 4) gene, fusion between the ALK gene and the KIF5B gene (5%), or other alterations occur in a mutually exclusive way (Non-patent Documents 2-6).

In the field of human cancers including lung adenocarcinoma, there is a strong need for identifying oncogenes involved in the onsets of such cancers, such as mutant genes (mutant proteins) and fusion genes (fusion proteins), because such an identification will greatly contribute to development of novel cancer treatment and testing methods targeting such genes.

In particular, advanced lung cancers are mainly treated with drugs, but individual patients exhibit greatly different responses to a drug, so there is needed a means for predicting what drug is therapeutically effective in each case. Thus, identification of molecules that can serve as indicators for such predictions, such as mutant genes and fusion genes is in progress, as noted above; for example, it has been shown that tyrosine kinase inhibitors targeting EGFR and ALK proteins are particularly effective for treatment of LADCs harboring EGFR mutations and/or ALK fusions. Further, a technique for detecting a fusion of the ALK tyrosine kinase gene as observed in 4-5% of lung cancer cases has been developed as a method to screen for cases to be indicated for an inhibitor against ALK protein tyrosine kinase, and its clinical trials are currently underway.

However, a thorough elucidation of fusion genes and the like in various cancers including lung cancers has not yet been achieved, and there is still a demand for identifying mutant genes and fusion genes that can serve as indicators for predicting the effectiveness of drug treatments.

CITATION LIST

Non-Patent Documents

Non-patent Document 1: Herbst, R. S., et al., *The New England Journal of Medicine*, 2008, Vol. 359, p. 1367-1380

Non-patent Document 2: Paez, J. G., et al., *Science*, 2004, Vol. 304, p. 1497-1500

Non-patent Document 3: Takeuchi, K., et al., *Clin Cancer Res*, 2009, Vol. 15, p. 3143-3149

Non-patent Document 4: Soda, M., et al., *Nature*, 2007, Vol. 448, p. 561-566

Non-patent Document 5: Janku, F., et al., *Nat Rev Clin Oncol*, 2010, Vol. 7, p. 401-414

Non-patent Document 6: Lovly, C. M., et al., *Nat Rev Clin Oncol*, 2011, Vol. 8, p. 68-70

SUMMARY OF INVENTION

Technical Problem

The present invention has been made in consideration of the above-described problems of the prior art, and has as its object to identify genes that can serve as indicators for predicting the effectiveness of drug treatments as in lung cancers. Another object of this invention is to provide novel methods for predicting the effectiveness of drug treatments targeting said genes. Still another object of this invention is to provide methods for treating lung cancers and the like on the basis of the prediction of the effectiveness of drug treatments targeting said genes. Yet another object of this invention is to provide molecules for use in detecting said genes in these methods.

Solution to Problem

As a result of intensive studies to achieve the above-mentioned objects, the present inventors have identified in-frame fusion transcripts between the kinesin family member 5B (KIF5B) gene and the RET receptor tyrosine kinase oncogene (the RET gene) by performing whole-transcriptome sequencing of 30 LADC specimens. These fusion genes are generated by the inversion of the region p11-q11 on chromosome 10. The KIF5B-RET gene fusions were detected in 6 out of 319 (2%) LADC specimens from Japanese individuals, but none of the six subjects with said gene fusion detected had known oncogene-activating mutations such as EGFR or KRAS mutations or ALK fusions. This fusion transcript was also observed in an LADC specimen from a U.S.A. individual (1 out of 80 (1%)). These facts revealed that said gene fusions are responsible mutations (driver mutations) for oncogenesis in individuals of a wide variety of races.

It is considered that this gene fusion induces constitutive activation of RET tyrosine kinase and hence inhibitors against RET tyrosine kinase may be therapeutically effective in patients with such an activation. Thus, the present inventors have found that it is possible to predict the effectiveness of treatments of lung cancer and the like with drugs targeting this gene fusion, and that efficient treatments can be performed by administering the drugs to patients in whom the treatments with the drugs have been determined to be effective on the basis of this prediction, and the inventors have completed the present invention.

Therefore, the present invention relates to a fusion polypeptide between KIF5B and RET, a method for determining the effectiveness of a cancer treatment with a RET tyrosine kinase inhibitor using the presence of said polypeptide as an indicator, a method for treatment of cancer utilizing said effectiveness determination, and molecules for use in these methods. More specifically, this invention provides the following:

(1) A polypeptide wherein the N-terminal moiety of KIF5B protein and the C-terminal moiety of RET protein are fused together;

(2) A polynucleotide encoding the polypeptide as set forth in (1);

(3) A method for determining the effectiveness of a cancer treatment with a RET tyrosine kinase inhibitor, the method comprising the step of detecting the presence or absence of the polynucleotide as set forth in (2) in a sample isolated from a patient, wherein in a case where the presence of the polynucleotide is detected, the cancer treatment with the RET tyrosine kinase inhibitor is determined to be highly effective in the patient;

(4) An agent for determining the effectiveness of a cancer treatment with a RET tyrosine kinase inhibitor by the method as set forth in (3), the agent comprising any of the polynucleotides noted below in (a) to (c), which have a chain length of at least 15 nucleotides, or the antibody noted below in (d):

(a) a polynucleotide that is at least one probe selected from the group consisting of a probe that hybridizes to a polynucleotide encoding KIF5B protein and a probe that hybridizes to a polynucleotide encoding RET protein;

(b) a polynucleotide that is a probe that hybridizes to a point of fusion between a polynucleotide encoding KIF5B protein and a polynucleotide encoding RET protein;

(c) polynucleotides that are a pair of primers designed to sandwich a point of fusion between a polynucleotide encoding KIF5B protein and a polynucleotide encoding RET protein; and (d) an antibody that binds to a polypeptide having KIF5B protein and RET protein fused together;

(5) A method for treatment of cancer, comprising the step of administering a RET tyrosine kinase inhibitor to a patient in whom a cancer treatment with the RET tyrosine kinase inhibitor has been determined to be highly effective by the method as set forth in (3); and (6) A therapeutic agent for cancer, comprising a RET tyrosine kinase inhibitor as an active ingredient, the agent which is to be administered to a patient in whom a cancer treatment with the RET tyrosine kinase inhibitor has been determined to be highly effective by the method as set forth in (3).

Advantageous Effects of Invention

The present invention enables prediction of the effectiveness of cancer treatments, in particular, prediction of the effectiveness of cancer treatments with RET tyrosine kinase inhibitors. This prediction makes it possible to avoid administration of drugs to cancer patients in whom administration of the agenet is considered to be ineffective, thereby allowing efficient cancer treatments.

BRIEF DESCRIPTIONS OF DRAWINGS

FIG. 1 depicts a schematic drawing showing the structures of wild-type KIF5B and RET proteins ("KIF5B" and "RET" in the upper part of this figure), as well as the four KIF5B-RET fusion variants ("1 to 4" in the lower part of this figure) identified in LADC patients, together with the breakpoints of the respective variants (lines drawn in "KIF5B" and "RET" in the upper part of this figure (Nos. 1, 2, 3, 4, and 1-3)). In this figure, "TM" indicates a transmembrane domain.

FIG. 2 depicts schematic drawings showing the KIF5B-RET fusion transcript in a LADC patient (case BR0020). The upper part of this figure shows the results of paired-end read analysis, while the lower part shows the results of junction read analysis. Nucleotides (A, T, G and C) are distinguished from each other by different colors shown in this figure.

FIG. 3 depicts electrophoresis photos each showing the results of detection by RT-PCR of a KIF5B-RET fusion (upper part of this figure), a RET kinase domain (exon 12-13; middle part of this figure), and glyceraldehyde-3-phosphate dehydrogenase (GAPDH, internal standard; lower part of this figure) in each LADC patient. In this figure, the columns titled "T" show the results for a LADC tissue of each LADC patient, and the column titled "N" show the results for a non-cancerous lung tissue from each LADC patient (the same is true of FIG. 5). BR0019 is a subject with a KIF5B-RET fusion negative LADC, and BR0020, BR1001, BR1002, BR0030, BR1003 and BR1004 are subjects with KIF5B-RET fusion positive LADCs (the same is true of FIG. 5). "NTC" indicates the results for a negative control without template DNA.

FIG. 4 depicts electropherograms showing the results of analysis by Sanger sequencing of cDNAs of KIF5B-RET fusion transcripts. The RT-PCR products amplified using the primers KIF5B-RET-F1 and KIF5B-RET-R1 were directly sequenced using the primer KIF5B-RET-F1 (in BR0020, BR1001, BR1002 and BR0030) or KIF5B-F-orf2438 (in BR1003 and BR1004).

FIG. 5 depicts an electrophoresis photo showing the results of detection by genomic PCR of KIF5B-RET fusions in respective LADC patients. In this figure, the locations of the primers used to amplify the DNA fragments containing the fusion points between the KIF5B gene and the RET gene (breakpoint junctions) are indicated under the photo. "int" indicates an intron, and "ex" indicates an exon. Nonspecific bands observed in non-cancerous lung tissues from BR0030 and BR1004 are indicated by asterisks.

FIG. 6 depicts electropherograms showing the results of analysis by Sanger sequencing of the genomic fragments containing the fusion points between the KIF5B gene and the RET gene. The PCR products were analyzed by direct sequencing. The following primers were used for amplification and sequencing of the respective samples: BR0020: KIF5B-int15-F1/KIF5B-RET-R1 and RET-int11-R0.5; BR1001: KIF5B-int15-F1/KIF5B-RET-R1 and RET-int11-R1; BR1002: KIF5B-int15-F2/RET-int11-R3 and KIF5B-int15-F3.5; BR0030: KIF5B-ex16-F1/KIF5B-RET-R1 and KIF5B-ex16-F1; BR1003: KIF5B-ex23-F1/KIF5B-RET-R1 and KIF5B-ex23-F1. Overlapped nucleotides at the fusion points between the KIF5B gene and the RET gene are indicated by boxes in the electropherograms for BR1002 and BR0030, and inserted nucleotides (insertion) at the fusion points are indicated by boxes in the electropherograms for BR1001 and BR1003.

FIG. 7 depicts an electropherogram showing the result of analysis by Sanger sequencing of a genomic fragment containing a KIF5B-RET fusion point (in particular, a result showing that a 349 bp genomic fragment containing RET exon 7-RET intron 7 is inserted into a breakpoint junction). The PCR product amplified using the primers KIF5B-ex24-F1 and RET-int7-R1 was directly sequenced using the primer RET-int7-R2.

FIG. 8 depicts schematic drawings showing the results of determining the genome copy numbers of chromosome 10 in two (BR0020 and BR1001) out of the six cases with fusions between the KIF5B gene and the RET gene. The copy numbers were estimated based on the analysis with the CNAG program (the same is true of FIG. 9). In this figure, the locations and directions of the KIF5B gene and the RET gene on the reference genome are indicated by arrows (the same is true of FIG. 9).

Figure 11:
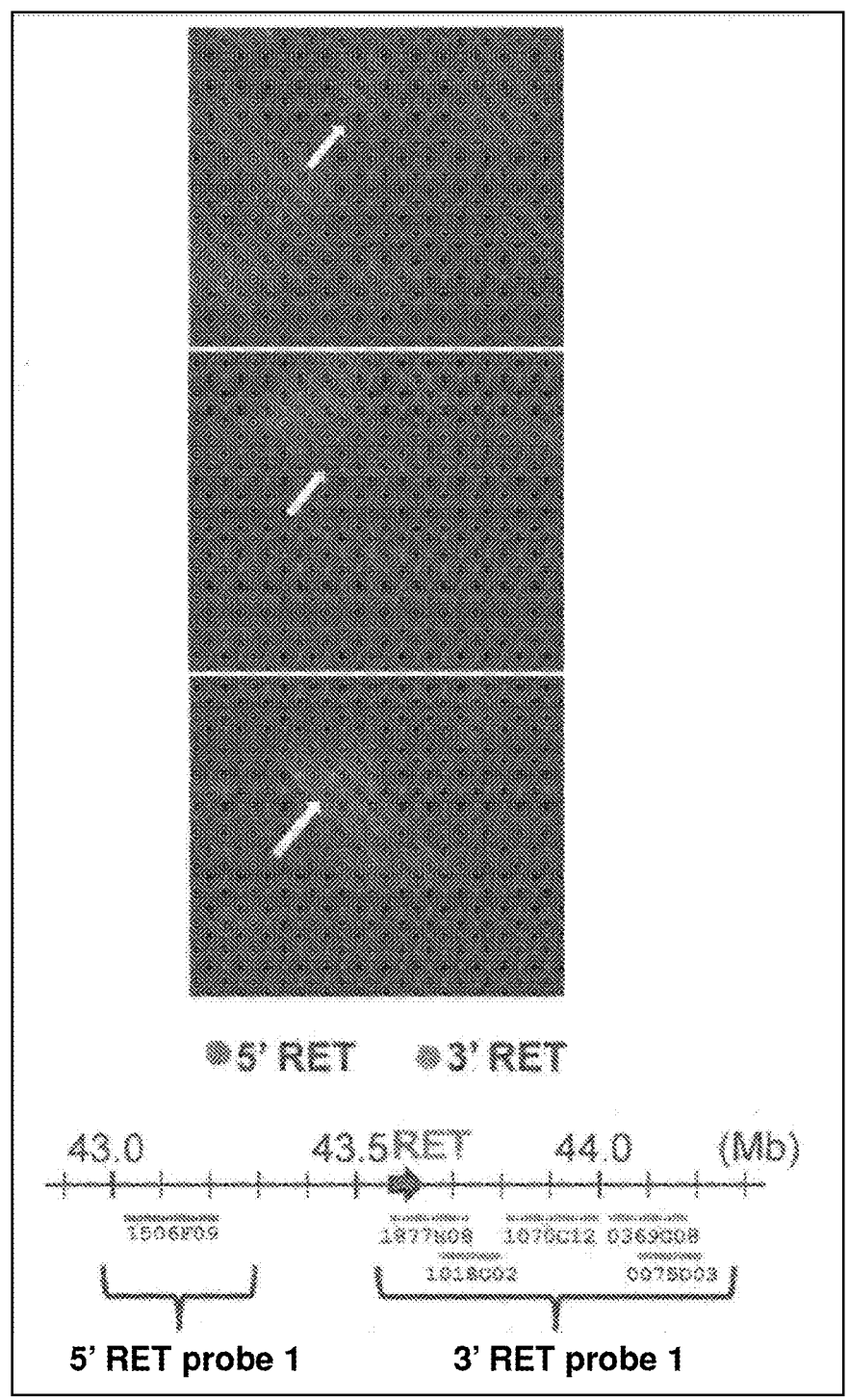

FIG. 11 depicts photomicrographs (magnification: 400×) showing a chromosomal inversion causing a KIF5B-RET fusion in case BR0020, which was detected by in situ hybridization performed using fluorescently labeled DNA probes. In this case, there was detected a split (indicated by arrows in this figure) in the signals from a probe that hybridizes to the portion consisting of a region upstream from the coding region for the kinase domain of the RET gene toward the 5' terminal (5' RET, red fluorescent spot shown in this figure), and a probe that hybridizes to the portion consisting of said coding region and a region downstream from said coding region toward the 3' terminal (3' RET, green fluorescent spots shown in this figure). The hybridization locations of the respective probes on the genome are also illustrated in the lower part of this figure.

Figure 12:
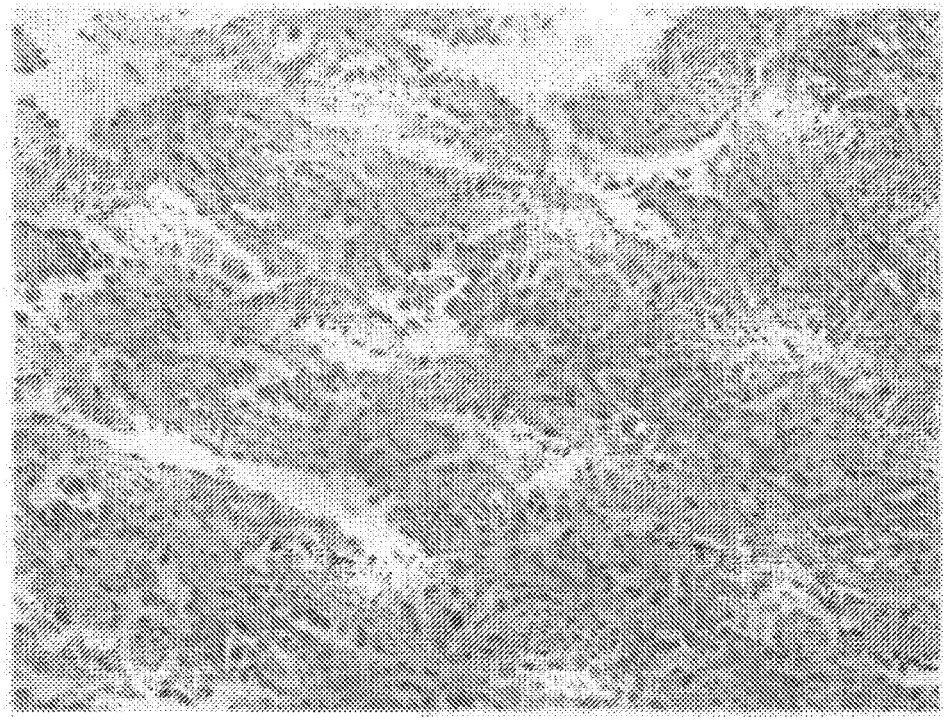

FIG. 12 depicts a photomicrograph (magnification: 50×) showing a representative histology of a KIF5B-RET fusion positive LADC (BR1004) stained with hematoxylin-eosin. In the LADC cells from this case, there was observed a differentiation of Clara cells or type II alveolar epithelial cells. These tumor cells extended to the periphery of the tumors along the thickened alveolar walls (left half of this panel). Papillary growth was also observed in the middle section (right half of this panel).

Figure 13:
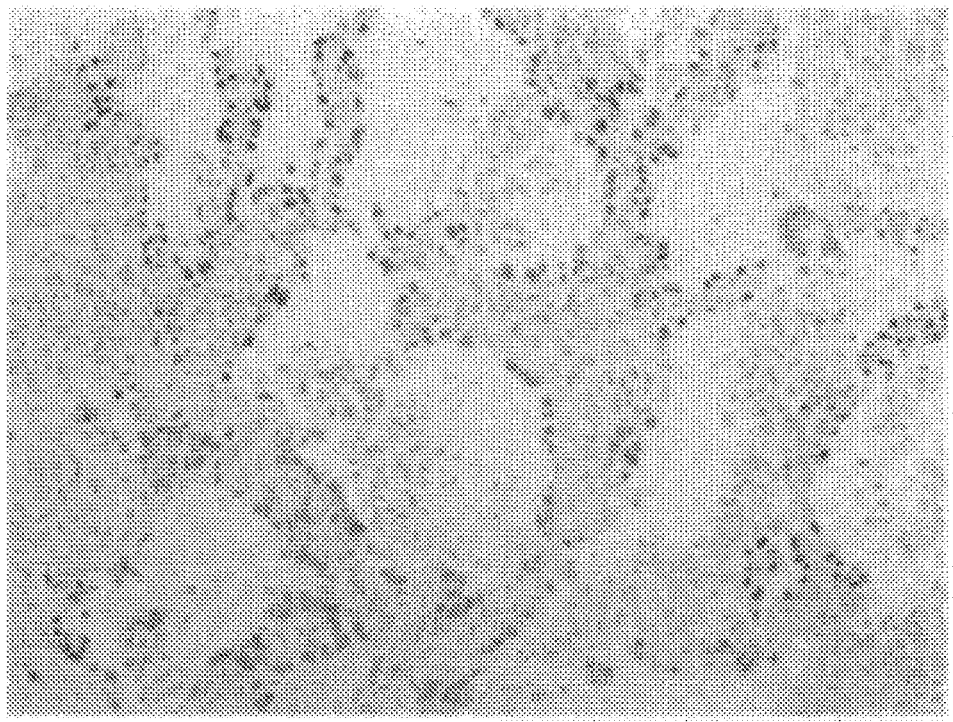

FIG. 13 depicts a photomicrograph (magnification: 50×) showing a representative histology of a KIF5B-RET fusion positive LADC (BR1004) immunostained for thyroid transcription factor-1 (TTF-1). In the LADC cells from this case, there was observed a diffuse strong nuclear expression of TTF-1.

Figure 14:
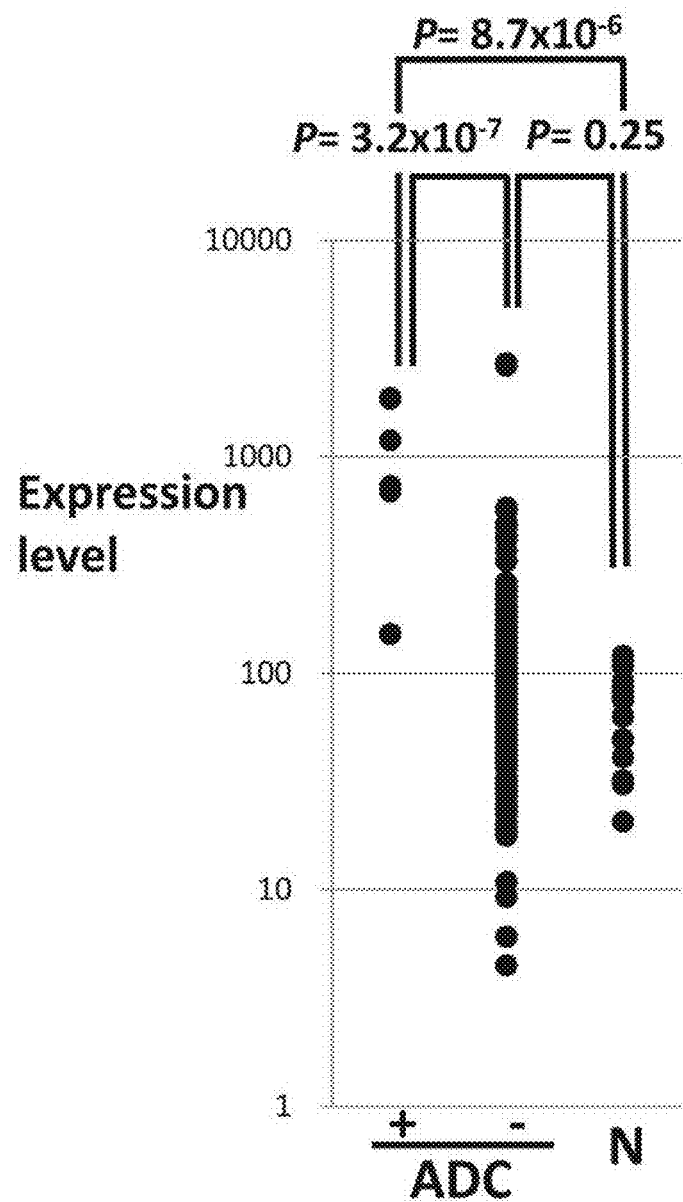

FIG. 14 depicts a plotted graph showing the results of determination of the RET expression levels in LADCs ("ADC") and non-cancerous lung tissues ("N") by analysis with U133A plus 2.0 microarrays. The RET expression levels were determined using the probe 211421_s_at (ret proto-oncogene (multiple endocrine neoplasia and medullary thyroid carcinoma 1, Hirschsprung disease)). In this figure, "+" indicates the results of determination of KIF5B-RET fusion positive LADCs, and "−" indicates the results of determination of KIF5B-RET fusion negative LADCs. The P values shown in this figure were obtained by determining the differences in expression level by U test.

Figure 15:
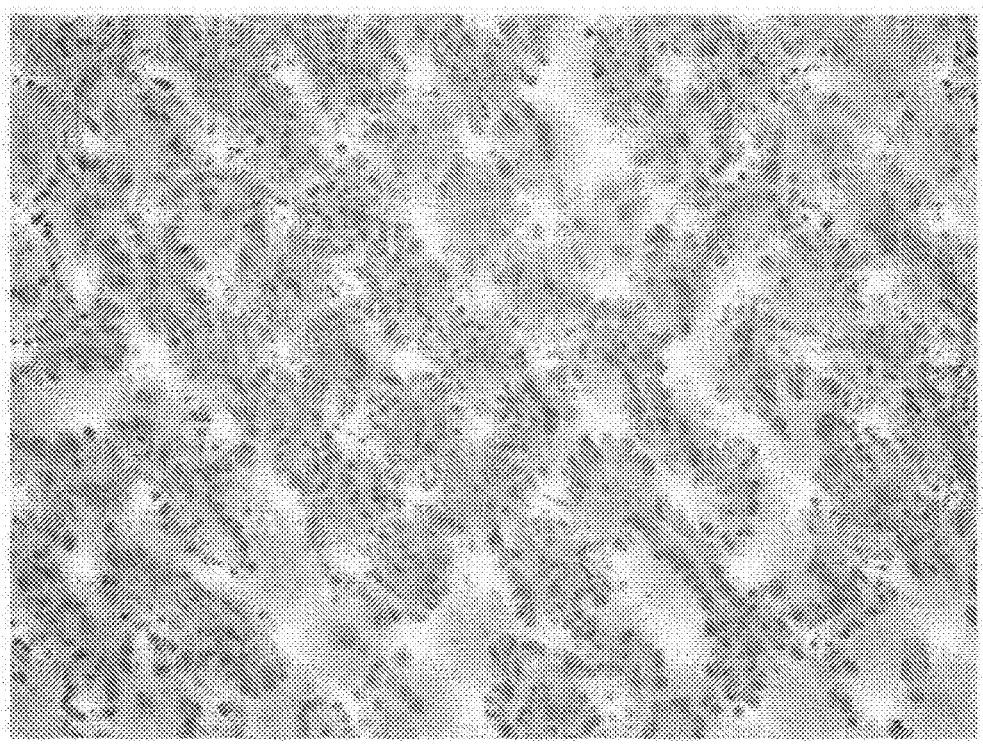

FIG. 15 depicts a photomicrograph (magnification: 50×) showing the results of immunohistological staining of RET protein in a KIF5B-RET fusion positive LADC tumor sample (BR1004). In this LADC tumor sample, RET protein was observed to be expressed in a glanular pattern in the cytoplasm of adenocarcinoma cells.

Figure 16:
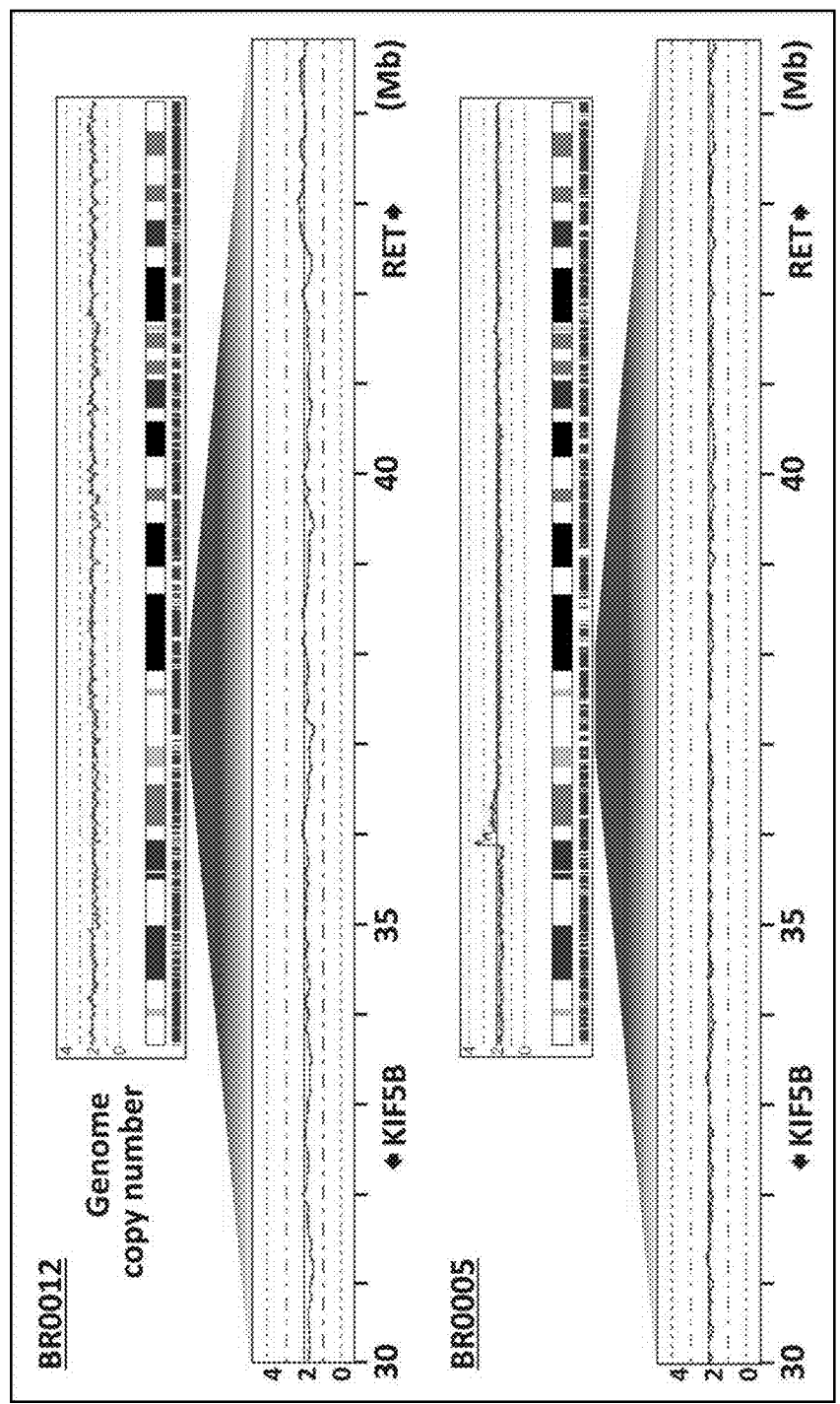

FIG. 16 depicts schematic drawings showing the results of determining the genome copy numbers of chromosome 10 in the two cases which had no RET fusion but showed high RET gene expression level. The copy numbers were estimated based on the analysis with the CNAG program. In this figure, the locations and directions of the KIF5B gene and the RET gene are indicated by arrows.

Figure 17:
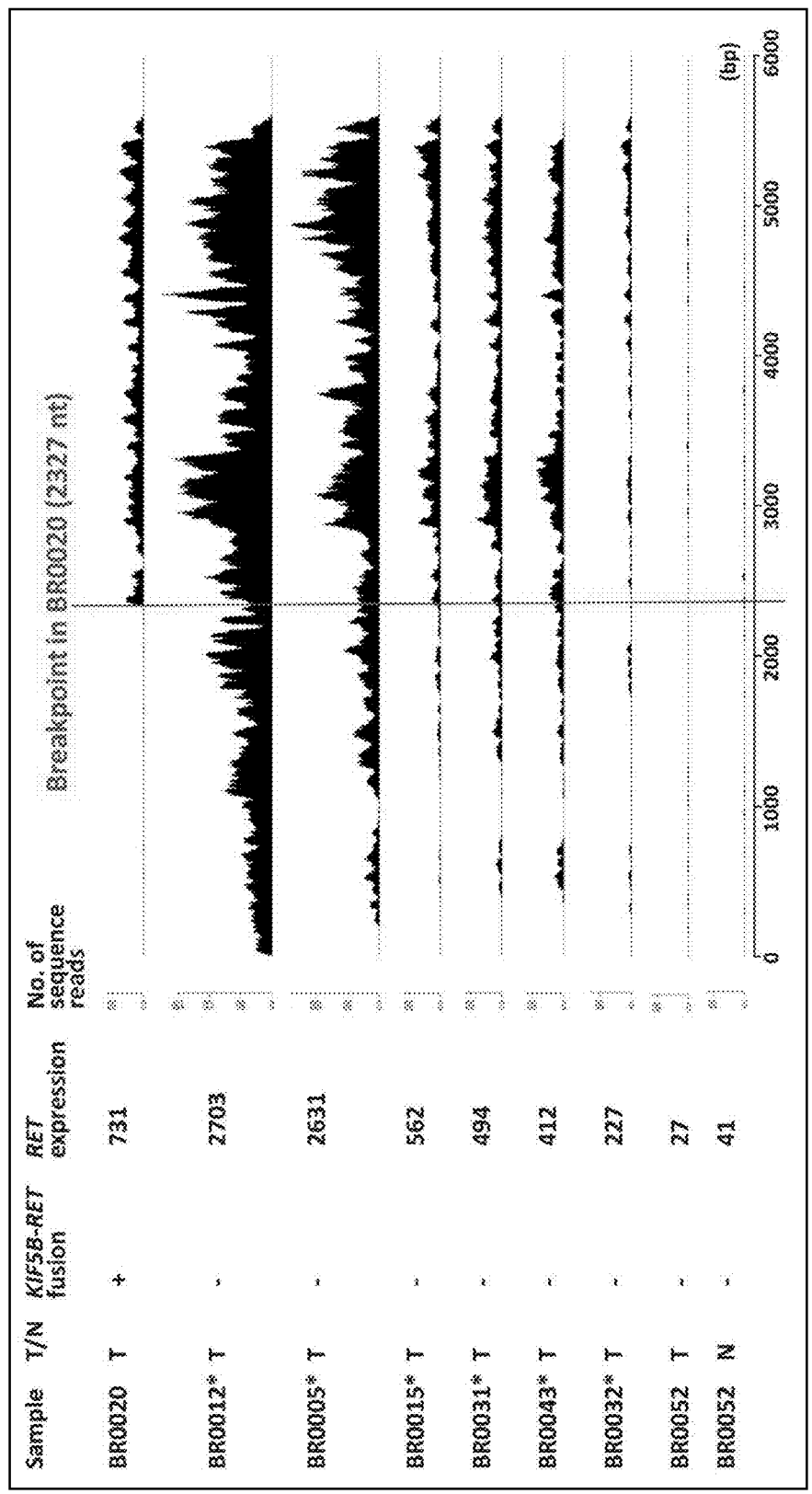

FIG. 17 depicts a drawing showing the results of representing the distributions of sequence reads from LADCs and a non-cancerous lung tissue along the RET transcript (NM_020975.4). Most of the sequence reads from the KIF5B-RET fusion positive sample BR0020 were located downstream from its fusion point. On the other hand, in six samples which had no fusion but showed RET gene expression (samples marked with asterisks in this figure), sequence reads were distributed over the whole RET transcripts, and no mutations were detected. In this figure, the column titled "RET expression" shows the RET expression levels determined by oligonucleotide microarrays.

Figure 18:
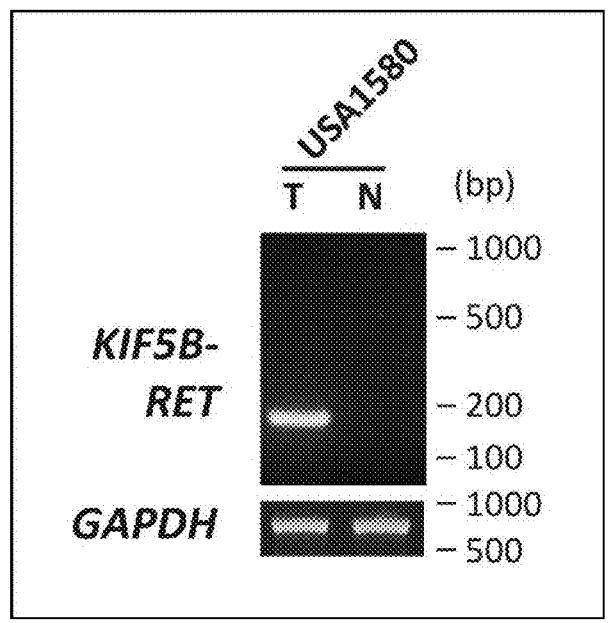

FIG. 18 depicts electrophoresis photos showing the results of detection by RT-PCR of a KIF5B-RET fusion transcript (variant 1, upper part of this figure) and GAPDH (internal standard, lower part of this figure) in a LADC case in the USA cohort. In this figure, the column titled "T" shows the results for the LADC tissue from the case in this cohort, and the column titled "N" shows the results for the non-cancerous lung tissue from the case in this cohort. "USA1580" indicates the LADC case in the USA cohort.

Figure 19:
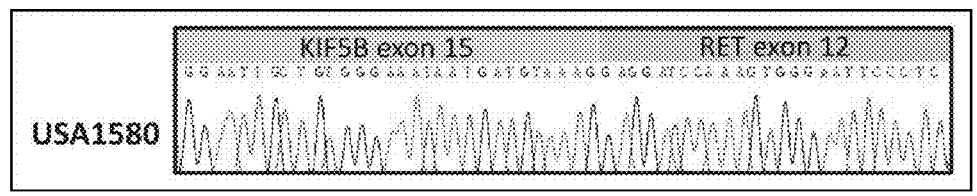

FIG. 19 depicts an electropherogram showing the result of analysis by Sanger sequencing of cDNA of the KIF5B-RET fusion transcript (variant 1) in a LADC case in the USA cohort.

DESCRIPTION OF EMBODIMENTS

<KIF5B-RET Fusion Polypeptide and Polynucleotide Encoding Said Polypeptide>

As disclosed below in Examples, fusion cases between KIF5B protein and RET protein were first observed in LADCs. Thus, the present invention provides a polypeptide wherein the N-terminal moiety of KIF5B protein and the C-terminal moiety of RET protein are fused together (hereinafter also referred to as the "KIF5B-RET fusion polypeptide"). This invention also provides a polynucleotide encoding said polypeptide (hereinafter also referred to as the "KIF5B-RET fusion polynucleotide").

According to the present invention, the "KIF5B (kinesin family member 5B) protein" is a protein that is also called KNS1 (kinesin 1) protein, UKHC (kinesin, heavy chain, ubiquitous) protein, or KINH protein, and refers to a protein encoded by the gene located at chromosome 10p11.2 in humans. In this invention, the "KIF5B protein", if it is derived from humans, is a protein consisting of the amino acid sequence as typically shown in SEQ ID NO: 2. Further, for the purpose of this invention, the "N-term moiety of KIF5B protein" refers to a moiety that typically comprises the motor domain that is located on the N-terminal side of said KIF5B protein and part or all of the coiled-coil domain (refer to FIG. 1).

According to the present invention, the "RET (rearranged during transfection) protein" is a protein that is also called RET tyrosine kinase protein or RET receptor tyrosine kinase protein, and refers to a protein encoded by the gene located at 10q11.2 in humans. In this invention, the "RET protein", if it is derived from humans, is a protein consisting of the amino acid sequence as typically shown in SEQ ID NO: 4. Further, for the purpose of this invention, the "C-terminal moiety of RET protein" refers to a moiety that typically comprises a kinase domain which is located on the C-terminal side of said RET protein (refer to FIG. 1).

The "polypeptide wherein the N-terminal moiety of KIF5B protein and the C-terminal moiety of RET protein are fused together" according to the present invention may be any polypeptide that is encoded by the fusion gene resulting from the inversion of the region 10p11.2 to 10q11.2 as described below in Examples, and typically is a polypeptide characterized in that a polypeptide comprising the motor domain that is located on the N-terminal side of said KIF5B protein and part or all of the coiled-coil domain, is fused with a polypeptide comprising a kinase domain which is located on the C-terminal side of said RET protein; and examples include a polypeptide consisting of the amino acid sequence shown in SEQ ID NO: 6, 8, 10 or 12.

The amino acid sequences of the "KIF5B protein", "RET protein", and "KIF5B-RET fusion polypeptide" according to the present invention can mutate in nature (i.e., in a non-artificial way). Alternatively, a mutation may be artificially introduced into any amino acid(s). Thus, such mutants are also encompassed by the present invention.

Exemplary mutants of the KIF5B-RET fusion polypeptide include proteins consisting of an amino acid sequence having one or more amino acids substituted, deleted, added and/or inserted in the amino acid sequence shown in SEQ ID NO: 6, 8, 10 or 12. As used herein, the term "more" refers to generally 50 or fewer amino acids, preferably 30 or fewer amino acids, more preferably 10 or fewer amino acids, and particularly preferably some or fewer amino acids (for example, five or fewer amino acids, three or fewer amino acids, two or one amino acid, one amino acid).

Other exemplary mutants of the KIF5B-RET fusion polypeptide include polypeptides encoded by a DNA that hybridizes under stringent conditions to a DNA consisting of the nucleotide sequence shown in SEQ ID NO: 5, 7, 9 or 11. Exemplary high stringent hybridization conditions are 0.2× SSC at 65° C., and exemplary low stringent hybridization conditions are 2.0×SSC at 50° C.

Still other exemplary mutants of the KIF5B-RET fusion polypeptide include polypeptides consisting of an amino acid sequence having at least 80% (for example, at least 85%, 90%, 95%, 97%, 99%) homology to the amino acid sequence shown in SEQ ID NO: 6, 8, 10 or 12. Sequence homology can be determined using the BLASTX or BLASTP (amino acid level) program (Altschul, et al., *J. Mol. Biol.,* 215: 403-410, 1990). These programs are based on the algorithm BLAST developed by Karlin and Altschul (*Proc. Natl. Acad. Sci. USA,* 1990, 87: 2264-2268; and *Proc. Natl. Acad. Sci. USA,* 1993, 90: 5873-5877). When amino acid sequence analysis is made using BLASTX or the like, the parameter setting is typically made as follows: score=50 and wordlength=3. Amino acid sequence analysis with the Gapped BLAST program can be performed as described in Altschul, et al. (*Nucleic Acids Res.,* 1997, 25: 3389-3402). When amino acid sequence analysis is made using the BLAST and Gapped BLAST programs, the default parameters of these programs are used. The specific procedures for conducting these analyses are known.

The "polynucleotide encoding the KIF5B-RET fusion polypeptide" according to the present invention includes mRNAs encoding said polypeptide, cDNAs encoding said polypeptide, genomic DNAs encoding said polypeptide, and the like. Typical examples of the cDNAs encoding the KIF5B-RET polypeptide of this invention are polynucleotides consisting of the DNA sequence shown in SEQ ID NO: 5, 7, 9 or 11.

The polynucleotide of the present invention can be extracted by those skilled in the art using a known hybridization technique from a cDNA library or genomic DNA library prepared from LADC or the like harboring the fusion gene between the KIF5B gene and the RET gene. The polynucleotide can also be prepared by amplification utilizing a known gene amplification technique (PCR), with the mRNA, cDNA or genomic DNA prepared from LADC or the like being used as a template. Alternatively, the polynucleotide can be prepared utilizing a known gene amplification or genetic recombination technique such as PCR, restriction enzyme treatment, or site-directed mutagenesis (Kramer, W. & Fritz, H J., *Methods Enzymol,* 1987, 154, 350), with the cDNAs of the wild-type KIF5B gene and the wild-type RET gene being used as starting materials.

Furthermore, after the thus-prepared polynucleotide is inserted into an appropriate expression vector, the vector is introduced into a cell-free protein synthesis system (e.g., reticulocyte extract, wheat germ extract) and the system is incubated, or alternatively the vector is introduced into appropriate cells (e.g., *E coli,* yeast, insect cells, animal cells) and the resulting transformant is cultured; in either way, the polypeptide of the present invention can be prepared.

<Method for Determining the Effectiveness of a Cancer Treatment with a RET Tyrosine Kinase Inhibitor>

As disclosed below in Examples, it has been found that the fusion between the KIF5B gene and the RET gene is a responsible mutation for cancers—this fusion enhances expression of RET tyrosine kinase protein, in turn leading to constitutive activation of RET tyrosine kinase protein and typically contributing to malignant transformation of cancers. Thus, it is highly probable that cancer patients with detection of such a fusion are responsive to treatments with RET tyrosine kinase inhibitors.

Therefore, the present invention provides a method for determining the effectiveness of a cancer treatment with a RET tyrosine kinase inhibitor, the method comprising the step of detecting the presence or absence of a KIF5B-RET fusion polynucleotide in a sample isolated from a patient, wherein in a case where the presence of the polynucleotide is detected, the cancer treatment with the RET tyrosine kinase inhibitor is determined to be highly effective in the patient.

For the purpose of the present invention, the "patient" can be not only a human suffering from a cancer but also a human suspected of having a cancer. The "cancer" to which the method of this invention is to be applied is not particularly limited as long as it is a cancer with expression of a fusion gene between the KIF5B gene and the RET gene. The cancer is preferably a lung cancer, more preferably a non-small-cell lung carcinoma, and particularly preferably lung adenocarcinoma.

For the purpose of the present invention, the term "sample" includes not only biological samples (for example, cells, tissues, organs, body fluids (e.g., blood, lymphs), digestive juices, sputum, bronchoalveolar/bronchial lavage fluids, urine, and feces), but also nucleic acid extracts from these biological samples (for example, genomic DNA extracts, mRNA extracts, and cDNA and cRNA preparations from mRNA extracts) and protein extracts. The sample may also be the one that is fixed with formalin or alcohol, frozen, or embedded in paraffin.

Further, the genomic DNA, mRNA, cDNA or protein can be prepared by those skilled in the art through considering various factors including the type and state of the sample and selecting a known technique suitable therefor.

For the purpose of the present invention, the "RET tyrosine kinase inhibitor", the cancer treatment with which is to be evaluated for effectiveness, is not particularly limited as long as it is a substance capable of directly or indirectly suppressing the ability of RET tyrosine kinase. The inhibitor may also be a substance that suppresses other tyrosine kinases as long as it is capable of inhibiting RET tyrosine kinase. Examples of known RET tyrosine kinase inhibitors that can be applied to the present invention include 4-(4-bromo-2-fluoroanilino)-6-methoxy-7-(1-methylpiperidin-4-ylmethoxy)quinazoline (generic name: Vandetanib; compound targeting VEGFR, EGFR, and RET), 4-[4-[3-[4-chloro-3-(trifluoromethyl)phenyl]ureido]phenoxy]-N-methylpyridin-2-carboxamide (generic name: Sorafenib; compound targeting BRAF, RET, and the like), N-[2-(diethylamino)ethyl]-5-[(Z)-(5-fluoro-2-oxo-1,2-dihydro-3H-indol-3-ylidene)methyl]-2,4-dimethyl-1H-pyrrole-3-carboxamide mono[(2S)-2-hydroxysuccinate] (generic name: Sunitinib; compound targeting PDGFR, VEGFR, RET, and the like), N-(3,3-dimethylindolin-6-yl)-2-(pyridin-4-ylmethylamino)nicotinamide (generic name: Motesanib; compound targeting PDGFR, VEGFR, RET, and the like), and XL184/Cabozantinib (compound targeting VEGFR, MET, RET, and the like).

In the present invention, the "detection of the presence or absence of a KIF5B-RET fusion polynucleotide" can be performed directly on a genomic DNA encoding said fusion polypeptide or a transcript from said genomic DNA, or can be performed indirectly for a translation product from said transcript (foregoing fusion polypeptide).

Since the genomic DNA encoding the foregoing fusion polypeptide is formed by inversion of the region 10p11.2 to 10q11.2, the "detection of the presence or absence of a KIF5B-RET fusion polynucleotide" may be achieved by detecting this phenomenon of inversion. The detection of such an inversion may be achieved by, for example, detecting a split between the portion consisting of a region upstream from the coding region for the kinase domain of the RET gene toward the 5' terminal, and the portion consisting of said coding region and a region downstream from said coding region toward the 3' terminal, or detecting a split between the portion consisting of the coding region for the cadherin repeat of the RET gene and a region upstream from said coding region toward the 5' terminal, and the portion consisting of the coding region for the transmembrane domain of the RET gene and a region downstream from said coding region toward the 3' terminal, or detecting a split between the portion consisting of part or all of the cording region for the coiled-coil domain of the KIF5B gene and a region upstream from said coding region toward the 5' terminal, and the portion consisting of a region downstream from said cording region toward the 3' terminal.

The "detection of the presence or absence of a KIF5B-RET fusion polynucleotide" according to the present invention can be performed using a known method. Exemplary methods that can be used in the detection on the "genomic DNA encoding the foregoing fusion polypeptide" include in situ hybridization (ISH) based on fluorescence, etc., genomic PCR, direct sequencing, Southern blotting, and genome microarray analysis. Exemplary methods that can be used in the detection on the "transcript from said genomic DNA" include RT-PCR, direct sequencing, Northern blotting, dot blotting, and cDNA microarray analysis.

Biological samples (e.g., biopsy samples) obtained in the process of treatment or diagnosis are often fixed in formalin, and when such samples are subjected to that detection, it is preferred to use in situ hybridization because the genomic DNA to be detected is stable even when fixed in formalin and the detection sensitivity is high.

According to in situ hybridization, the genomic DNA encoding the KIF5B-RET fusion polypeptide can be detected by hybridizing the polynucleotide noted below in (a) or (b), which has a chain length of at least 15 nucleotides, to such a biological sample:

(a) a polynucleotide that is at least one probe selected from the group consisting of a probe that hybridizes to a polynucleotide encoding KIF5B protein and a probe that hybridizes to a polynucleotide encoding RET protein; and (b) a polynucleotide that is a probe that hybridizes to a point of fusion between a polynucleotide encoding KIF5B protein and a polynucleotide encoding RET protein.

According to the present invention, the polynucleotide encoding KIF5B protein, if it is derived from humans, is typically a gene consisting of the DNA sequence of positions 32237938 to 32285371 in the genome sequence identified by Genbank Accession No. NT_008705.16.

The polynucleotide encoding RET protein according to the present invention, if it is derived from humans, is typically a gene consisting of the DNA sequence of positions 1217582 to 1270862 in the genome sequence identified by Genbank Accession No. NT_033985.7.

However, the DNA sequences of the genes can change in nature (i.e., in a non-artificial way) due to their mutations and the like. Thus, such native mutants can also be encompassed by the present invention (the same applies hereinafter).

The polynucleotide noted in (a) according to the present invention can be of any type as far as it is capable of detecting the presence of the genomic DNA encoding the KIF5B-RET fusion polypeptide in the foregoing biological sample by hybridizing to a nucleotide sequence targeted by said polynucleotide, i.e., a polynucleotide encoding KIF5B protein or a polynucleotide encoding RET protein; preferably, the polynucleotide (a) is any of the polynucleotides noted below in (a1) to (a4):

(a1) a combination of a polynucleotide that hybridizes to the portion consisting of part or all of the cording region for the coiled-coil domain of the KIF5B gene and a region upstream from said coding region toward the 5' terminal (this polynucleotide is hereinafter also referred to as "5' KIF5B probe 1"), and a polynucleotide that hybridizes to the portion consisting of the coding region for the kinase domain of the RET gene and a region downstream from said cording region toward the 3' terminal (this polynucleotide is hereinafter also referred to as "3' RET probe 1");

(a2) a combination of a polynucleotide that hybridizes to the portion consisting of a region upstream from the coding region for the kinase domain of the RET gene toward the 5' terminal (this polynucleotide is hereinafter also referred to as "5' RET probe 1"), and a polynucleotide that hybridizes to the portion consisting of the coding region for the kinase domain of the RET gene and a region downstream from said coding region toward the 3' terminal (3' RET probe 1);

(a3) a combination of a polynucleotide that hybridizes to the portion consisting of the coding region for the cadherin repeat of the RET gene and a region upstream from said coding region toward the 5' terminal (this polynucleotide is hereinafter also referred to as "5' RET probe 2"), and a polynucleotide that hybridizes to the portion consisting of the coding region for the transmembrane domain of the RET gene and a region downstream from said coding region toward the 3' terminal (this polynucleotide is hereinafter also referred to as "3' RET probe 2"); and (a4) a combination of a polynucleotide that hybridizes to the portion consisting of part or all of the cording region for the coiled-coil domain of the KIF5B gene and a region upstream from said coding region toward the 5' terminal (5' KIF5B probe 1), and a polynucleotide that hybridizes to the portion consisting of a region downstream from said cording region toward the 3' terminal (this is hereinafter also referred to as "3' KIF5B probe 1").

In the present invention, the region to which the polynucleotide for use for in situ hybridization as noted above in (a1) is to hybridize (such a region is hereinafter referred to as the "target nucleotide sequence") is preferably located not more than 1000000 nucleotides away from the point of fusion between the KIF5B gene and the RET gene, in terms of specificity for the target nucleotide sequence and detection sensitivity; and the regions to which the polynucleotides for use for in situ hybridization as noted above in (a2) to (a4) are to hybridize are preferably located not more than 1000000 nucleotides away from the breakpoint in the KIF5B gene or the RET gene, in terms of the same factors.

Figure 6:
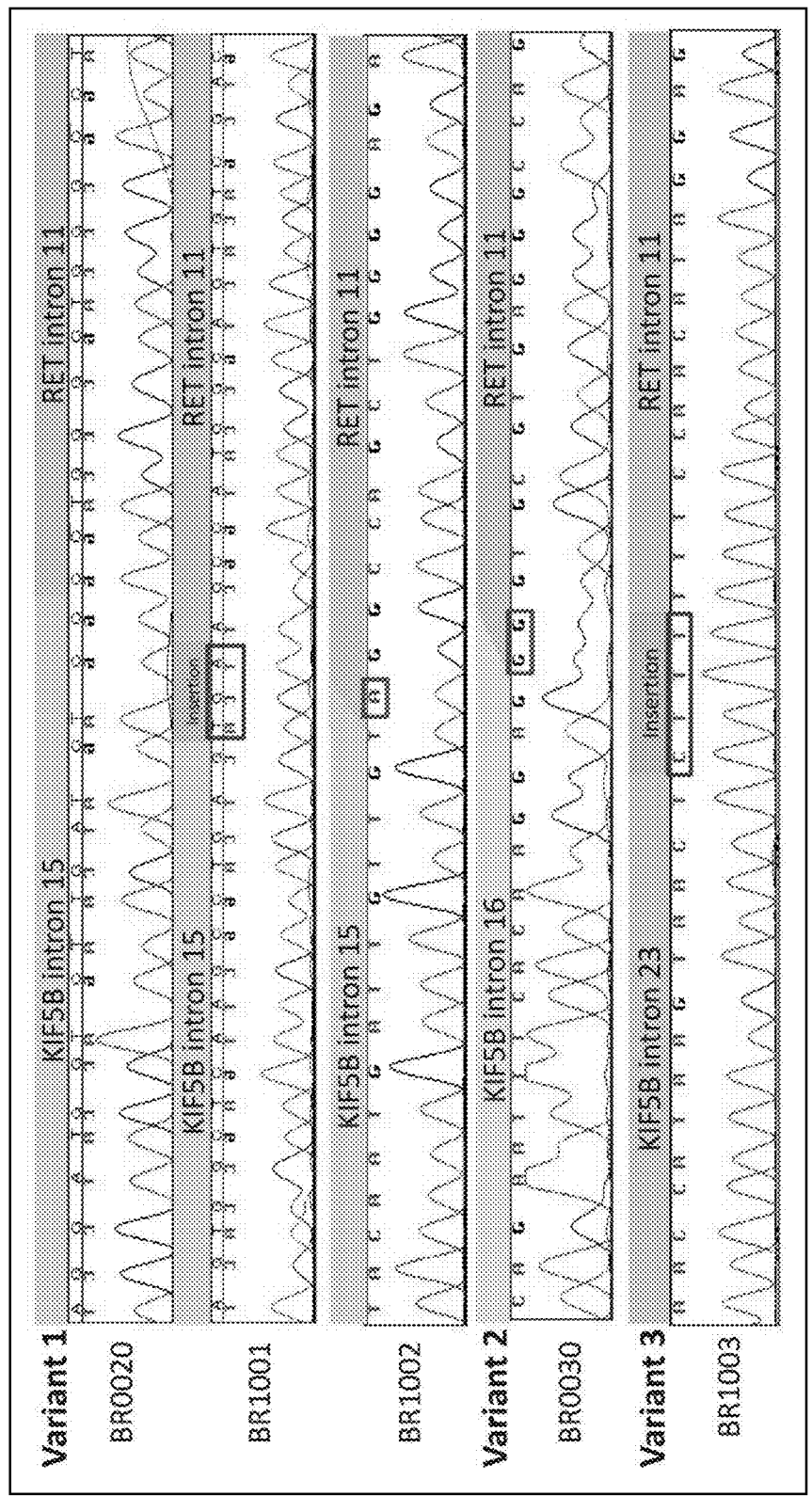
Figure 7:
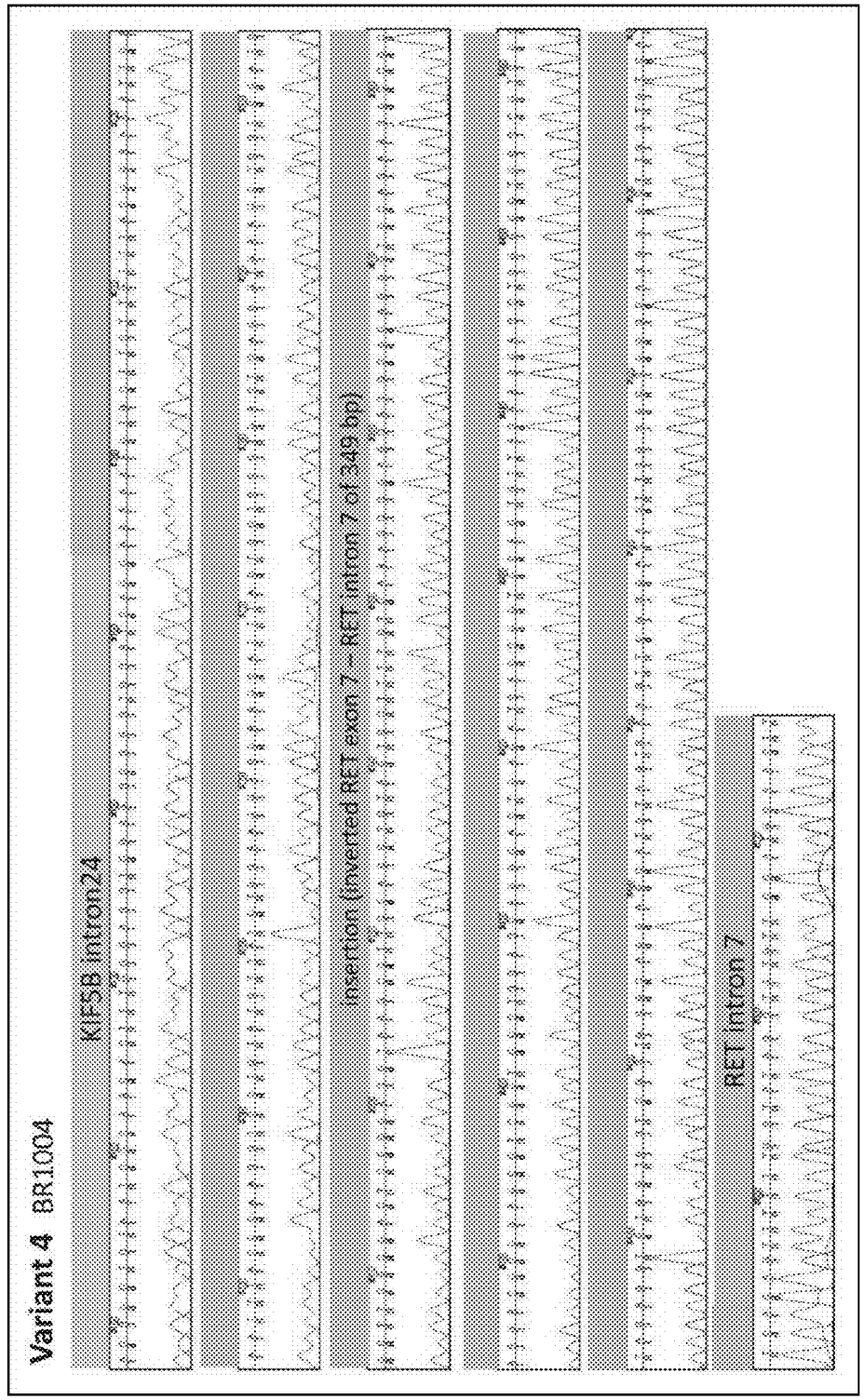

In the present invention, the polynucleotide for use for in situ hybridization as noted above in (b) can be of any type as far as it is capable of detecting the presence of the genomic DNA encoding the KIF5B-RET fusion polypeptide in the foregoing biological sample by hybridizing to a nucleotide sequence targeted by said polynucleotide, i.e., a point of fusion between a polynucleotide encoding KIF5B protein and a polynucleotide encoding RET protein; and typical examples of the polynucleotide (b) are those which each hybridize to a genomic DNA encoding a polynucleotide consisting of the nucleotide sequence shown in SEQ ID NO: 5, 7, 9 or 11, and for example those which each hybridize to the point of fusion between the KIF5B gene and the RET gene as shown in FIGS. 6 and 7

Further, in the present invention, the polynucleotide for use for in situ hybridization as noted above in (a) or (b) is preferably a group consisting of multiple types of polynucleotides which can cover the entire target nucleotide sequence, in terms of specificity for the target nucleotide sequence and detection sensitivity. In such a case, each of the polynucleotides constituting the group has a length of at least 15 nucleotides, and preferably 100 to 1000 nucleotides.

The polynucleotide for use for in situ hybridization as noted above in (a) or (b) is preferably labeled for detection with a fluorescent dye or the like. Examples of such a fluorescent dye include, but are not limited to, DEAC, FITC, R6G, TexRed, and Cy5. Aside from the fluorescent dye, the polynucleotide may also be labeled with a dye (chromogen) such as DAB or with silver or the like based on enzymatic metal deposition.

When in situ hybridization is performed using a combination of 5' KIF5B probe 1 and 3' RET probe 1, a combination of 5' RET probe 1 and 3' RET probe 1, a combination of 5' RET probe 2 and 3' RET probe 2, or a combination of 5' KIF5B probe 1 and 3' KIF5B probe 1, the probes of each combination are preferably labeled with different dyes from each other. If, as the result of in situ hybridization using such a combination of probes labeled with different dyes, an overlap is observed between the signal (e.g., fluorescence) emitted from the label on 5' KIF5B probe 1 and the signal emitted from the label on 3' RET probe 1, then it can be determined that a genomic DNA encoding the KIF5B-RET fusion polypeptide has been detected successfully. Also, if a split is observed between the signal emitted from the label on 5' RET probe 1 and the signal emitted from the label on 3' RET probe 1, or between the signal emitted from the label on 5' RET probe 2 and the signal emitted from the label on 3' RET probe 2, or between the signal emitted from the label on 5' KIF5B probe 1 and the signal emitted from the label on 3' KIF5B probe 1, then it can be determined that a genomic DNA encoding the KIF5B-RET fusion polypeptide has been detected successfully.

Polynucleotide labeling can be effected by a known method. For example, the polynucleotide can be labeled by nick translation or random priming, by which the polynucleotide is caused to incorporate substrate nucleotides labeled with a fluorescent dye or the like.

The conditions for hybridizing the polynucleotide noted above in (a) or (b) to the foregoing biological sample by in situ hybridization can vary with various factors including the length of said polynucleotide; and exemplary high stringent hybridization conditions are 0.2×SSC at 65° C., and exemplary low stringent hybridization conditions are 2.0×SSC at 50° C. Those skilled in the art could realize comparable stringent hybridization conditions to those mentioned above, by appropriately selecting salt concentration (e.g., SSC dilution ratio), temperature, and various other conditions including concentrations of surfactant (e.g., NP-40) and formamide, and pH.

In addition to the in situ hybridization, other examples of the method for detecting a genomic DNA encoding the KIF5B-RET fusion polypeptide using the polynucleotide noted above in (a) or (b) include Southern blotting, Northern blotting and dot blotting. According to these methods, the KIF5B-RET fusion gene is detected by hybridizing the polynucleotide noted above in (a) or (b) to a membrane in which a nucleic acid extract from the foregoing biological sample is transcribed. In the case of using the polynucleotide noted above in (a), if the polynucleotide that hybridizes to a polynucleotide encoding KIF5B protein and the polynucleotide that hybridizes to a polynucleotide encoding RET protein recognize the same band developed in the membrane, then it can be determined that a genomic DNA encoding the KIF5B-RET fusion polypeptide has been detected successfully.

Additional examples of the method for detecting a genomic DNA encoding the KIF5B-RET fusion polypeptide using the polynucleotide noted above in (b) include genome microarray analysis and DNA microarray analysis. According to these methods, the genomic DNA is detected by preparing an array in which the polynucleotide noted above in (b) is immobilized on a substrate and bringing the foregoing biological sample into contact with the polynucleotide immobilized on the array.

In the process of PCR or sequencing, the polynucleotide noted below in (c) can be used to specifically amplify part or all of the KIF5B-RET fusion polynucleotide using DNA (genomic DNA, cDNA) or RNA prepared from the foregoing biological sample as a template:

(c) polynucleotides that are a pair of primers designed to sandwich a point of fusion between a polynucleotide encoding KIF5B protein and a polynucleotide encoding RET protein.

The "polynucleotides that are a pair of primers" refers to a primer set designed such that in the nucleotide sequence of the foregoing fusion polynucleotide or the like to be targeted, one of the primers hybridizes to a polynucleotide encoding KIF5B protein and the other primer hybridizes to a polynucleotide encoding RET protein. These polynucleotides have a length of generally 15-100 nucleotides, preferably 17-30 nucleotides.

The polynucleotide noted above in (c) according to the present invention is, in terms of the accuracy and sensitivity of PCR detection, preferably a sequence complementary to the nucleotide sequence of said fusion polynucleotide which is located not more than 5000 nucleotides away from the point of fusion between a polynucleotide encoding KIF5B protein and a polynucleotide encoding RET protein.

The "polynucleotides that are a pair of primers" can be designed by a known method as appropriate based on the nucleotide sequence of the KIF5B-RET fusion polynucleotide or the like to be targeted. Exemplary known methods include a method using the Primer Express® software (ABI).

Preferred examples of the "polynucleotides that are a pair of primers" include primer sets each consisting of a primer selected from the group consisting of KIF5B-RET-F1, KIF5B-int15-F1, KIF5B-int15-F2, KIF5B-ex16-F1, KIF5B-ex23-F1, KIF5B-ex24-F1, KIF5B-F-orf2438, and KIF5B-int15-F3.5, and a primer selected from the group consisting of KIF5B-RET-R1, RET-int11-R3, RET-int7-R1, RET-int11-R0.5, RET-int11-R1, RET-int7-R2, and RET-R-orf2364, and more preferably primer sets of KIF5B-RET-F1 and KIF5B-RET-R1, KIF5B-int15-F1 and KIF5B-RET-R1, KIF5B-int15-F2 and RET-int11-R3, KIF5B-ex16-F1 and KIF5B-RET-R1, KIF5B-ex23-F1 and KIF5B-RET-R1, and KIF5B-ex24-F1 and RET-int7-R1. As for the sequences of these primers and the positions of the genes to which they are to hybridize, reference should be made to Table 1 and SEQUENCE LISTING given below.

In the present invention, the method for detecting a translation product of the KIF5B-RET fusion polynucleotide can be exemplified by immunostaining, Western blotting, ELISA, flow cytometry, immunoprecipitation, and antibody array analysis. These methods use an antibody binding to the KIF5B-RET fusion polypeptide. Examples of such an antibody include an antibody specific to a polypeptide containing a point of fusion between KIF5B protein and RET protein (hereinafter also referred to as the "fusion point-specific antibody"), an antibody binding to a polypeptide consisting of the region of RET protein which is located away from the fusion point toward the C terminal (hereinafter also referred to as the "RET-C terminal antibody"), and an antibody binding to a polypeptide consisting of the region of KIF5B protein which is located away from the fusion point toward the N terminal (hereinafter also referred to as the "KIF5B-N terminal antibody"). As referred to herein, the "fusion point-specific antibody" means an antibody that specifically binds to the polypeptide containing said fusion point but does not bind to either wild-type (normal) KIF5B protein or wild-type (normal) RET protein.

The KIF5B-RET fusion polypeptide can be detected by the fusion point-specific antibody or a combination of the RET-C terminal antibody and the KIF5B-N terminal antibody. However, since little expression of RET protein is detected in, for example, normal pneumocytes, the presence of the KIF5B-RET fusion polypeptide in LADC tissues can be detected even by using the RET-C terminal antibody alone in immunostaining.

The "antibody binding to the KIF5B-RET fusion polypeptide" can be prepared by those skilled in the art through selection of a known method as appropriate. Examples of such a known method include: a method in which the polypeptide comprising the C-terminal moiety of RET protein, the KIF5B-RET fusion polypeptide, the polypeptide comprising the N-terminal moiety of KIF5B protein, and/or the like are inoculated into immune animals, the immune systems of the animals are activated, and then the serums (polyclonal antibodies) of the animals are collected; as well as monoclonal antibody preparation methods such as hybridoma method, recombinant DNA method, and phage display method. If an antibody having a labeling agent attached thereto is used, the target protein can be detected directly by detecting this label. The labeling agent is not particularly limited as long as it is capable of binding to an antibody and is detectable, and examples include peroxidase, β-D-galactosidase, microperoxidase, horseradish peroxidase (HRP), fluorescein isothiocyanate (FITC), rhodamine isothiocyanate (RITC), alkaline phosphatase, biotin, and radioactive materials. In addition to the direct detection of the target protein using the antibody having a labeling agent attached thereto, the target protein can also be detected indirectly using a secondary antibody having a labeling agent attached thereto, Protein G or A, or the like.

If the presence of the KIF5B-RET fusion polynucleotide is detected in a sample isolated from a patient according to such a method as described above, the patient will be determined to be the one in whom a cancer treatment with a RET tyrosine kinase inhibitor is highly effective. If the presence of the KIF5B-RET fusion polynucleotide is not detected, the patient will be determined to be the one in whom a cancer treatment with a RET tyrosine kinase inhibitor is less effective.

<Agent for Determining the Effectiveness of a Cancer Treatment with a RET Tyrosine Kinase Inhibitor>

As described above, the polynucleotide(s) that is any one of the polynucleotides noted below in (a) to (c), which have a chain length of at least 15 nucleotides, can be used advantageously for detecting the presence or absence of the KIF5B-RET fusion polynucleotide:

(a) a polynucleotide that is at least one probe selected from the group consisting of a probe that hybridizes to a polynucleotide encoding KIF5B protein and a probe that hybridizes to a polynucleotide encoding RET protein;

(b) a polynucleotide that is a probe that hybridizes to a point of fusion between a polynucleotide encoding KIF5B protein and a polynucleotide encoding RET protein; and (c) polynucleotides that are a pair of primers designed to sandwich a point of fusion between a polynucleotide encoding KIF5B protein and a polynucleotide encoding RET protein.

Therefore, the present invention also provides an agent for determining the effectiveness of a cancer treatment with a RET tyrosine kinase inhibitor, the agent which comprises any of these polynucleotides.

These polynucleotides each have a nucleotide sequence complementary to a particular nucleotide sequence of the target gene. As referred to herein, the term "complementary" may not necessarily refer to perfect complementarity as long as hybridization is achieved. These polynucleotides have generally at least 80% homology, preferably at least 90% homology, more preferably at least 95% homology, and particularly preferably at least 100% homology with such a particular nucleotide sequence.

The polynucleotides (a) to (c) may be a DNA or a RNA, or alternatively may be such that part or all of the nucleotides are substituted by an artificial nucleic acid such as PNA (polyamide nucleic acid: a peptide nucleic acid), LNA™ (Locked Nucleic Acid; a bridged nucleic acid), ENA® (2'-O,4'-C-Ethylene-bridged Nucleic Acid), GNA (glycerol nucleic acid) or TNA (threose nucleic acid).

As described above, the antibody binding to the KIF5B-RET fusion polypeptide can be used advantageously for detecting a translation product of the KIF5B-RET fusion polynucleotide. Therefore, the present invention also provides an agent for determining the effectiveness of a cancer treatment with a RET tyrosine kinase inhibitor, the agent which comprises said antibody.

The agent of the present invention can contain not only the foregoing substance (e.g., polynucleotide, antibody) as an active ingredient but also other pharmacologically acceptable components. Such other components include buffer agents, emulsifying agents, suspending agents, stabilizing agents, antiseptic agents, and physiological saline. As buffer agents, there can be used phosphates, citrates, acetates and the like. As emulsifying agents, there can be used gum arabic, sodium alginate, tragacanth, and the like. As suspending agents, there can be used glyceryl monostearate, aluminum monostearate, methylcellulose, carboxymethyl cellulose, hydroxymethyl cellulose, sodium lauryl sulfate, and the like. As stabilizing agents, there can be used propylene glycol, diethylene sulfite, ascorbic acid, and the like. As antiseptic agents, there can be used sodium azide, benzalkonium chloride, paraoxybenzoic acid, chlorobutanol, and the like.

The preparation comprising the polynucleotide or the antibody may also be combined with other preparations such as a substrate required for detecting a label attached to the polynucleotide or the antibody, a positive control (e.g., KIF5B-RET fusion polynucleotide, KIF5B-RET fusion polypeptide, or cells bearing the same), a negative control, a counterstaining reagent for use for in situ hybridization or the like (e.g., DAPI), a molecule required for antibody detection (e.g., secondary antibody, Protein G, Protein A), and a buffer solution for use in sample dilution or washing, whereby a kit for use in the method of the present invention can be provided. The inventive kit can contain instructions for use thereof. The present invention also provides the foregoing kit for use in the method of this invention.

<Method for Treatment of Cancer, and Therapeutic Agent for Cancer>

As described above, if the presence of the KIF5B-RET fusion polynucleotide is detected in a patient by the method of the present invention, a cancer treatment with a RET tyrosine kinase inhibitor is considered to be highly effective in the patient. Thus, efficient treatments can be performed by administering RET tyrosine kinase inhibitors selectively to those cancer patients who carry the fusion gene between the KIF5B gene and the RET gene. Therefore, the present invention provides a method for treatment of cancer, comprising the step of administering a RET tyrosine kinase inhibitor to a patient in whom a cancer treatment with the RET tyrosine kinase inhibitor has been determined to be highly effective by the foregoing method of this invention.

Further, the present invention provides a therapeutic agent for cancer, comprising a RET tyrosine kinase inhibitor as an active ingredient, the agent which is to be administered to a patient in whom a cancer treatment with the RET tyrosine kinase inhibitor has been determined to be highly effective by the foregoing method of this invention.

As described above, the "RET tyrosine kinase inhibitor" is not particularly limited as long as it is a substance capable of directly or indirectly suppressing the ability of RET tyrosine kinase. The inhibitor may also be a substance that inhibits other tyrosine kinases as long as it is capable of inhibiting RET tyrosine kinase. Examples of known RET tyrosine kinase inhibitors that can be applied to the present invention include 4-(4-bromo-2-fluoroanilino)-6-methoxy-7-(1-methylpiperidin-4-ylmethoxy)quinazoline (generic name: Vandetanib; compound targeting VEGFR, EGFR, and RET), 4-[4-[3-[4-chloro-3-(trifluoromethyl)phenyl]ureido]phenoxy]-N-methylpyridin-2-carboxamide (generic name: Sorafenib; compound targeting BRAF, RET, and the like), N-[2-(diethylamino)ethyl]-5-[(Z)-(5-fluoro-2-oxo-1,2-dihydro-3H-indol-3-ylidene)methyl]-2,4-dimethyl-1H-pyrrole-3-carboxamide mono[(2S)-2-hydroxysuccinate] (generic name: Sunitinib; compound targeting PDGFR, VEGFR, RET, and the like), N-(3,3-dimethylindolin-6-yl)-2-(pyridin-4-ylmethylamino)nicotinamide (generic name: Motesanib; compound targeting PDGFR, VEGFR, RET, and the like), and XL184/Cabozantinib (compound targeting VEGFR, MET, RET, and the like).

The method for administering a RET tyrosine kinase inhibitor to a patient is selected as appropriate depending on the type of the inhibitor and the type of cancer, and examples of the administration method that can be adopted include oral, intravenous, intraperitoneal, transdermal, intramuscular, intratracheal (aerosol), rectal, intravaginal and other administrations.

EXAMPLES

On the pages that follow, the present invention will be more specifically described based on Examples, but this invention is not limited to the examples given below.

<Samples>

The Japanese cohort was comprised of 319 LADC patients undergoing surgical resection at the National Cancer Center Hospital between 1997 and 2008. The USA (UMD) cohort was recruited from hospitals in the Metropolitan Baltimore area between 1987 and 2009. All tumors were pathologically diagnosed according to the TNM classification of malignant tumors.

Total RNA was extracted from grossly dissected, snap-frozen tissue samples using a TRIzol reagent according to the manufacturer's instructions and was examined for quality using a model 2100 bioanalyzer (Agilent Technologies). As a result, all samples showed RIN (RNA integrity number) values greater than 6. Genomic DNA was also extracted from the tissue samples using a QIAamp® DNA Mini kit (Qiagen). The study was conducted with the approval by the institutional review boards of the institutions involved in the present study.

<RNA Sequencing> cDNA libraries for RNA sequencing were prepared using the mRNA-Seq sample preparation kit (Illumina) according to the manufacturer's standard protocol. Briefly, poly-A (+) RNA was purified from 2 μg of total RNA and fragmented by heating at 94° C. for 5 minutes in a fragmentation buffer, before being used for double-stranded cDNA synthesis. After the resulting double-stranded cDNA was ligated to the PE adapter DNA, a fraction of 250-300 bp (insert DNA size: 150-200 bp) was gel-purified and amplified with 15 cycles of PCR. The thus-created libraries were subjected to paired-end sequencing of 50-bp reads on the Genome Analyzer IIx (GAIIx) sequencer (Illumina).

<Detection of Fusion Transcripts>

Detection of fusion transcripts was performed by a modified version of the method described in Totoki Y, et al., Nat Genet., May 2011, Vol. 43, No. 5, p. 464-469. Briefly, paired-end reads with the same nucleotide sequences were first removed, since they were deduced to be generated during the PCR amplification process. Next, the remaining paired-end reads were mapped on human RNA sequences deposited in the RefSeq database (File: human.rna.fna from ftp://ftp.ncbi.nih.gov/refseq, Date: Sep. 20, 2010) using the BOWTIE program (version 0.12.5) under the condition that two or less nucleotide mismatches are allowed. "Proper" paired-end reads were removed, in which both reads were mapped on the same RNA sequences with proper spacing and orientation. Then, those reads with multiple hits on several genomic loci were removed, and the remaining reads were assembled into "clusters."

Then, "paired clusters" which indicate the presence of fusion transcripts were selected under the following analysis conditions:

(I) "clusters" which consist of reads aligned within the distance corresponding to the maximum insert sequence length are separately constructed from the forward and reverse alignments (in the case where the end positions of two reads are not apart from each other by more than the distance corresponding to the maximum insert sequence length, these two reads are allocated to the same cluster);

(II) clusters in which the distance between the leftmost and rightmost reads are greater than the insert sequence length are discarded;

(III) in the case where one end sequence of paired-end reads is allocated in the "forward cluster" and the other end sequence is allocated in the "reverse cluster," those paired-end reads are selected (the "forward cluster" and "reverse cluster" are collectively referred to as the "paired clusters");

(IV) those paired clusters which included at least one paired-end read perfectly matched to the human reference RNA sequence are selected; and (V) paired genes that have been mis-assembled due to their variations in nucleotide are removed. For this purpose, paired-end reads contained in paired clusters were aligned with human reference RNA sequences using the BLASTN program. Then, in the case where one end sequence of paired genes was aligned with a region of paired clusters and the other end sequence was aligned with the same RNA sequence with proper spacing and orientation, those paired genes were removed. An expectation value of 1000 was used as a cutoff value.

Then, those paired genes for which more than 20 paired-end reads were obtained in an LADC sample, and which did not appear in any of three non-cancerous lung tissues were picked up. Paired clusters that were mapped within one gene region or a neighboring gene region were excluded from further investigation, because there was a possibility that they might be alternatively spliced or read-through transcripts that have not been deposited in the RefSeq database. Junction reads encompassing the fusion boundaries were searched using the MapSplice (version 1.14.1) software. In the process, a read cluster region and two genomic DNA sequences each consisting of the 300 bp region neighboring thereto were joined together into one DNA sequence, and the resulting DNA sequence was searched for junction reads using the MapSplice software.

<RT-PCR, Genomic PCR, and Sanger Sequencing>

Total RNA (500 ng) was reverse-transcribed using Superscript® III Reverse Transcriptase (Invitrogen). The resulting cDNA (corresponding to 10 ng total RNA) or 10 ng genomic DNA was subjected to PCR amplification using KAPA Taq DNA Polymerase (KAPA Biosystems). The reactions were effected in a thermal cycler under the following conditions: 40 cycles of reactions at 95° C. for 30 seconds, at 60° C. for 30 seconds, and at 72° C. for 2 minutes, followed by a final extension reaction at 72° C. for 10 minutes. The gene encoding glyceraldehyde-3-phosphate dehydrogenase (GAPDH) was amplified for estimating the efficiency of cDNA synthesis. Further, the PCR products were directly sequenced in both directions using a BigDye Terminator kit and an ABI 3130×1 DNA Sequencer (Applied Biosystems). The primers used in the present study are shown in Table 1.

TABLE 1

| No. | Primer name | Location | Sequence | SEQ ID NO. | Use |
|---|---|---|---|---|---|
| KIF5B-RET fusion | | | | | |
| 1 | KIF5B-RET-F1 | KIF5B exon 15 | AGGAAATGACCAACCACCAG | 13 | RT-PCR and sequencing |
| 2 | KIF5B-RET-R1 | RET exon 12 | TCCAAATTCGCCTTCTCCTA | 14 | RT-PCR and genomic PCR |
| 3 | KIF5B-int15-F1 | KIF5B introit 15 | CCATAAGTGAAATGATTGGAAC | 15 | Genomic PCR |
| 4 | KIF5B-int15-F2 | KIF5B intron 15 | GATTTGTATGTTGCAGTAGCTG | 16 | Genomic PCR |
| 5 | KIF5B-ex16-F1 | KIF5B exon 16 | GGAGTTAGCAGCATGTCAGC | 17 | Genomic PCR and sequencing |
| 6 | KIF5B-ex23-F1 | KIF5B exon 23 | GCTCACTAAAGTGCACAAACAG | 18 | Genomic PCR and sequencing |
| 7 | KIF5B-ex24-F1 | KIF5B exon 24 | GAAGAGGGCATTCTGCACAG | 19 | Genomic PCR |
| 8 | RET-int11-R3 | RET intron 11 | GGAGGCTCCAGGATACTCGG | 20 | Genomic PCR |
| 9 | RET-int7-R1 | RET intron 7-exon 8 | CCTCCTCGGCCACATCTG | 21 | Genomic PCR |
| 10 | KIF5B-F-orf2438 | KIF5B exon 22-23 | AGAGTGCTGAGATTGATTCTG | 22 | Sequencing |
| 11 | KIF5B-int15-F3.5 | KIF5B intron 15 | CCCGAGTAGCTAGGATTACA | 23 | Sequencing |
| 12 | RET-int11-R0.5 | RET intron 11 | ATGACAGGTGTGGTCACAGC | 24 | Sequencing |
| 13 | RET-int11-R1 | RET intron 11 | TATCCACACATTGGGCCCAC | 25 | Sequencing |
| 14 | RET-int7-R2 | RET intron 7 | ATGGCAGCTGTGTCAGCATG | 26 | Sequencing |
| RET expression | | | | | |
| 1 | RET-F-orf2154 | RET exon 12 | ATTCCCTCGGAAGAACTTGG | 27 | RT-PCR |
| 2 | RET-R-orf2364 | RET exon 13 | GATGACATGTGGGTGGTTGA | 28 | RT-PCR |

<Analysis of EGFR, KRAS, and ALK Mutations>

Genomic DNAs from all of the LADC tissues were analyzed for somatic mutations in the EGFR and KRAS genes using the high-resolution melting (HRM) method described in Takano, T., et al., *J Clin Oncol.*, 2005, Vol. 23, p. 6829-6837. Total RNAs from the same tissues were examined for expression of ALK/EML4 or ALK/KIF5B fusion transcripts using a multiplex reverse transcription PCR method.

<Genome Copy Number Analysis>

The LADC samples were determined for genome copy number using GeneChip® Human Mapping 250-K SNP arrays (Affymetrix) and the Copy Number Analyzer for Affymetrix GeneChip Mapping arrays (CNAG) software (refer to Nannya, Y., et al., *Cancer Res.*, 2005, Vol. 65, p. 6071-6079), as described in the previous report made by the present inventors (Iwakawa, R., et al., MYC Amplification as a Prognostic Marker of Early Stage Lung Adenocarcinoma Identified by Whole Genome Copy Number Analysis, *Clin Cancer Res.*, 10 Dec. 2010, online)

<Microarray Analysis and Data Processing>

A total of 228 cases were subjected to expression profiling. Total RNA (100 ng) was labeled using a 5× MEGAscript T7 kit and analyzed using Affymetrix U133 Plus 2.0 arrays. The obtained data were normalized using the MASS algorithm and the mean expression level of 54,4675 probes was adjusted to 1000 for each sample.

<Immunohistochemical Analysis>

Paraffin blocks were sliced into 4 μm thick sections and affixed to silane-coated slides. After the slices were deparaffinized and hydrophilized in a xylene-alcohol series, the slides were treated with 3% hydrogen peroxide in solution for 20 minutes to block endogenous peroxidase, and were then washed with deionized water for 2-3 minutes. The slides were subjected to antigen retrieval by heating them in a targeted retrieval solution at 95° C. for 40 minutes. After washing, the slides were reacted with 5% normal animal serum for 10 minutes to block any nonspecific reactions, and were then incubated with the primary antibodies against RET (dilution 1:250, clone 3454_1) and TTF1 (dilution 1:100, clone 8G7G3/1) at room temperature for an hour. Immunoreactions were detected using the Envision-Plus system for TTF1 and EnVision FLEX plus LINKER for RET. After washing, the reactions were visualized by using a 3,3'-diaminobenzidine solution for 5 minutes, washing with flowing water, and counterstaining with hematoxylin. Nuclear staining of more than 10% of tumor cells was considered positive for TTF1, and cytoplasmic staining was considered positive for RET.

<Fluorescent In Situ Hybridization (FISH)>

On the first day, slices were deparaffinized, hydrophilized, and air-dried, as in the process of immunostaining. Thereafter, the slices were allowed to stand in 0.2 N hydrochloric acid at room temperature for 20 minutes, in purified water at room temperature for 3 minutes, and then in a wash buffer (2×SSC) at room temperature for 3 minutes. After standing in a pretreatment solution at 85° C. for 30 minutes, the slices were washed with a 2×SSC wash buffer twice. Next, the slices were allowed to stand in a protease solution at 37° C. for 60 minutes and subjected to enzymatic treatment, followed by washing with a wash buffer (2×SSC) twice. Then, the slices were allowed to stand in 10% neutral buffered formalin at room temperature for 10 minutes to effect fixation again, and they were washed with a wash buffer (2×SSC) at room temperature twice. Thereafter, the slices were dehydrated in alcohol series and then air-dried.

Detection of a fusion gene between the KIF5B gene and the RET gene was made using the undermentioned probe set designed to detect a split produced by formation of a fusion gene between the KIF5B gene and the RET gene, which is between the portion consisting of a region upstream from the coding region for the kinase domain of the RET gene toward the 5' terminal, and the portion consisting of said coding region and a region downstream from said coding region toward the 3' terminal:

5' RET probe 1: A group of TexRed-labeled probes having a chain length of 100-1000 nucleotides, which encompasses the BAC clone DNA GSP1506F09 (GSP Laboratory, Inc.); and 3' RET probe 1: A group of TexRed-labeled probes having a chain length of 100-1000 nucleotides, which encompasses the FITC-labeled BAC clone DNA GSP1877H08, GSP1018G02, GSP1070C12, GSP0369G08 or GSP0075D03 (GSP Laboratory, Inc.).

These probes were labeled by nick translation. The positions in the genome to which these probes are to hybridize are shown in the lower part of FIG. 11.

Next, 10 μL of a mixture of the foregoing DNA probes was added to the foregoing formalin-fixed slices, and cover glasses were placed and sealed with a paper adhesive. Then, hybridization was carried out using a hybridizer (product name: Thermo Brite®; Abbott Japan) by incubating the slides at 75° C. for 5 minutes and then at 37° C. for 72-96 hours.

After completion of the incubation, the paper adhesive was removed, and the samples with their cover glasses placed thereon were put in a post-hybridization wash buffer (2×SSC with 0.3% NP-40; pH 7-7.5) at room temperature and left to stand for 5 minutes to remove the cover glasses. The samples were put in a post-hybridization wash buffer (2×SSC with 0.3% NP-40; pH 7-7.5) heated to 72±1° C. and allowed to stand for 30 seconds to 1 minute.

Next, the samples were transferred to Coplin jars that contain a 2×SSC wash buffer at room temperature and which were light-shielded with aluminum foil. Then, 10 μL of DAPI was added to the slide glasses to effect counterstaining, and cover glasses were placed and fixed with manicure.

Determination was made under a fluorescence microscope; the numbers of fusion, split and single signals among red RET-derived signals and green centromere 10-derived signals were respectively counted for 50 tumor cells.

Example 1

First, in order to identify new chimeric fusion transcripts as potential targets for therapy, thirty LADC specimens and three associated non-cancerous tissues were subjected to whole-transcriptome sequencing (RNA sequencing; refer to Meyerson, M., et al., *Nat Rev Genet*, 2010, Vol. 11, p. 685-696). These 30 LADC specimens consisted of two with EML4-ALK fusions, two with EGFR mutations, two with KRAS mutations, and twenty-four without EGFR/KRAS/ALK mutations (refer to Table 2).

TABLE 2

| No. | Sample | Tumor or normal | Sex | Gene mutation | Age | Smoking (Pack-years) | Pathological stage | No. total read | Gene fusion (No. paired-end reads/junction reads) |
|---|---|---|---|---|---|---|---|---|---|
| 1 | BR0009 | Tumor | Male | ALK | 30 | Ever-smoker (30) | IIB | 30,067,759 | EML4-ALK (91/64) |
| 2 | BR0052* | Tumor | Female | ALK | 38 | Ever-smoker (7) | IIA | 27,841,176 | EML4-ALK (60/67) |
| 3 | BR0003 | Tumor | Female | EGFR | 60 | Never-smoker | IIB | 33,358,341 | TMEM209-DPP6 (61/16), ZNP862-WDR91 (24/22) |
| 4 | BR0044 | Tumor | Male | EGFR | 68 | Ever-smoker (10) | IIB | 32,262,234 | |
| 5 | BR0005 | Tumor | Male | KRAS | 59 | Ever-smoker (62) | IIB | 23,297,267 | |
| 6 | BR0016 | Tumor | Female | KRAS | 75 | Never-smoker | IIB | 27,188,879 | |
| 7 | BR0001 | Tumor | Male | None | 68 | Ever-smoker (86) | IB | 23,467,018 | MTAP-CDKN2BAS (23/37) |
| 8 | BR0004 | Tumor | Male | None | 62 | Ever-smoker (46) | IIB | 33,540,967 | |
| 9 | BR0006 | Tumor | Female | None | 62 | Ever-smoker (38) | IB | 21,386,586 | |
| 10 | BR0012 | Tumor | Male | None | 65 | Ever-smoker (92) | IIB | 28,465,957 | |
| 11 | BR0013 | Tumor | Female | None | 58 | Never-smoker | IB | 28,740,939 | |
| 12 | BR0014 | Tumor | Male | None | 52 | Ever-smoker (68) | IIB | 21,036,216 | |
| 13 | BR0015 | Tumor | Female | None | 49 | Ever-smoker (20) | IIB | 21,125,603 | |
| 14 | BR0019* | Tumor | Female | None | 54 | Never-smoker | IIB | 28,868,572 | |
| 15 | BR0020 | Tumor | Male | None | 57 | Never-smoker | IIB | 25,404,815 | KIF5B-RET (30/12) |
| 16 | BR0026 | Tumor | Male | None | 58 | Ever-smoker (41) | IIB | 23,458,513 | |
| 17 | BR0027 | Tumor | Male | None | 68 | Ever-smoker (49) | IIA | 22,344,197 | |
| 18 | BR0029 | Tumor | Male | None | 53 | Ever-smoker (70) | IA | 31,534,640 | FAM3C-CADPS2 (21/20) |
| 19 | BR0031 | Tumor | Male | None | 54 | Never-smoker | IA | 32,324,822 | CDC42-TMCO4 (41/28) |
| 20 | BR0032 | Tumor | Female | None | 61 | Never-smoker | IA | 22,093,962 | |
| 21 | BR0033 | Tumor | Male | None | 69 | Ever-smoker (102) | IIB | 29,321,549 | |
| 22 | BR0034 | Tumor | Male | None | 66 | Ever-smoker (45) | IA | 29,069,205 | |
| 23 | BR0035 | Tumor | Male | None | 61 | Ever-smoker (42) | IIB | 25,683,757 | |
| 24 | BR0036* | Tumor | Male | None | 66 | Ever-smoker (37) | IB | 21,790,422 | |
| 25 | BR0037 | Tumor | Male | None | 63 | Ever-smoker (40) | IB | 31,571,318 | |
| 26 | BR0038 | Tumor | Female | None | 47 | Never-smoker | IA | 26,967,632 | |
| 27 | BR0040 | Tumor | Male | None | 69 | Ever-smoker (105) | IIA | 27,417,202 | |
| 28 | BR0041 | Tumor | Male | None | 46 | Ever-smoker (27) | IIB | 29,761,895 | |
| 29 | BR0043 | Tumor | Male | None | 68 | Ever-smoker (48) | IIB | 26,223,934 | |
| 30 | BR0045 | Tumor | Female | None | 64 | Never-smoker | IIB | 24,191,784 | |
| 31 | BR0052 | Normal | Female | — | 38 | Ever-smoker (7) | IIA | 28,563,803 | — |
| 32 | BR0036 | Normal | Male | — | 66 | Ever-smoker (37) | IB | 33,523,557 | — |
| 33 | BR0019 | Normal | Female | — | 54 | Never-smoker | IIB | 29,088,007 | — |

*Corresponding non-cancerous lung tissue RNAs of these cases were also subjected to RNA sequencing.

Then, $2 \times 10^7$ or more paired-end reads obtained by the RNA sequencing were analyzed to perform Sanger sequencing of the reverse transcription (RT)-PCR products. The obtained results are shown in Table 2, FIGS. 1 and 2.

Figure 1:
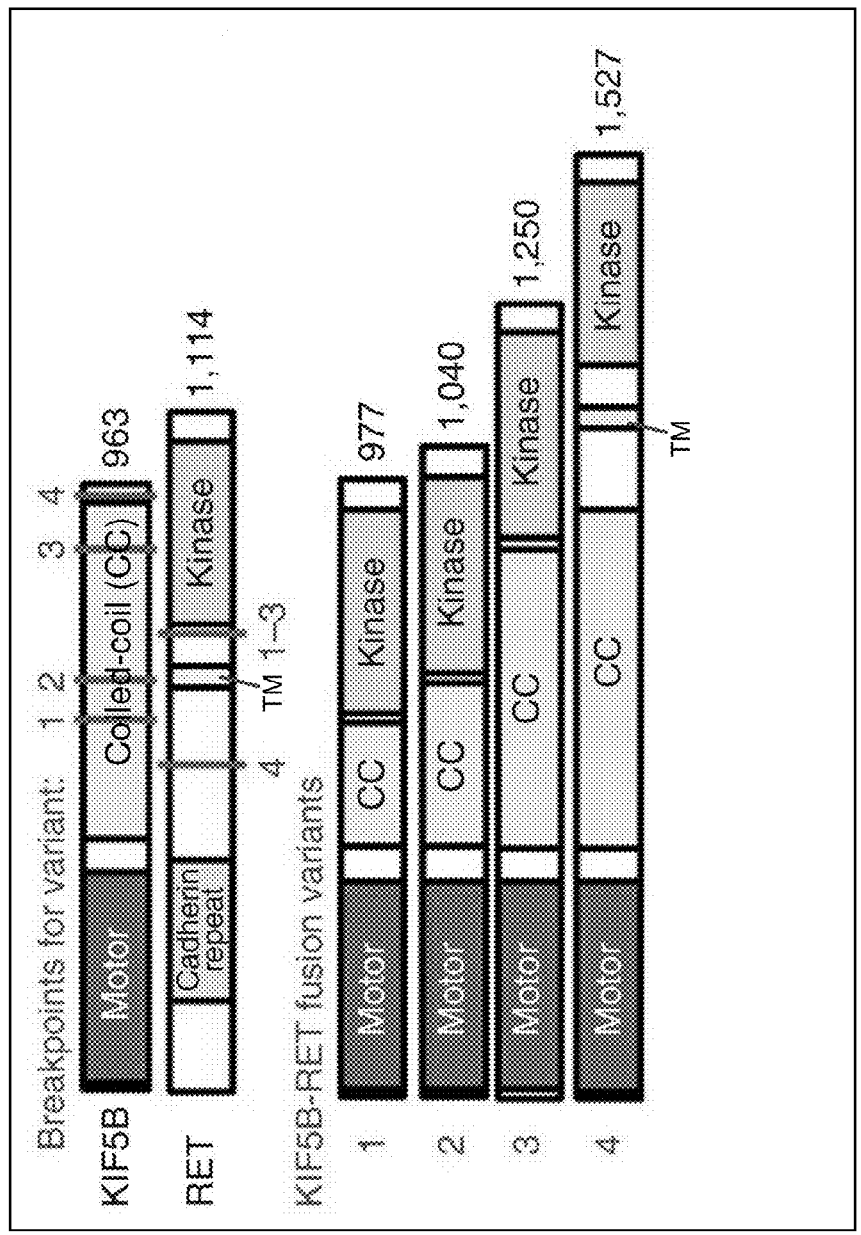
Figure 2:
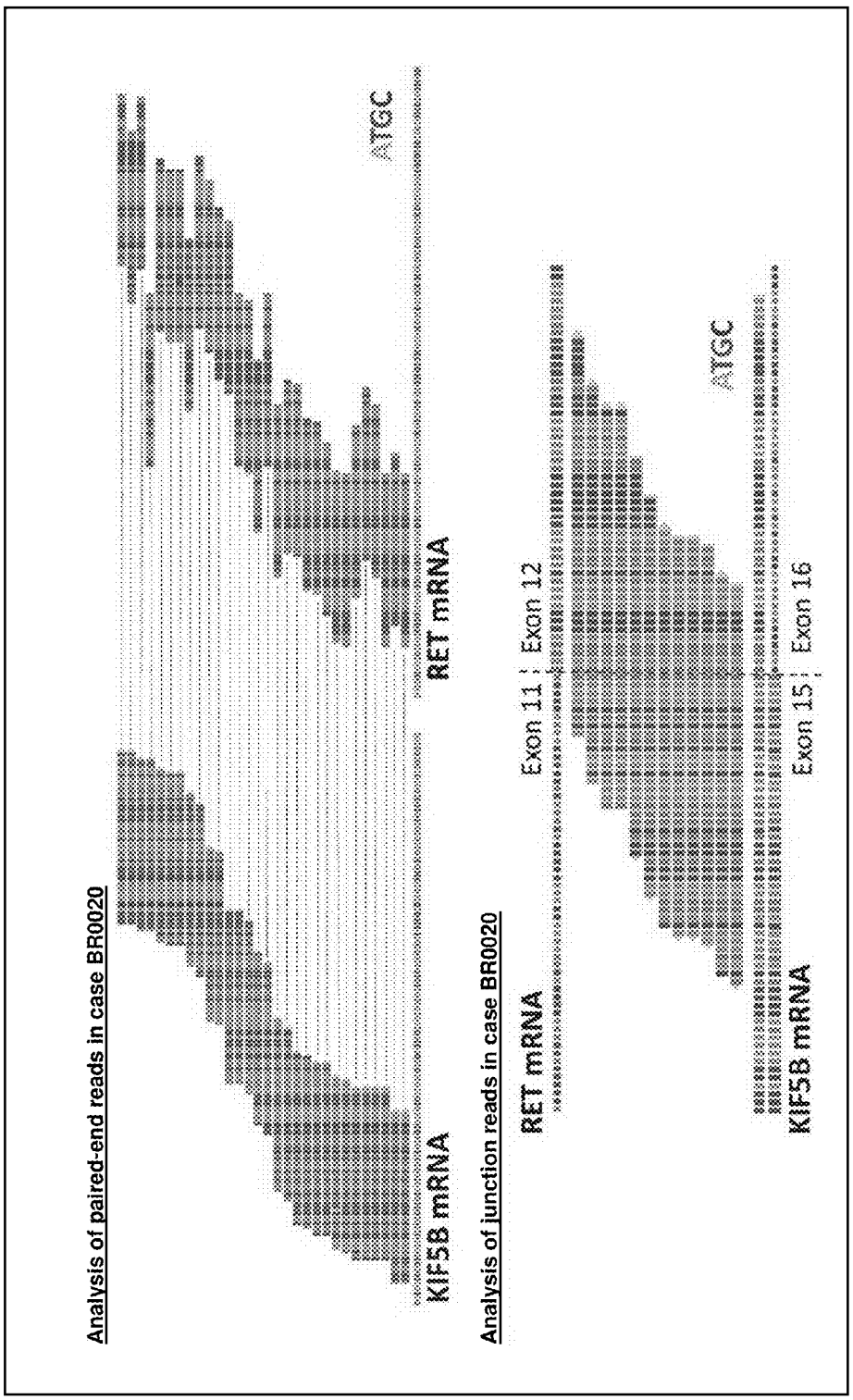

As is evident from the results shown in Table 2, seven fusion transcripts including two transcripts of EML4-ALK were identified; among them, the fusion between the KIF5B gene on chromosome 10p11.2 and the RET gene on chromosome 10q11.2 was detected in case BR0020 (refer to KIF5B-RET variant 1 in FIG. 1, and FIG. 2).

It should be noted that as regards the RET gene, its fusions with other genes than KIF5B had been shown to be driver mutations (responsible mutations) for papillary thyroid cancers (refer to: Mani, R. S., et al., *Nat Rev Genet*, 2010, Vol. 11, p. 819-829; and Wells, S. A., Jr., et al., *Clin Cancer Res*, 2009, Vol. 15, p. 7119-7123). However, no relationship has been found between cancers, including LADC, and KIF5B-RET fusion transcripts; thus, a further analysis was made with a focus on this fusion gene.

Example 2

Next, 319 LADC specimens from Japanese individuals, including 30 that had undergone whole-transcriptome sequencing, were subjected to RT-PCR screening and Sanger sequencing of the PCR products. The obtained results are shown in Table 3, FIGS. 3 and 4.

TABLE 3

| | Japan | | | | | | USA |
|---|---|---|---|---|---|---|---|
| | | Mutation type | | | | | |
| Variable | All (%) | EGFR[a] (%) | KRAS[a] (%) | ALK[b] (%) | RET[b] (%) | None (%) | |
| Total | 319 | 169 | 30 | 11 | 6 | 103 | 80 |
| Age (mean ± SD; years) | 61.7 ± 8.6 | 61.0 ± 7.9 | 62.3 ± 9.1 | 53.5 ± 13.2 | 57.0 ± 15.2 | 63.6 ± 8.2 | 64.1 ± 9.7 |
| Sex | | | | | | | |
| Male (%) | 158 (49.5) | 68 (40.2) | 19 (63.3) | 2 (18.2) | 3 (50.0) | 66 (64.1) | 42 (52.5) |
| Female (%) | 161 (50.5) | 101 (59.8) | 11 (36.7) | 9 (81.8) | 3 (50.0) | 37 (35.9) | 38 (47.5) |
| Smoking habit | | | | | | | |
| Never-smoker (%) | 157 (49.2) | 92 (54.4) | 12 (40.0) | 7 (63.6) | 6 (100.0) | 40 (38.8) | 5 (6.3) |
| Ever-smoker (%) | 162 (50.8) | 77 (45.6) | 18 (60.0) | 4 (36.4) | 0 (0.0) | 63 (61.2) | 73 (91.3) |

[a] Mutations detected by high-resolution melting assay.
[b] Fusions detected by RT-PCR.

Figure 3:
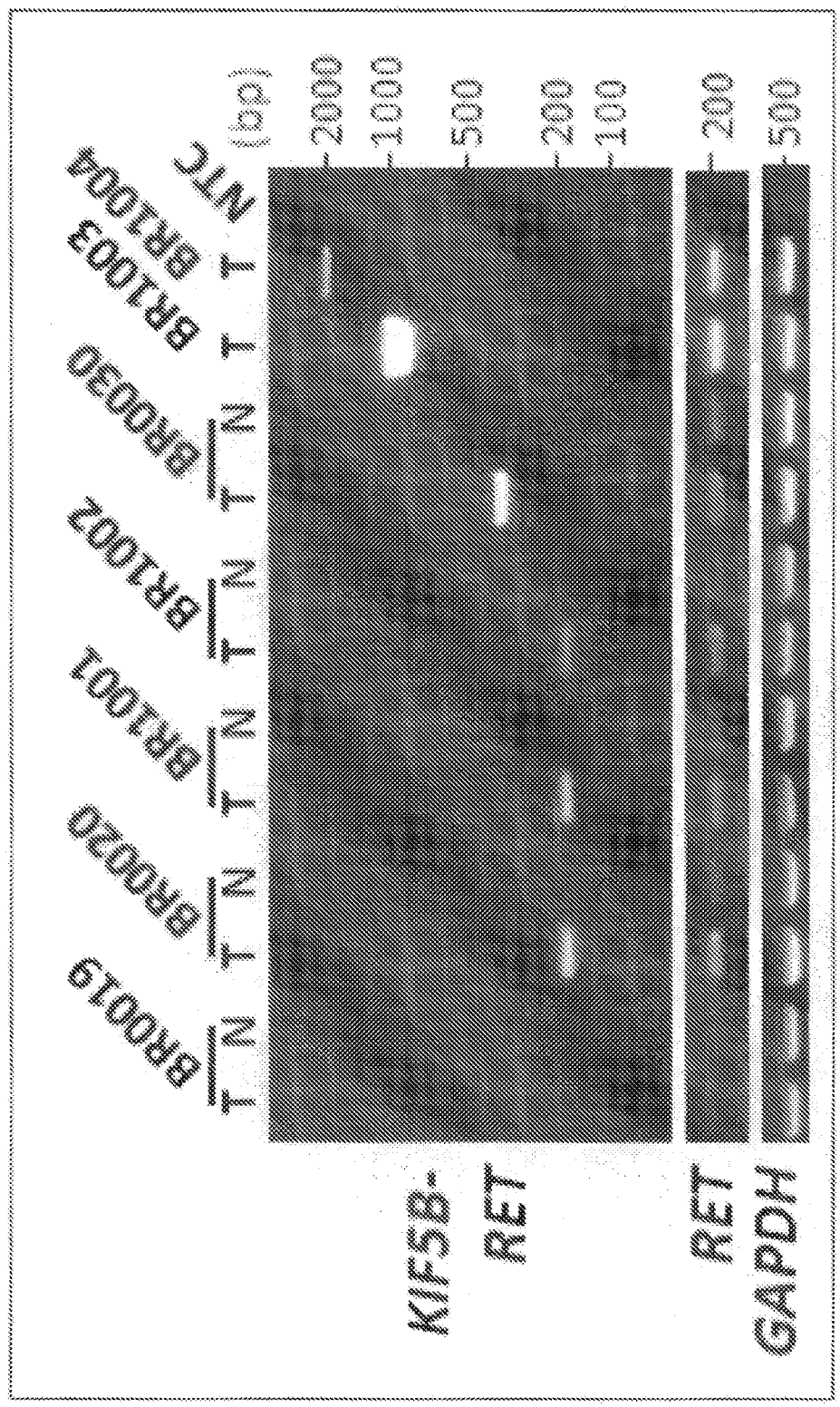
Figure 4:
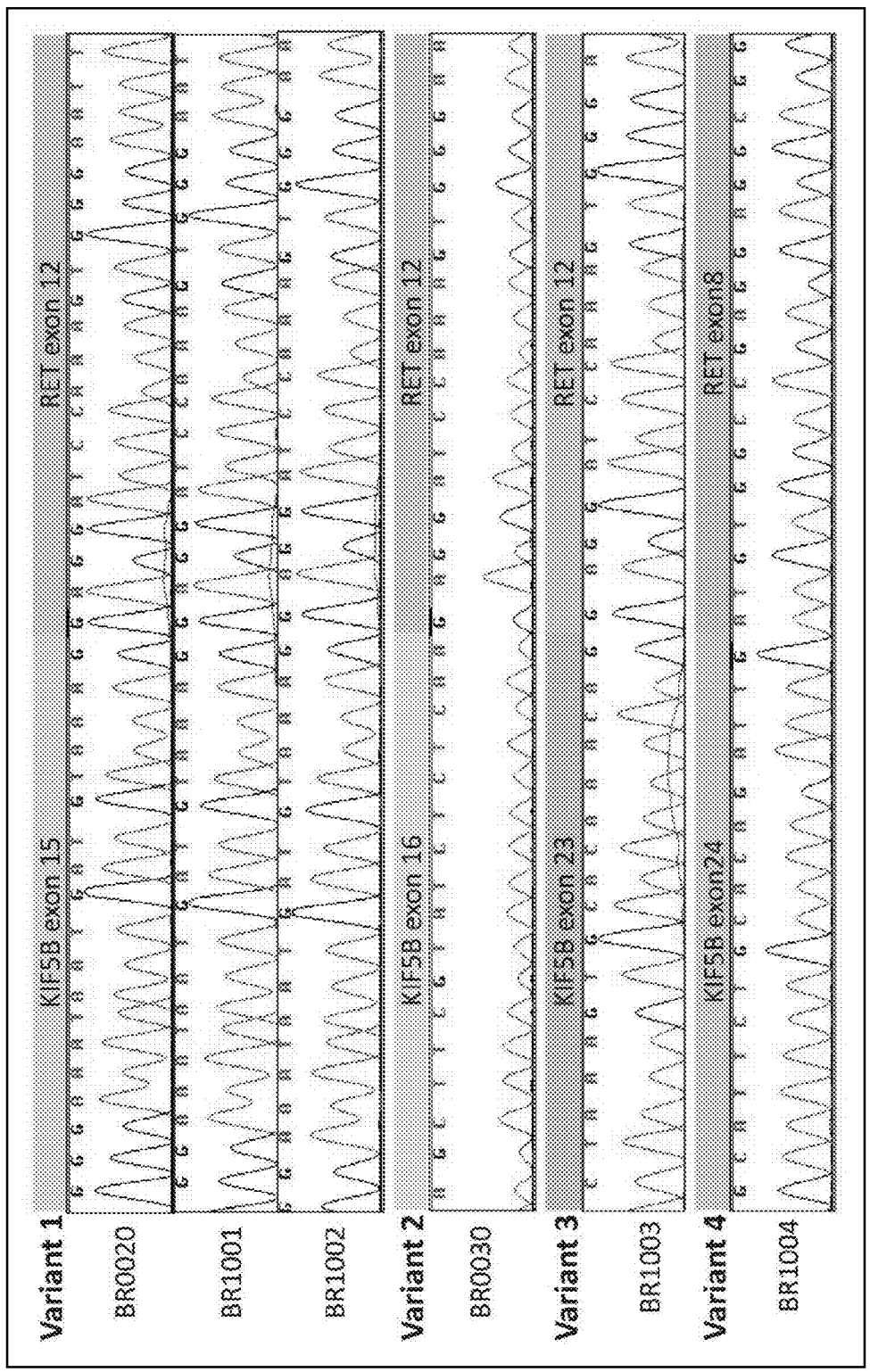

As shown in Table 3, FIGS. 3 and 4, the KIF5B-RET fusion transcripts were found to be expressed in 2.0% (6/319) of the specimens. Also, four variants were identified, all of which were shown to be in-frame. Further, it was found that the proteins encoded by these fusion transcripts contain the KIF5B coiled-coil domain and the RET kinase domain (refer to FIG. 1). The KIF5B coiled-coil domain had been known to function in the homodimerization of KIF5B (Hirokawa, N., *Nat Rev Mol Cell Biol,* 2009, Vol. 10, p. 682-696); thus, it is assumed that the KIF5B-RET protein would undergo homodimerization mediated by the KIF5B coiled-coil domain, leading to constitutive activation of RET kinase activity, as in the cases of the PTC-RET and KIF5B-ALK fusions.

No KIF5B-RET fusion was detected in other main subtypes of lung cancer (squamous cell carcinoma (0/205), small-cell carcinoma (0/20)) or 90 lung cancer cell lines including 40 LADCs. As for these lung cancer cell lines, refer to Blanco, R., et al., *Hum Mutat,* 2009, Vol. 30, p. 1199-1206.

Example 3

Next, six RET fusion positive specimens were subjected to genomic PCR analysis. The obtained results are shown in FIGS. 5-10.

Figure 5:
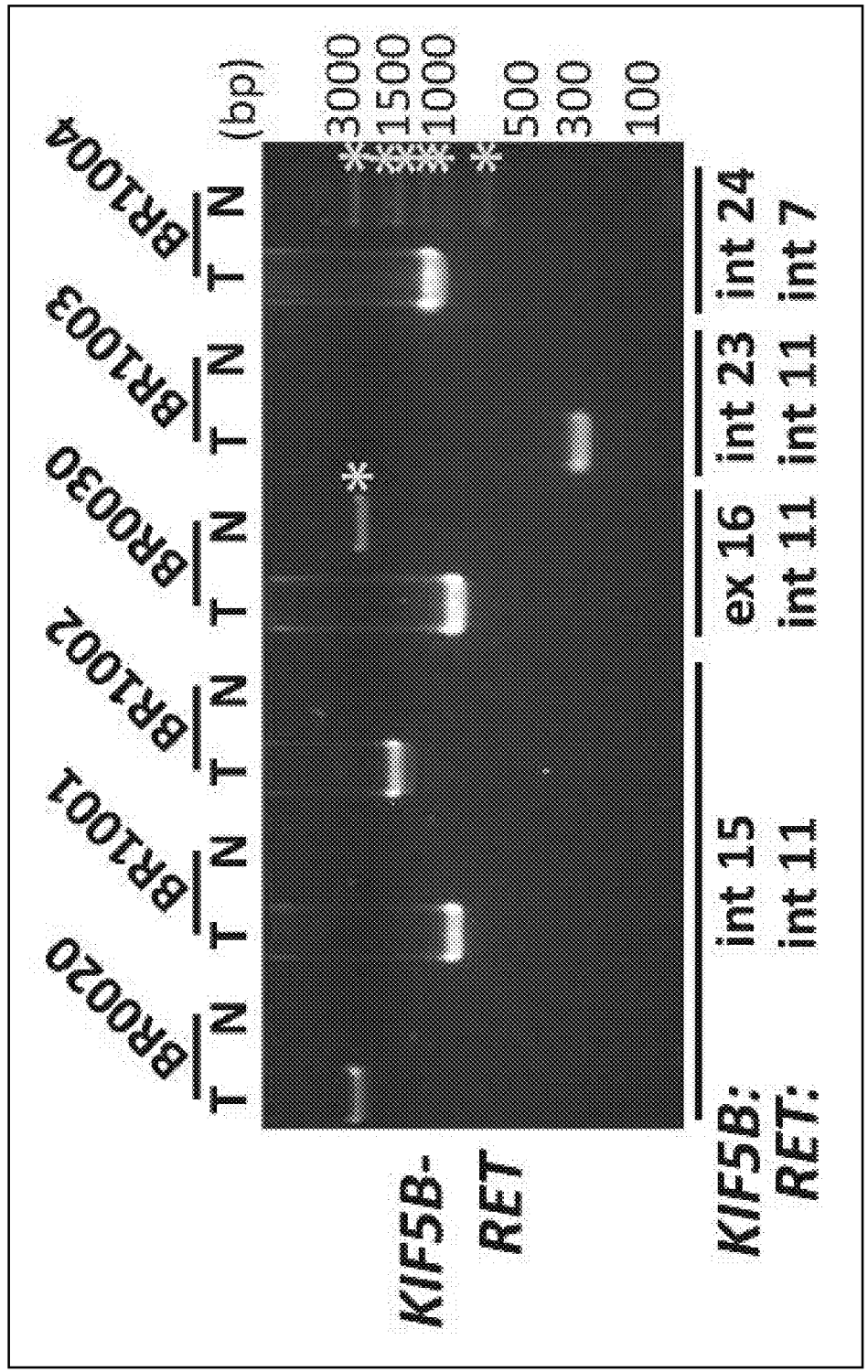

As shown in FIGS. 5-7, KIF5B intron 15, 16 or 24 at human chromosome 10p11.2 and RET intron 7 or 11 at chromosome 10q11.2 were found to be fused together at a somatic level.

Figure 8:
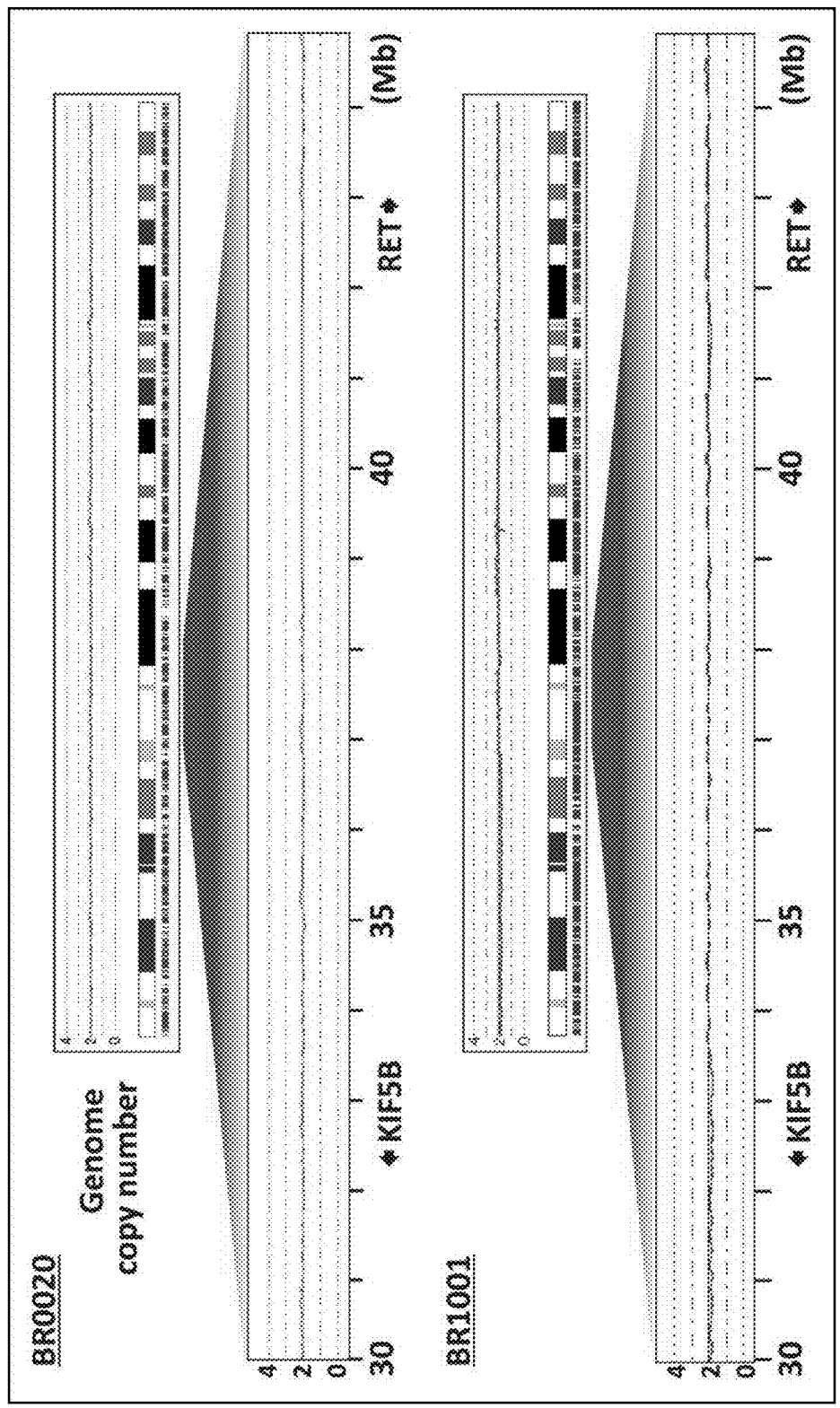
Figure 9:
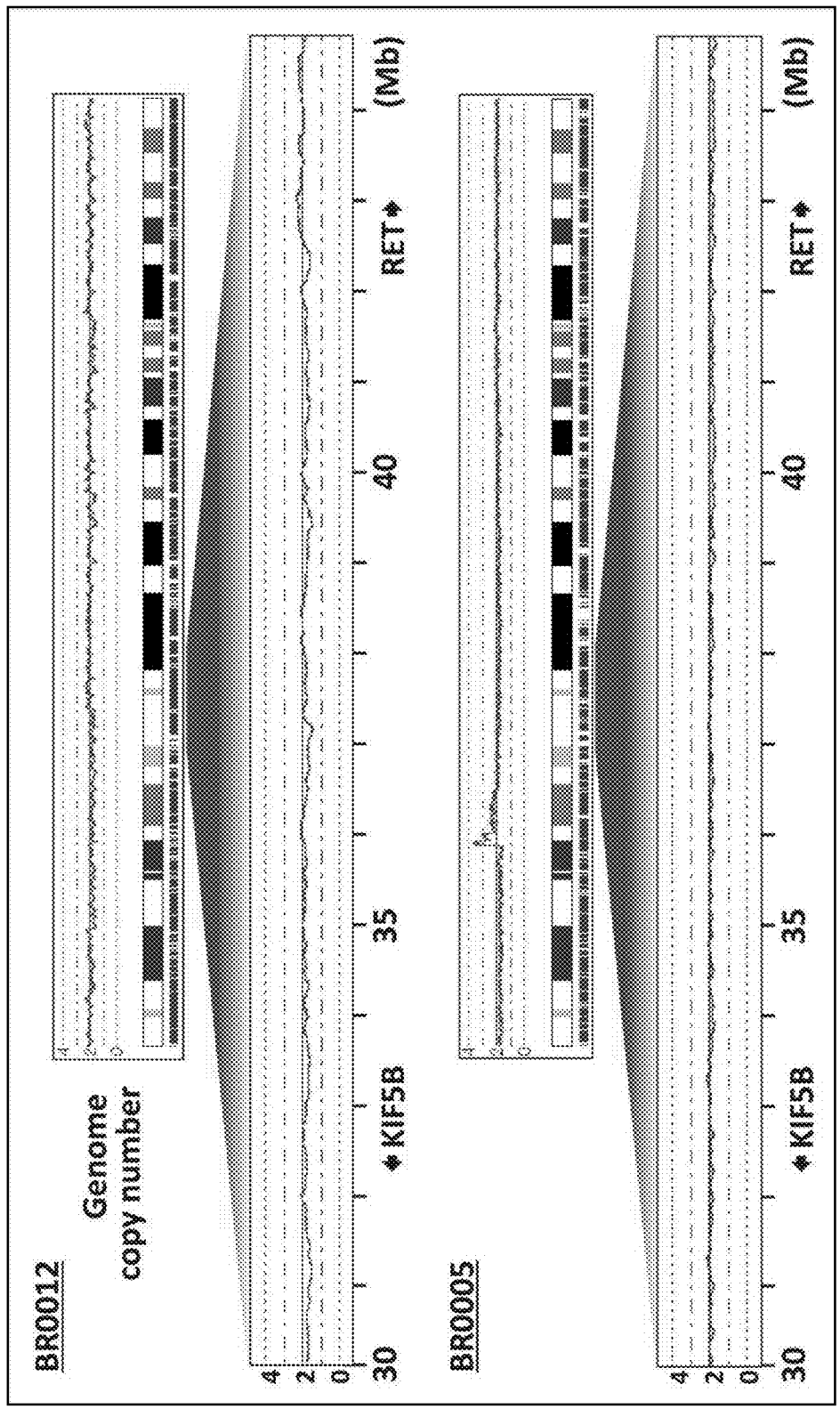
FIG. 9 depicts schematic drawings showing the results of determining the genome copy numbers of chromosome 10 in two (BR0012 and BR0005) out of the six cases with fusions between the KIF5B gene and the RET gene.
Figure 10:
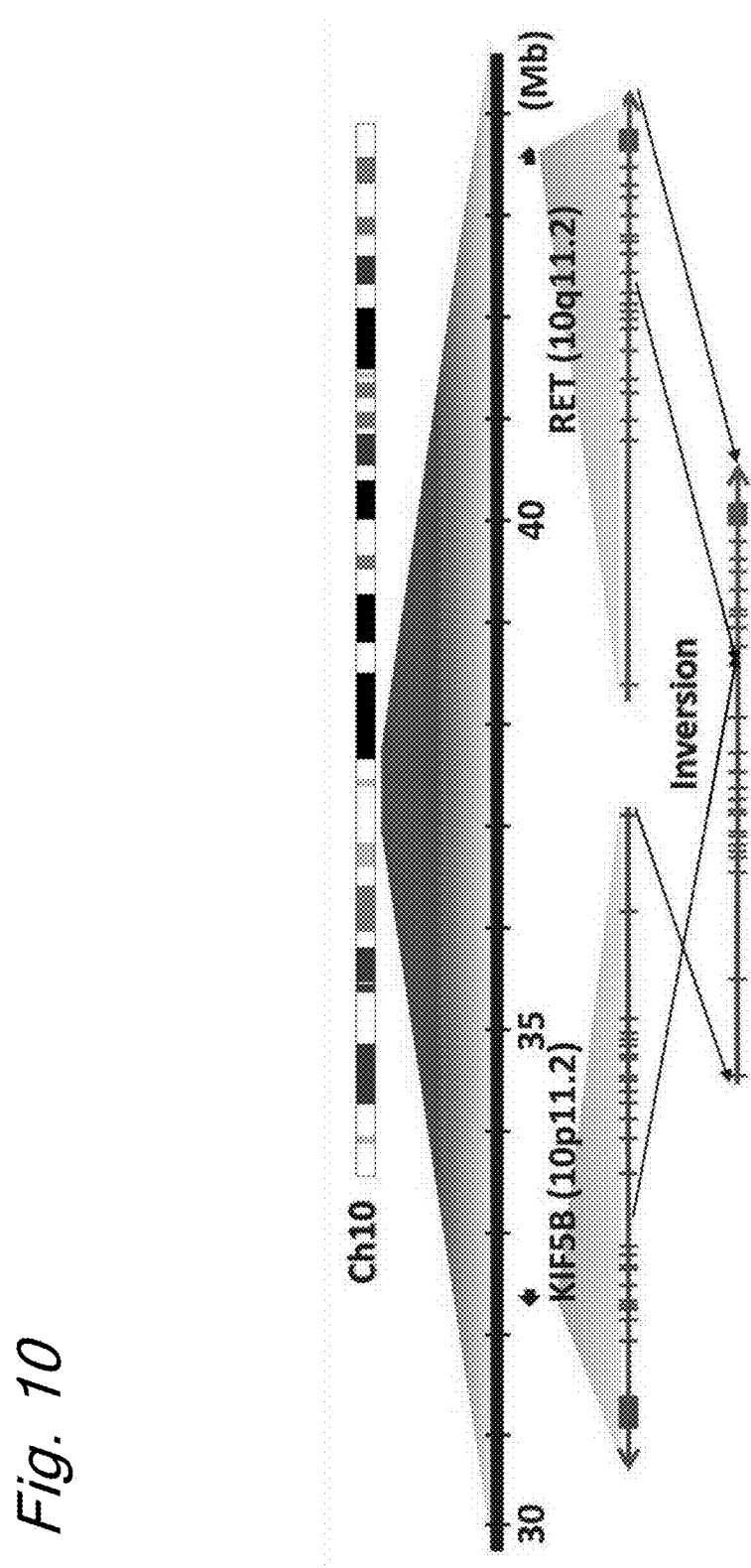
FIG. 10 depicts a schematic drawing showing a deduced chromosomal rearrangement responsible for a KIF5B-RET fusion (variant 1).

The results also revealed that the evidence of no change in genome copy number at the two loci as shown in FIGS. 8 and 9 indicates that a chromosomal inversion had occurred between the long and short arms in the centromeric region of chromosome 10 as shown in FIG. 10.

The DNA sequences around the breakpoints in the genomes of the RET fusion positive specimens revealed no significant homology. Joining was effected without any nucleotide overlaps or insertions at the breakpoint of case BR0020, while insertions (BR1001 and BR1003) or overlaps (BR1002 and BR0030) were observed in other cases (refer to FIG. 6). Joining accompanied by the insertion of a 349 bp DNA fragment was found in case BR1004 (refer to FIG. 7).

Therefore, these results are consistent with many other chromosomal translocations which had been observed in human cancers (refer to Mani, R. S., et al., *Nat Rev Genet,* 2010, Vol. 11, p. 819-829) and hence suggest that the KIF5B-RET fusions were produced through illegitimate repair of DNA double strand breaks through non-homologous end joining Example 4

Next, the RET fusion positive case (BR0020) was subjected to fluorescence in situ hybridization analysis. The obtained results are shown in FIG. 11. As is evident from the results shown in FIG. 11, the analysis using a probe that hybridizes to the portion consisting of a region upstream from the coding region for the kinase domain of the RET gene toward the 5' terminal (5' RET probe 1), and a probe that hybridizes to the portion consisting of said coding region and a region downstream from said coding region toward the 3' terminal (3' RET probe 1) revealed a split in the signals from the probes.

Example 5

Next, all of the six LADCs with the KIF5B-RET fusion were investigated for the presence or absence of other known mutations (EGFR, KRAS and ALK mutations; refer to Non-patent Documents 1, 5 and 7). The obtained results are shown in Table 4. All of these LADCs were also examined for pathological findings. The obtained results are shown in FIGS. 11 and 12. As referred to in Tables 4 and 5, "ADC" indicates "adenocarcinoma".

TABLE 4

| No. | Sample | Country | Sex | Age | Smoking (Pack-years) | KIF5B-RET fusion (fused exons) | Oncogene mutations * | Pathological stage | Pathological findings | RET staining | TTF1 staining |
|---|---|---|---|---|---|---|---|---|---|---|---|
| 1 | BR0020 | Japan | Male | 57 | Never | Variant 1 (ex15-ex12) | None | IIB | Moderately differentiated ADC | + | + |
| 2 | BR1001 | Japan | Female | 65 | Never | Variant 1 (ex15-ex12) | None | IB | Well differentiated ADC | + | + |
| 3 | BR1002 | Japan | Female | 64 | Never | Variant 1 (ex15-ex12) | None | IB | Well differentiated ADC | + | + |
| 4 | BR0030 | Japan | Male | 57 | Never | Variant 2 (ex16-ex12) | None | IA | Well differentiated ADC | + | + |
| 5 | BR1003 | Japan | Male | 28 | Never | Variant 3 (ex23-ex12) | None | IA | Well differentiated ADC | + | + |
| 6 | BR1004 | Japan | Female | 71 | Never | Variant 4 (ex24-ex8) | None | IA | Moderately differentiated ADC | NT | NT |
| 7 | NCI1580 | USA | Male | 63 | Ever (unknown) | Variant 1 (ex15-ex12) | Unknown | II | Moderately differentiated ADC | NT | NT |
| 8 | NCI16052 | USA | Male | 62 | Ever (78) | Variant 1 (ex15-ex12) | Unknown | III | Moderately differentiated ADC | NT | NT |
| 9 | NOR595 | Norway | Male | 55 | Ever (26) | Variant 1 (ex15-ex12) | Unknown | IB | ADC | NT | NT |

* EGFR mutations, KRAS mutations, ALK fusions
NT: Not tested

As is evident from the results shown in Table 4, all of the six cases were negative for EGFR, KRAS and ALK mutations, viz., triple negative cases; the RET fusion was mutually exclusive with other oncogenic alterations. All the cases were positive for thyroid transcription factor 1 (TTF1), a marker for LADC.

Therefore, the results suggested that the KIF5B-RET fusion is a driver mutation which is responsible for 5.5% (6/109) of triple negative LADCs.

As shown in FIGS. 12 and 13, it was found that KIF5B-RET fusion positive tumors grew in a papillary or lepidic fashion and were well or moderately differentiated.

Example 6

Next, the KIF5B-RET fusion positive LADCs were investigated for their RET expression level. The obtained results are shown in FIGS. 3, 14, 15 and Table 4.

As shown in FIGS. 3 and 14, the KIF5B-RET fusion positive LADCs showed higher RET expression level than fusion negative LADCs and non-cancerous lung tissues (refer to FIG. 3). The same tendency of RET expression level was also ascertained by the gene expression data from 228 cases including six fusion positive LADCs (refer to FIG. 14).

Further, as is evident from the results shown in FIG. 15, an immunohistochemical analysis using an antibody against the C-terminal region of RET protein detected positive cytoplasmic staining of RET in the tumor cells of the fusion positive cases searched (refer to FIG. 15 and Table 4). In contrast, no such staining was detected in non-cancerous lung tissues or in the tumor cells of some fusion negative cases.

Some (22%, 48/222) of the LADCs without KIF5B-RET fusion also expressed the RET gene at a higher level than the non-cancerous lung tissues. The six cases showing such an expression (refer to Table 5) were analyzed by RNA sequencing, but there was not found a RET gene fusion to other genes than KIF5B, a somatic RET gene mutation, or an increased copy number at the RET locus (refer to FIGS. 16 and 17).

KIF5B-RET fusion in LADCs from the U.S.A. cohort (refer to Table 3) was examined. The obtained results are shown in FIGS. 18 and 19.

As is evident from the results shown in FIGS. 18 and 19, the variant 1 transcript was detected in 1 out of 80 (1.3%) U.S.A. subjects, who was Caucasian. As in the case of the Japanese subjects noted above, this Caucasian subject was also negative for EGFR, KRAS and ALK mutations, viz., a triple negative subject; these three mutations were shown to be mutually exclusive with the KIF5B-RET fusion.

Thus, it was found that the KIF5B-RET fusion occurred in 1-3% of LADCs from Asian and non-Asian individuals, respectively. The non-Asian subject with a RET fusion was an ever-smoker, whereas the six Japanese fusion positive subjects were never-smokers; therefore, the influence of smoking on KIF5B-RET fusion positive subjects has yet to be determined Industrial Applicability As described above, the present invention enables prediction of the effectiveness of cancer treatments with RET tyrosine kinase inhibitors.

Inhibitors having an inhibitory effect against RET receptor tyrosine kinase have already been introduced into cancer care. FDA-approved inhibitors, such as Vandetanib and Sorafenib, have been shown to have anticancer activity on non-small-cell lung cancers. As mentioned above, in-frame fusions between the KIF5B gene and the RET gene developed in several cases. Further, the fusion between the KIF5B gene and the RET gene is deviated from EGFR/KRAS/ALK-mutated tumors. Thus, the KIF5B-RET fusion can serve as a target for existing tyrosine kinase inhibitors. There were observed KIF5B-RET fusions not only in Asian individuals including Japanese but also in European and American individuals. Therefore, the method of the present invention is of great benefit to improve the efficiency of cancer treatments in individuals of a wide variety of races.

Sequence Listing Free Text

SEQ ID NO: 1
<223> KIF5B cDNA

TABLE 5

| No. | Sample | Sex | Age | Smoking (Pack-years) | Oncogene mutations | Pathological stage | Pathological findings |
|---|---|---|---|---|---|---|---|
| 1 | BR0012 | Male | 65 | Ever (92) | None | IIB | Poorly differentiated ADC |
| 2 | BR0005 | Male | 59 | Ever (62) | KRAS | IIB | Poorly differentiated ADC |
| 3 | BR0015 | Female | 49 | Ever (20) | None | IIB | Poorly differentiated ADC |
| 4 | BR0031 | Male | 54 | Never | None | IA | Well differentiated ADC |
| 5 | BR0043 | Male | 68 | Ever (48) | None | IIB | Moderately differentiated ADC |
| 6 | BR0032 | Female | 61 | Never | None | IA | Well differentiated ADC |

Example 7

It had been shown that the distribution of oncogene mutations in LADCs varies among ethnic groups. Asian individuals have a higher prevalence of EGFR mutations than non-Asian individuals (50% vs 10%), and the tendency is reversed for KRAS mutations (10% vs 30%). It had also been known that the prevalence of ALK fusions is equal (5%) between both groups (refer to: Non-patent Document 6; and Shigematsu, H., et al., *J Natl Cancer Inst*, 2005, Vol. 97, p. 339-346). Thus, in order to understand the distribution of KIF5B-RET fusions in non-Asian individuals, the prevalence of SEQ ID NO: 3
<223> RET cDNA
SEQ ID NO: 5
<223> KIF5B-RET fusion variant 1
SEQ ID NO: 7
<223> KIF5B-RET fusion variant 2
SEQ ID NO: 9
<223> KIF5B-RET fusion variant 3
SEQ ID NO: 11
<223> KIF5B-RET fusion variant 4
SEQ ID NOs: 13-28
<223> Artificially synthesized primer sequence

We claim:

1. A method for determining the effectiveness of a cancer treatment with a RET tyrosine kinase inhibitor, the method comprising the step of detecting the presence or absence of a polynucleotide in a sample isolated from a patient, wherein the polynucleotide is selected from a group consisting of the DNA sequences of SEQ ID NOs: 5, 7, 9 or 11 and encodes a polypeptide comprising a N-terminal moiety of a KIF5B protein and a C-terminal moiety of a RET protein fused together, the N-terminal moiety of the KIF5B protein comprising a motor domain located on the N-terminal side of the KIF5B and part of all coiled-coil domain of KIF5B protein, the C-terminal moiety of the RET protein comprising a kinase domain located on the C-terminal side of the RET protein, wherein in a case where the presence of the polynucleotide is detected, the cancer treatment with the RET tyrosine kinase inhibitor is determined to be highly effective in the patient.

\* \* \* \* \*

UNITED STATES PATENT AND TRADEMARK OFFICE
CERTIFICATE OF CORRECTION

PATENT NO.         : 9,216,172 B2
APPLICATION NO.    : 14/236900
DATED              : December 22, 2015
INVENTOR(S)        : Takashi Kohno et al.

Page 1 of 1

It is certified that error appears in the above-identified patent and that said Letters Patent is hereby corrected as shown below:

In the Claims:

At column 126, claim number 1, line number 31, replace "part of all coiled-coil domain" with --part or all of the coiled-coil domain--.

Signed and Sealed this
Twelfth Day of April, 2016

Michelle K. Lee
*Director of the United States Patent and Trademark Office*

SEQUENCE LISTING

<160> NUMBER OF SEQ ID NOS: 28

<210> SEQ ID NO 1
<211> LENGTH: 5905
<212> TYPE: DNA
<213> ORGANISM: Homo sapiens
<220> FEATURE:
<221> NAME/KEY: CDS
<222> LOCATION: (471)..(3362)
<223> OTHER INFORMATION: KIF5B cDNA

<400> SEQUENCE: 1

```
ctcctcccgc accgccctgt cgcccaacgg cggcctcagg agtgatcggg cagcagtcgg      60
ccggccagcg gacggcagag cgggcggacg ggtaggcccg gcctgctctt cgcgaggagg     120
aagaaggtgg ccactctccc ggtccccaga acctccccag cccccgcagt ccgcccagac     180
cgtaaagggg gacgctgagg agccgcggac gctctccccg gtgccgccgc cgctgccgcc     240
gccatggctg ccatgatgga tcggaagtga gcattagggt taacggctgc cggcgccggc     300
tcttcaagtc ccggctcccc ggccgcctcc acccggggaa gcgcagcgcg gcgcagctga     360
ctgctgcctc tcacgcccct cgcgaccaca agccctcagg tccggcgcgt tccctgcaag     420
actgagcggc ggggagtggc tcccggccgc cggccccggc tgcgagaaag atg gcg        476
                                                         Met Ala
                                                           1
```

```
gac ctg gcc gag tgc aac atc aaa gtg atg tgt cgc ttc aga cct ctc       524
Asp Leu Ala Glu Cys Asn Ile Lys Val Met Cys Arg Phe Arg Pro Leu
        5                  10                  15
```

```
aac gag tct gaa gtg aac cgc ggc gac aag tac atc gcc aag ttt cag       572
Asn Glu Ser Glu Val Asn Arg Gly Asp Lys Tyr Ile Ala Lys Phe Gln
 20                  25                  30
```

```
gga gaa gac acg gtc gtg atc gcg tcc aag cct tat gca ttt gat cgg       620
Gly Glu Asp Thr Val Val Ile Ala Ser Lys Pro Tyr Ala Phe Asp Arg
35                  40                  45                  50
```

```
gtg ttc cag tca agc aca tct caa gag caa gtg tat aat gac tgt gca       668
Val Phe Gln Ser Ser Thr Ser Gln Glu Gln Val Tyr Asn Asp Cys Ala
                55                  60                  65
```

```
aag aag att gtt aaa gat gta ctt gaa gga tat aat gga aca ata ttt       716
Lys Lys Ile Val Lys Asp Val Leu Glu Gly Tyr Asn Gly Thr Ile Phe
            70                  75                  80
```

```
gca tat gga caa aca tcc tct ggg aag aca cac aca atg gag ggt aaa       764
Ala Tyr Gly Gln Thr Ser Ser Gly Lys Thr His Thr Met Glu Gly Lys
        85                  90                  95
```

```
ctt cat gat cca gaa ggc atg gga att att cca aga ata gtg caa gat       812
Leu His Asp Pro Glu Gly Met Gly Ile Ile Pro Arg Ile Val Gln Asp
    100                 105                 110
```

```
att ttt aat tat att tac tcc atg gat gaa aat ttg gaa ttt cat att       860
Ile Phe Asn Tyr Ile Tyr Ser Met Asp Glu Asn Leu Glu Phe His Ile
115                 120                 125                 130
```

```
aag gtt tca tat ttt gaa ata tat ttg gat aag ata agg gac ctg tta       908
Lys Val Ser Tyr Phe Glu Ile Tyr Leu Asp Lys Ile Arg Asp Leu Leu
                135                 140                 145
```

```
gat gtt tca aag acc aac ctt tca gtt cat gaa gac aaa aac cga gtt       956
Asp Val Ser Lys Thr Asn Leu Ser Val His Glu Asp Lys Asn Arg Val
            150                 155                 160
```

```
ccc tat gta aag ggg tgc aca gag cgt ttt gta tgt agt cca gat gaa      1004
Pro Tyr Val Lys Gly Cys Thr Glu Arg Phe Val Cys Ser Pro Asp Glu
        165                 170                 175
```

```
gtt atg gat acc ata gat gaa gga aaa tcc aac aga cat gta gca gtt      1052
Val Met Asp Thr Ile Asp Glu Gly Lys Ser Asn Arg His Val Ala Val
    180                 185                 190
```

```
aca aat atg aat gaa cat agc tct agg agt cac agt ata ttt ctt att    1100
Thr Asn Met Asn Glu His Ser Ser Arg Ser His Ser Ile Phe Leu Ile
195                 200                 205                 210 aat gtc aaa caa gag aac aca caa acg gaa caa aag ctg agt gga aaa    1148
Asn Val Lys Gln Glu Asn Thr Gln Thr Glu Gln Lys Leu Ser Gly Lys
            215                 220                 225 ctt tat ctg gtt gat tta gct ggt agt gaa aag gtt agt aaa act gga    1196
Leu Tyr Leu Val Asp Leu Ala Gly Ser Glu Lys Val Ser Lys Thr Gly
        230                 235                 240 gct gaa ggt gct gtg ctg gat gaa gct aaa aac atc aac aag tca ctt    1244
Ala Glu Gly Ala Val Leu Asp Glu Ala Lys Asn Ile Asn Lys Ser Leu
    245                 250                 255 tct gct ctt gga aat gtt att tct gct ttg gct gag ggt agt aca tat    1292
Ser Ala Leu Gly Asn Val Ile Ser Ala Leu Ala Glu Gly Ser Thr Tyr
260                 265                 270 gtt cca tat cga gat agt aaa atg aca aga atc ctt caa gat tca tta    1340
Val Pro Tyr Arg Asp Ser Lys Met Thr Arg Ile Leu Gln Asp Ser Leu
275                 280                 285                 290 ggt ggc aac tgt aga acc act att gta att tgc tgc tct cca tca tca    1388
Gly Gly Asn Cys Arg Thr Thr Ile Val Ile Cys Cys Ser Pro Ser Ser
            295                 300                 305 tac aat gag tct gaa aca aaa tct aca ctc tta ttt ggc caa agg gcc    1436
Tyr Asn Glu Ser Glu Thr Lys Ser Thr Leu Leu Phe Gly Gln Arg Ala
        310                 315                 320 aaa aca att aag aac aca gtt tgt gtc aat gtg gag tta act gca gaa    1484
Lys Thr Ile Lys Asn Thr Val Cys Val Asn Val Glu Leu Thr Ala Glu
    325                 330                 335 cag tgg aaa aag aag tat gaa aaa gaa aaa gaa aaa aat aag atc ctg    1532
Gln Trp Lys Lys Lys Tyr Glu Lys Glu Lys Glu Lys Asn Lys Ile Leu
340                 345                 350 cgg aac act att cag tgg ctt gaa aat gag ctc aac aga tgg cgt aat    1580
Arg Asn Thr Ile Gln Trp Leu Glu Asn Glu Leu Asn Arg Trp Arg Asn
355                 360                 365                 370 ggg gag acg gtg cct att gat gaa cag ttt gac aaa gag aaa gcc aac    1628
Gly Glu Thr Val Pro Ile Asp Glu Gln Phe Asp Lys Glu Lys Ala Asn
            375                 380                 385 ttg gaa gct ttc aca gtg gat aaa gat att act ctt acc aat gat aaa    1676
Leu Glu Ala Phe Thr Val Asp Lys Asp Ile Thr Leu Thr Asn Asp Lys
        390                 395                 400 cca gca acc gca att gga gtt ata gga aat ttt act gat gct gaa aga    1724
Pro Ala Thr Ala Ile Gly Val Ile Gly Asn Phe Thr Asp Ala Glu Arg
    405                 410                 415 aga aag tgt gaa gaa gaa att gct aaa tta tac aaa cag ctt gat gac    1772
Arg Lys Cys Glu Glu Glu Ile Ala Lys Leu Tyr Lys Gln Leu Asp Asp
420                 425                 430 aag gat gaa gaa att aac cag caa agt caa ctg gta gag aaa ctg aag    1820
Lys Asp Glu Glu Ile Asn Gln Gln Ser Gln Leu Val Glu Lys Leu Lys
435                 440                 445                 450 acg caa atg ttg gat cag gag gag ctt ttg gca tct acc aga agg gat    1868
Thr Gln Met Leu Asp Gln Glu Glu Leu Leu Ala Ser Thr Arg Arg Asp
            455                 460                 465 caa gac aat atg caa gct gag ctg aat cgc ctt caa gca gaa aat gat    1916
Gln Asp Asn Met Gln Ala Glu Leu Asn Arg Leu Gln Ala Glu Asn Asp
        470                 475                 480 gcc tct aaa gaa gaa gtg aaa gaa gtt tta cag gcc cta gaa gaa ctt    1964
Ala Ser Lys Glu Glu Val Lys Glu Val Leu Gln Ala Leu Glu Glu Leu
    485                 490                 495 gct gtc aat tat gat cag aag tct cag gaa gtt gaa gac aaa act aag    2012
Ala Val Asn Tyr Asp Gln Lys Ser Gln Glu Val Glu Asp Lys Thr Lys
```

|  |  |  |  |  |  |  |  |  |  |  |  |  |  |  |  |
|---|---|---|---|---|---|---|---|---|---|---|---|---|---|---|---|
| gaa | tat | gaa | ttg | ctt | agt | gat | gaa | ttg | aat | cag | aaa | tcg | gca | act | tta | 2060 |
| Glu | Tyr | Glu | Leu | Leu | Ser | Asp | Glu | Leu | Asn | Gln | Lys | Ser | Ala | Thr | Leu |
| 515 |  |  |  | 520 |  |  |  |  | 525 |  |  |  |  | 530 |

```
gaa tat gaa ttg ctt agt gat gaa ttg aat cag aaa tcg gca act tta   2060
Glu Tyr Glu Leu Leu Ser Asp Glu Leu Asn Gln Lys Ser Ala Thr Leu
515                 520                 525                 530 gcg agt ata gat gct gag ctt cag aaa ctt aag gaa atg acc aac cac   2108
Ala Ser Ile Asp Ala Glu Leu Gln Lys Leu Lys Glu Met Thr Asn His
                535                 540                 545 cag aaa aaa cga gca gct gag atg atg gca tct tta cta aaa gac ctt   2156
Gln Lys Lys Arg Ala Ala Glu Met Met Ala Ser Leu Leu Lys Asp Leu
            550                 555                 560 gca gaa ata gga att gct gtg gga aat aat gat gta aag cag cct gag   2204
Ala Glu Ile Gly Ile Ala Val Gly Asn Asn Asp Val Lys Gln Pro Glu
        565                 570                 575 gga act ggc atg ata gat gaa gag ttc act gtt gca aga ctc tac att   2252
Gly Thr Gly Met Ile Asp Glu Glu Phe Thr Val Ala Arg Leu Tyr Ile
    580                 585                 590 agc aaa atg aag tca gaa gta aaa acc atg gtg aaa cgt tgc aag cag   2300
Ser Lys Met Lys Ser Glu Val Lys Thr Met Val Lys Arg Cys Lys Gln
595                 600                 605                 610 tta gaa agc aca caa act gag agc aac aaa aaa atg gaa gaa aat gaa   2348
Leu Glu Ser Thr Gln Thr Glu Ser Asn Lys Lys Met Glu Glu Asn Glu
                615                 620                 625 aag gag tta gca gca tgt cag ctt cgt atc tct caa cat gaa gcc aaa   2396
Lys Glu Leu Ala Ala Cys Gln Leu Arg Ile Ser Gln His Glu Ala Lys
            630                 635                 640 atc aag tca ttg act gaa tac ctt caa aat gtg gaa caa aag aaa aga   2444
Ile Lys Ser Leu Thr Glu Tyr Leu Gln Asn Val Glu Gln Lys Lys Arg
        645                 650                 655 cag ttg gag gaa tct gtc gat gcc ctc agt gaa gaa cta gtc cag ctt   2492
Gln Leu Glu Glu Ser Val Asp Ala Leu Ser Glu Glu Leu Val Gln Leu
    660                 665                 670 cga gca caa gag aaa gtc cat gaa atg gaa aag gag cac tta aat aag   2540
Arg Ala Gln Glu Lys Val His Glu Met Glu Lys Glu His Leu Asn Lys
675                 680                 685                 690 gtt cag act gca aat gaa gtt aag caa gct gtt gaa cag cag atc cag   2588
Val Gln Thr Ala Asn Glu Val Lys Gln Ala Val Glu Gln Gln Ile Gln
                695                 700                 705 agc cat aga gaa act cat caa aaa cag atc agt agt ttg aga gat gaa   2636
Ser His Arg Glu Thr His Gln Lys Gln Ile Ser Ser Leu Arg Asp Glu
            710                 715                 720 gta gaa gca aaa gca aaa ctt att act gat ctt caa gac caa aac cag   2684
Val Glu Ala Lys Ala Lys Leu Ile Thr Asp Leu Gln Asp Gln Asn Gln
        725                 730                 735 aaa atg atg tta gag cag gaa cgt cta aga gta gaa cat gag aag ttg   2732
Lys Met Met Leu Glu Gln Glu Arg Leu Arg Val Glu His Glu Lys Leu
    740                 745                 750 aaa gcc aca gat cag gaa aag agc aga aaa cta cat gaa ctt acg gtt   2780
Lys Ala Thr Asp Gln Glu Lys Ser Arg Lys Leu His Glu Leu Thr Val
755                 760                 765                 770 atg caa gat aga cga gaa caa gca aga caa gac ttg aag ggt ttg gaa   2828
Met Gln Asp Arg Arg Glu Gln Ala Arg Gln Asp Leu Lys Gly Leu Glu
                775                 780                 785 gag aca gtg gca aaa gaa ctt cag act tta cac aac ctg cgc aaa ctc   2876
Glu Thr Val Ala Lys Glu Leu Gln Thr Leu His Asn Leu Arg Lys Leu
            790                 795                 800 ttt gtt cag gac ctg gct aca aga gtt aaa aag agt gct gag att gat   2924
Phe Val Gln Asp Leu Ala Thr Arg Val Lys Lys Ser Ala Glu Ile Asp
        805                 810                 815 tct gat gac acc gga ggc agc gct gct cag aag caa aaa atc tcc ttt   2972
```

```
Ser Asp Asp Thr Gly Gly Ser Ala Ala Gln Lys Gln Lys Ile Ser Phe
    820                 825                 830 ctt gaa aat aat ctt gaa cag ctc act aaa gtg cac aaa cag ttg gta    3020
Leu Glu Asn Asn Leu Glu Gln Leu Thr Lys Val His Lys Gln Leu Val
835                 840                 845                 850 cgt gat aat gca gat ctc cgc tgt gaa ctt cct aag ttg gaa aag cga    3068
Arg Asp Asn Ala Asp Leu Arg Cys Glu Leu Pro Lys Leu Glu Lys Arg
                855                 860                 865 ctt cga gct aca gct gag aga gtg aaa gct ttg gaa tca gca ctg aaa    3116
Leu Arg Ala Thr Ala Glu Arg Val Lys Ala Leu Glu Ser Ala Leu Lys
            870                 875                 880 gaa gct aaa gaa aat gca tct cgt gat cgc aaa cgc tat cag caa gaa    3164
Glu Ala Lys Glu Asn Ala Ser Arg Asp Arg Lys Arg Tyr Gln Gln Glu
        885                 890                 895 gta gat cgc ata aag gaa gca gtc agg tca aag aat atg gcc aga aga    3212
Val Asp Arg Ile Lys Glu Ala Val Arg Ser Lys Asn Met Ala Arg Arg
    900                 905                 910 ggg cat tct gca cag att gct aaa cct att cgt ccc ggg caa cat cca    3260
Gly His Ser Ala Gln Ile Ala Lys Pro Ile Arg Pro Gly Gln His Pro
915                 920                 925                 930 gca gct tct cca act cac cca agt gca att cgt gga gga ggt gca ttt    3308
Ala Ala Ser Pro Thr His Pro Ser Ala Ile Arg Gly Gly Gly Ala Phe
                935                 940                 945 gtt cag aac agc cag cca gtg gca gtg cga ggt gga gga ggc aaa caa    3356
Val Gln Asn Ser Gln Pro Val Ala Val Arg Gly Gly Gly Gly Lys Gln
            950                 955                 960 gtg taa tcgtttatac atacccacag gtgttaaaaa gtaatcgaag tacgaagagg     3412
Val acatggtatc aagcagtcat tcaatgacta taacctctac tcccttggga ttgtagaatt  3472
ataactttta aaaaaaatgt ataaattata cctggcctgt acagctgttt cctacctact  3532
cttcttgtaa actctgctgc ttcccaacac aactagagtg caattttggc atcttaggag  3592
ggaaaaagga cagtttacaa ctgtggccct atttattaca cagtttgtct atcgtgtctt  3652
aaatttagtc tttactgtgc caagctaact gtaccttata ggactgtact ttttgtattt  3712
tttgtgtatg tttatttttt aatctcagtt taaattacct agctgctact gcttcttgtt  3772
tttcttttcc tattaaaacg tcttcctttt tttttcttaa gagaaaatgg aacatttagg  3832
ttaaatgtct ttaaatttta ccacttaaca acactacatg cccataaaat atatccagtc  3892
agtactgtat tttaaaatcc cttgaaatga tgatatcagg gttaaaatta cttgtattgt  3952
ttctgaagtt tgctcctgaa aactactgtt tgagcactga aacgttacaa atgcctaata  4012
ggcatttgag actgagcaag gctacttgtt atctcatgaa atgcctgttg ccgagttatt  4072
ttgaatagaa atattttaaa gtatcaaaag cagatcttag tttaagggag tttggaaaag  4132
gaattatatt tctctttttc ctgattctgt actcaacaag tcttgatgga attaaaatac  4192
tctgctttat tctggtgagc ctgctagcta atataagtat tggacaggta ataatttgtc  4252
atctttaata ttagtaaaat gaattaagat attataggat taaacataat tttatacggt  4312
tagtacttta ttggccgacc taaatttata gcgtgtggaa attgagaaaa atgaagaaac  4372
aggacagata tatgatgaat taaaaatata tataggtcaa ttttggtctg aaatccctga  4432
ggtgttttta acctgctaca ctaatttgta cactaattta tttctttagt ctagaaatag  4492
taaattgttt gcaagtcact aataatcatt agataaatta ttttcttggc catagccgat  4552 aatttttgtaa tcagtactaa gtgtatacgt attttttgcca cttttttcctc agatgattaa  4612 agtaagtcaa cagcttattt taggaaactg taaaagtaat agggaaagag atttcactat  4672
```

-continued

```
ttgcttcatc agtggtaggg gggcggtgac tgcaactgtg ttagcagaaa ttcacagaga    4732
atggggattt aaggttagca gagaaacttg gaaagttctg tgttaggatc ttgctggcag    4792
aattaacttt ttgcaaaagt tttatacaca gatatttgta ttaaatttgg agccatagtc    4852
agaagactca gatcataatt ggcttatttt tctatttccg taactattgt aatttccact    4912
tttgtaataa ttttgattta aaatataaat ttatttattt atttttttaa tagtcaaaaa    4972
tctttgctgt tgtagtctgc aacctctaaa atgattgtgt tgcttttagg attgatcaga    5032
agaaacactc caaaaattga gatgaaatgt tggtgcagcc agttataagt aatatagtta    5092
acaagcaaaa aaagtgctgc cacctttttat gatgattttc taaatggaga acatttggc     5152 tgcatccaca tagacccttta tgttttgttt tcagttgaaa acttgcctcc tttggcaaca    5212
ttcgtaaatg aagcagaatt ttttttttctc ttttttccaa atatgttagt tttgttcttg   5272
taagatgtat catgggtatt ggtgctgtgt aatgaacaac gaattttaat tagcatgtgg    5332
ttcagaatat acaatgttag gttttttaaaa agtatcttga tggttctttt ctatttataa   5392
tttcagactt tcataaagtg taccaagaat ttcataaatt tgttttcagt gaactgcttt    5452
ttgctatggt aggtcattaa acacagcact tactcttaaa aatgaaaatt tctgatcatc    5512
taggatattg acacatttca atttgcagtg tcttttttgac tggatatatt aacgttcctc   5572
tgaatggcat tgatagatgg ttcagaagag aaactcaatg aaataaagag aatatttatt    5632
catggcgatt aattaaatta tttgcctaac ttaagaaaac tactgtgcgt aactctcagt    5692
ttgtgcttaa ctccatttga catgaggtga cagaagagag tctgagtcta cctgtggaat    5752
atgttggttt attttcagtg cttgaagata cattcacaaa tacttggttt gggaagacac    5812 cgtttaatttt aagttaact tgcatgttgt aaatgcgttt tatgtttaaa taaagaggaa     5872
aattttttga aatgtaaaaa aaaaaaaaaa aaa                                 5905
```

<210> SEQ ID NO 2
<211> LENGTH: 963
<212> TYPE: PRT
<213> ORGANISM: Homo sapiens

<400> SEQUENCE: 2

```
Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
```

```
                    145                 150                 155                 160
                Arg Val Pro Tyr Val Lys Gly Cys Thr Glu Arg Phe Val Cys Ser Pro
                                165                 170                 175

Asp Glu Val Met Asp Thr Ile Asp Glu Gly Lys Ser Asn Arg His Val
                                180                 185                 190

Ala Val Thr Asn Met Asn Glu His Ser Ser Arg Ser His Ser Ile Phe
                                195                 200                 205

Leu Ile Asn Val Lys Gln Glu Asn Thr Gln Thr Glu Gln Lys Leu Ser
                210                 215                 220

Gly Lys Leu Tyr Leu Val Asp Leu Ala Gly Ser Glu Lys Val Ser Lys
                225                 230                 235                 240

Thr Gly Ala Glu Gly Ala Val Leu Asp Glu Ala Lys Asn Ile Asn Lys
                                245                 250                 255

Ser Leu Ser Ala Leu Gly Asn Val Ile Ser Ala Leu Ala Glu Gly Ser
                                260                 265                 270

Thr Tyr Val Pro Tyr Arg Asp Ser Lys Met Thr Arg Ile Leu Gln Asp
                                275                 280                 285

Ser Leu Gly Gly Asn Cys Arg Thr Thr Ile Val Ile Cys Cys Ser Pro
                290                 295                 300

Ser Ser Tyr Asn Glu Ser Glu Thr Lys Ser Thr Leu Leu Phe Gly Gln
                305                 310                 315                 320

Arg Ala Lys Thr Ile Lys Asn Thr Val Cys Val Asn Val Glu Leu Thr
                                325                 330                 335

Ala Glu Gln Trp Lys Lys Lys Tyr Glu Lys Glu Lys Glu Lys Asn Lys
                                340                 345                 350

Ile Leu Arg Asn Thr Ile Gln Trp Leu Glu Asn Glu Leu Asn Arg Trp
                                355                 360                 365

Arg Asn Gly Glu Thr Val Pro Ile Asp Glu Gln Phe Asp Lys Glu Lys
                                370                 375                 380

Ala Asn Leu Glu Ala Phe Thr Val Asp Lys Asp Ile Thr Leu Thr Asn
                385                 390                 395                 400

Asp Lys Pro Ala Thr Ala Ile Gly Val Ile Gly Asn Phe Thr Asp Ala
                                405                 410                 415

Glu Arg Arg Lys Cys Glu Glu Glu Ile Ala Lys Leu Tyr Lys Gln Leu
                                420                 425                 430

Asp Asp Lys Asp Glu Glu Ile Asn Gln Gln Ser Gln Leu Val Glu Lys
                                435                 440                 445

Leu Lys Thr Gln Met Leu Asp Gln Glu Glu Leu Leu Ala Ser Thr Arg
                                450                 455                 460

Arg Asp Gln Asp Asn Met Gln Ala Glu Leu Asn Arg Leu Gln Ala Glu
                465                 470                 475                 480

Asn Asp Ala Ser Lys Glu Glu Val Lys Glu Val Leu Gln Ala Leu Glu
                                485                 490                 495

Glu Leu Ala Val Asn Tyr Asp Gln Lys Ser Gln Glu Val Glu Asp Lys
                                500                 505                 510

Thr Lys Glu Tyr Glu Leu Leu Ser Asp Glu Leu Asn Gln Lys Ser Ala
                                515                 520                 525

Thr Leu Ala Ser Ile Asp Ala Glu Leu Gln Lys Leu Lys Glu Met Thr
                                530                 535                 540

Asn His Gln Lys Lys Arg Ala Ala Glu Met Met Ala Ser Leu Leu Lys
                545                 550                 555                 560

Asp Leu Ala Glu Ile Gly Ile Ala Val Gly Asn Asn Asp Val Lys Gln
                                565                 570                 575
```

```
Pro Glu Gly Thr Gly Met Ile Asp Glu Glu Phe Thr Val Ala Arg Leu
            580                 585                 590
Tyr Ile Ser Lys Met Lys Ser Glu Val Lys Thr Met Val Lys Arg Cys
        595                 600                 605
Lys Gln Leu Glu Ser Thr Gln Thr Glu Ser Asn Lys Lys Met Glu Glu
    610                 615                 620
Asn Glu Lys Glu Leu Ala Ala Cys Gln Leu Arg Ile Ser Gln His Glu
625                 630                 635                 640
Ala Lys Ile Lys Ser Leu Thr Glu Tyr Leu Gln Asn Val Glu Gln Lys
                645                 650                 655
Lys Arg Gln Leu Glu Glu Ser Val Asp Ala Leu Ser Glu Glu Leu Val
            660                 665                 670
Gln Leu Arg Ala Gln Glu Lys Val His Glu Met Glu Lys Glu His Leu
        675                 680                 685
Asn Lys Val Gln Thr Ala Asn Glu Val Lys Gln Ala Val Glu Gln Gln
    690                 695                 700
Ile Gln Ser His Arg Glu Thr His Gln Lys Gln Ile Ser Ser Leu Arg
705                 710                 715                 720
Asp Glu Val Glu Ala Lys Ala Lys Leu Ile Thr Asp Leu Gln Asp Gln
                725                 730                 735
Asn Gln Lys Met Met Leu Glu Gln Glu Arg Leu Arg Val Glu His Glu
            740                 745                 750
Lys Leu Lys Ala Thr Asp Gln Glu Lys Ser Arg Lys Leu His Glu Leu
        755                 760                 765
Thr Val Met Gln Asp Arg Arg Glu Gln Ala Arg Gln Asp Leu Lys Gly
    770                 775                 780
Leu Glu Glu Thr Val Ala Lys Glu Leu Gln Thr Leu His Asn Leu Arg
785                 790                 795                 800
Lys Leu Phe Val Gln Asp Leu Ala Thr Arg Val Lys Lys Ser Ala Glu
                805                 810                 815
Ile Asp Ser Asp Asp Thr Gly Gly Ser Ala Ala Gln Lys Gln Lys Ile
            820                 825                 830
Ser Phe Leu Glu Asn Asn Leu Glu Gln Leu Thr Lys Val His Lys Gln
        835                 840                 845
Leu Val Arg Asp Asn Ala Asp Leu Arg Cys Glu Leu Pro Lys Leu Glu
    850                 855                 860
Lys Arg Leu Arg Ala Thr Ala Glu Arg Val Lys Ala Leu Glu Ser Ala
865                 870                 875                 880
Leu Lys Glu Ala Lys Glu Asn Ala Ser Arg Asp Arg Lys Arg Tyr Gln
                885                 890                 895
Gln Glu Val Asp Arg Ile Lys Glu Ala Val Arg Ser Lys Asn Met Ala
            900                 905                 910
Arg Arg Gly His Ser Ala Gln Ile Ala Lys Pro Ile Arg Pro Gly Gln
        915                 920                 925
His Pro Ala Ala Ser Pro Thr His Pro Ser Ala Ile Arg Gly Gly Gly
    930                 935                 940
Ala Phe Val Gln Asn Ser Gln Pro Val Ala Val Arg Gly Gly Gly Gly
945                 950                 955                 960
Lys Gln Val

<210> SEQ ID NO 3
<211> LENGTH: 5629
<212> TYPE: DNA
```

<213> ORGANISM: Homo sapiens
<220> FEATURE:
<221> NAME/KEY: CDS
<222> LOCATION: (191)..(3535)
<223> OTHER INFORMATION: RET cDNA

<400> SEQUENCE: 3

```
agtcccgcga ccgaagcagg gcgcgcagca gcgctgagtg ccccggaacg tgcgtcgcgc      60 cccagtgtc cgtcgcgtcc gccgcgcccc gggcggggat ggggcggcca gactgagcgc     120
cgcacccgcc atccagaccc gccggcccta gccgcagtcc ctccagccgt ggccccagcg    180
cgcacgggcg atg gcg aag gcg acg tcc ggt gcc gcg ggg ctg cgt ctg       229
            Met Ala Lys Ala Thr Ser Gly Ala Ala Gly Leu Arg Leu
            1               5                   10 ctg ttg ctg ctg ctg ctg ccg ctg cta ggc aaa gtg gca ttg ggc ctc       277
Leu Leu Leu Leu Leu Leu Pro Leu Leu Gly Lys Val Ala Leu Gly Leu
    15                  20                  25 tac ttc tcg agg gat gct tac tgg gag aag ctg tat gtg gac cag gcg       325
Tyr Phe Ser Arg Asp Ala Tyr Trp Glu Lys Leu Tyr Val Asp Gln Ala
30                  35                  40                  45 gcc ggc acg ccc ttg ctg tac gtc cat gcc ctg cgg gac gcc cct gag       373
Ala Gly Thr Pro Leu Leu Tyr Val His Ala Leu Arg Asp Ala Pro Glu
                50                  55                  60 gag gtg ccc agc ttc cgc ctg ggc cag cat ctc tac ggc acg tac cgc       421
Glu Val Pro Ser Phe Arg Leu Gly Gln His Leu Tyr Gly Thr Tyr Arg
            65                  70                  75 aca cgg ctg cat gag aac aac tgg atc tgc atc cag gag gac acc ggc       469
Thr Arg Leu His Glu Asn Asn Trp Ile Cys Ile Gln Glu Asp Thr Gly
        80                  85                  90 ctc ctc tac ctt aac cgg agc ctg gac cat agc tcc tgg gag aag ctc       517
Leu Leu Tyr Leu Asn Arg Ser Leu Asp His Ser Ser Trp Glu Lys Leu
    95                  100                 105 agt gtc cgc aac cgc ggc ttt ccc ctg ctc acc gtc tac ctc aag gtc       565
Ser Val Arg Asn Arg Gly Phe Pro Leu Leu Thr Val Tyr Leu Lys Val
110                 115                 120                 125 ttc ctg tca ccc aca tcc ctt cgt gag ggc gag tgc cag tgg cca ggc       613
Phe Leu Ser Pro Thr Ser Leu Arg Glu Gly Glu Cys Gln Trp Pro Gly
                130                 135                 140 tgt gcc cgc gta tac ttc tcc ttc ttc aac acc tcc ttt cca gcc tgc       661
Cys Ala Arg Val Tyr Phe Ser Phe Phe Asn Thr Ser Phe Pro Ala Cys
            145                 150                 155 agc tcc ctc aag ccc cgg gag ctc tgc ttc cca gag aca agg ccc tcc       709
Ser Ser Leu Lys Pro Arg Glu Leu Cys Phe Pro Glu Thr Arg Pro Ser
        160                 165                 170 ttc cgc att cgg gag aac cga ccc cca ggc acc ttc cac cag ttc cgc       757
Phe Arg Ile Arg Glu Asn Arg Pro Pro Gly Thr Phe His Gln Phe Arg
    175                 180                 185 ctg ctg cct gtg cag ttc ttg tgc ccc aac atc agc gtg gcc tac agg       805
Leu Leu Pro Val Gln Phe Leu Cys Pro Asn Ile Ser Val Ala Tyr Arg
190                 195                 200                 205 ctc ctg gag ggt gag ggt ctg ccc ttc cgc tgc gcc ccg gac agc ctg       853
Leu Leu Glu Gly Glu Gly Leu Pro Phe Arg Cys Ala Pro Asp Ser Leu
                210                 215                 220 gag gtg agc acg cgc tgg gcc ctg gac cgc gag cag cgg gag aag tac       901
Glu Val Ser Thr Arg Trp Ala Leu Asp Arg Glu Gln Arg Glu Lys Tyr
            225                 230                 235 gag ctg gtg gcc gtg tgc acc gtg cac gcc ggc gcg cgc gag gag gtg       949
Glu Leu Val Ala Val Cys Thr Val His Ala Gly Ala Arg Glu Glu Val
        240                 245                 250 gtg atg gtg ccc ttc ccg gtg acc gtg tac gac gag gac gac tcg gcg       997
```

```
Val Met Val Pro Phe Pro Val Thr Val Tyr Asp Glu Asp Asp Ser Ala
    255             260             265 ccc acc ttc ccc gcg ggc gtc gac acc gcc agc gcc gtg gtg gag ttc    1045
Pro Thr Phe Pro Ala Gly Val Asp Thr Ala Ser Ala Val Val Glu Phe
270             275             280             285 aag cgg aag gag gac acc gtg gtg gcc acg ctg cgt gtc ttc gat gca    1093
Lys Arg Lys Glu Asp Thr Val Val Ala Thr Leu Arg Val Phe Asp Ala
            290             295             300 gac gtg gta cct gca tca ggg gag ctg gtg agg cgg tac aca agc acg    1141
Asp Val Val Pro Ala Ser Gly Glu Leu Val Arg Arg Tyr Thr Ser Thr
                305             310             315 ctg ctc ccc ggg gac acc tgg gcc cag cag acc ttc cgg gtg gaa cac    1189
Leu Leu Pro Gly Asp Thr Trp Ala Gln Gln Thr Phe Arg Val Glu His
        320             325             330 tgg ccc aac gag acc tcg gtc cag gcc aac ggc agc ttc gtg cgg gcg    1237
Trp Pro Asn Glu Thr Ser Val Gln Ala Asn Gly Ser Phe Val Arg Ala
335             340             345 acc gta cat gac tat agg ctg gtt ctc aac cgg aac ctc tcc atc tcg    1285
Thr Val His Asp Tyr Arg Leu Val Leu Asn Arg Asn Leu Ser Ile Ser
350             355             360             365 gag aac cgc acc atg cag ctg gcg gtg ctg gtc aat gac tca gac ttc    1333
Glu Asn Arg Thr Met Gln Leu Ala Val Leu Val Asn Asp Ser Asp Phe
            370             375             380 cag ggc cca gga gcg ggc gtc ctc ttg ctc cac ttc aac gtg tcg gtg    1381
Gln Gly Pro Gly Ala Gly Val Leu Leu Leu His Phe Asn Val Ser Val
                385             390             395 ctg ccg gtc agc ctg cac ctg ccc agt acc tac tcc ctc tcc gtg agc    1429
Leu Pro Val Ser Leu His Leu Pro Ser Thr Tyr Ser Leu Ser Val Ser
        400             405             410 agg agg gct cgc cga ttt gcc cag atc ggg aaa gtc tgt gtg gaa aac    1477
Arg Arg Ala Arg Arg Phe Ala Gln Ile Gly Lys Val Cys Val Glu Asn
415             420             425 tgc cag gca ttc agt ggc atc aac gtc cag tac aag ctg cat tcc tct    1525
Cys Gln Ala Phe Ser Gly Ile Asn Val Gln Tyr Lys Leu His Ser Ser
430             435             440             445 ggt gcc aac tgc agc acg cta ggg gtg gtc acc tca gcc gag gac acc    1573
Gly Ala Asn Cys Ser Thr Leu Gly Val Val Thr Ser Ala Glu Asp Thr
            450             455             460 tcg ggg atc ctg ttt gtg aat gac acc aag gcc ctg cgg cgg ccc aag    1621
Ser Gly Ile Leu Phe Val Asn Asp Thr Lys Ala Leu Arg Arg Pro Lys
                465             470             475 tgt gcc gaa ctt cac tac atg gtg gtg gcc acc gac cag cag acc tct    1669
Cys Ala Glu Leu His Tyr Met Val Val Ala Thr Asp Gln Gln Thr Ser
        480             485             490 agg cag gcc cag gcc cag ctg ctt gta aca gtg gag ggg tca tat gtg    1717
Arg Gln Ala Gln Ala Gln Leu Leu Val Thr Val Glu Gly Ser Tyr Val
495             500             505 gcc gag gag gcg ggc tgc ccc ctg tcc tgt gca gtc agc aag aga cgg    1765
Ala Glu Glu Ala Gly Cys Pro Leu Ser Cys Ala Val Ser Lys Arg Arg
510             515             520             525 ctg gag tgt gag gag tgt ggc ggc ctg ggc tcc cca aca ggc agg tgt    1813
Leu Glu Cys Glu Glu Cys Gly Gly Leu Gly Ser Pro Thr Gly Arg Cys
            530             535             540 gag tgg agg caa gga gat ggc aaa ggg atc acc agg aac ttc tcc acc    1861
Glu Trp Arg Gln Gly Asp Gly Lys Gly Ile Thr Arg Asn Phe Ser Thr
                545             550             555 tgc tct ccc agc acc aag acc tgc ccc gac ggc cac tgc gat gtt gtg    1909
Cys Ser Pro Ser Thr Lys Thr Cys Pro Asp Gly His Cys Asp Val Val
        560             565             570
```

```
                                                    -continued gag acc caa gac atc aac att tgc cct cag gac tgc ctc cgg ggc agc     1957
Glu Thr Gln Asp Ile Asn Ile Cys Pro Gln Asp Cys Leu Arg Gly Ser
575                 580                 585 att gtt ggg gga cac gag cct ggg gag ccc cgg ggg att aaa gct ggc     2005
Ile Val Gly Gly His Glu Pro Gly Glu Pro Arg Gly Ile Lys Ala Gly
590                 595                 600                 605 tat ggc acc tgc aac tgc ttc cct gag gag gag aag tgc ttc tgc gag     2053
Tyr Gly Thr Cys Asn Cys Phe Pro Glu Glu Glu Lys Cys Phe Cys Glu
            610                 615                 620 ccc gaa gac atc cag gat cca ctg tgc gac gag ctg tgc cgc acg gtg     2101
Pro Glu Asp Ile Gln Asp Pro Leu Cys Asp Glu Leu Cys Arg Thr Val
                625                 630                 635 atc gca gcc gct gtc ctc ttc tcc ttc atc gtc tcg gtg ctg ctg tct     2149
Ile Ala Ala Ala Val Leu Phe Ser Phe Ile Val Ser Val Leu Leu Ser
                640                 645                 650 gcc ttc tgc atc cac tgc tac cac aag ttt gcc cac aag cca ccc atc     2197
Ala Phe Cys Ile His Cys Tyr His Lys Phe Ala His Lys Pro Pro Ile
655                 660                 665 tcc tca gct gag atg acc ttc cgg agg ccc gcc cag gcc ttc ccg gtc     2245
Ser Ser Ala Glu Met Thr Phe Arg Arg Pro Ala Gln Ala Phe Pro Val
670                 675                 680                 685 agc tac tcc tct tcc ggt gcc cgc cgg ccc tcg ctg gac tcc atg gag     2293
Ser Tyr Ser Ser Ser Gly Ala Arg Arg Pro Ser Leu Asp Ser Met Glu
            690                 695                 700 aac cag gtc tcc gtg gat gcc ttc aag atc ctg gag gat cca aag tgg     2341
Asn Gln Val Ser Val Asp Ala Phe Lys Ile Leu Glu Asp Pro Lys Trp
                705                 710                 715 gaa ttc cct cgg aag aac ttg gtt ctt gga aaa act cta gga gaa ggc     2389
Glu Phe Pro Arg Lys Asn Leu Val Leu Gly Lys Thr Leu Gly Glu Gly
                720                 725                 730 gaa ttt gga aaa gtg gtc aag gca acg gcc ttc cat ctg aaa ggc aga     2437
Glu Phe Gly Lys Val Val Lys Ala Thr Ala Phe His Leu Lys Gly Arg
735                 740                 745 gca ggg tac acc acg gtg gcc gtg aag atg ctg aaa gag aac gcc tcc     2485
Ala Gly Tyr Thr Thr Val Ala Val Lys Met Leu Lys Glu Asn Ala Ser
750                 755                 760                 765 ccg agt gag ctt cga gac ctg ctg tca gag ttc aac gtc ctg aag cag     2533
Pro Ser Glu Leu Arg Asp Leu Leu Ser Glu Phe Asn Val Leu Lys Gln
            770                 775                 780 gtc aac cac cca cat gtc atc aaa ttg tat ggg gcc tgc agc cag gat     2581
Val Asn His Pro His Val Ile Lys Leu Tyr Gly Ala Cys Ser Gln Asp
                785                 790                 795 ggc ccg ctc ctc ctc atc gtg gag tac gcc aaa tac ggc tcc ctg cgg     2629
Gly Pro Leu Leu Leu Ile Val Glu Tyr Ala Lys Tyr Gly Ser Leu Arg
                800                 805                 810 ggc ttc ctc cgc gag agc cgc aaa gtg ggg cct ggc tac ctg ggc agt     2677
Gly Phe Leu Arg Glu Ser Arg Lys Val Gly Pro Gly Tyr Leu Gly Ser
815                 820                 825 gga ggc agc cgc aac tcc agc tcc ctg gac cac ccg gat gag cgg gcc     2725
Gly Gly Ser Arg Asn Ser Ser Ser Leu Asp His Pro Asp Glu Arg Ala
830                 835                 840                 845 ctc acc atg ggc gac ctc atc tca ttt gcc tgg cag atc tca cag ggg     2773
Leu Thr Met Gly Asp Leu Ile Ser Phe Ala Trp Gln Ile Ser Gln Gly
            850                 855                 860 atg cag tat ctg gcc gag atg aag ctc gtt cat cgg gac ttg gca gcc     2821
Met Gln Tyr Leu Ala Glu Met Lys Leu Val His Arg Asp Leu Ala Ala
                865                 870                 875 aga aac atc ctg gta gct gag ggg cgg aag atg aag att tcg gat ttc     2869
Arg Asn Ile Leu Val Ala Glu Gly Arg Lys Met Lys Ile Ser Asp Phe
                880                 885                 890
```

```
ggc ttg tcc cga gat gtt tat gaa gag gat tcc tac gtg aag agg agc      2917
Gly Leu Ser Arg Asp Val Tyr Glu Glu Asp Ser Tyr Val Lys Arg Ser
    895                 900                 905 cag ggt cgg att cca gtt aaa tgg atg gca att gaa tcc ctt ttt gat      2965
Gln Gly Arg Ile Pro Val Lys Trp Met Ala Ile Glu Ser Leu Phe Asp
910                 915                 920                 925 cat atc tac acc acg caa agt gat gta tgg tct ttt ggt gtc ctg ctg      3013
His Ile Tyr Thr Thr Gln Ser Asp Val Trp Ser Phe Gly Val Leu Leu
                930                 935                 940 tgg gag atc gtg acc cta ggg gga aac ccc tat cct ggg att cct cct      3061
Trp Glu Ile Val Thr Leu Gly Gly Asn Pro Tyr Pro Gly Ile Pro Pro
            945                 950                 955 gag cgg ctc ttc aac ctt ctg aag acc ggc cac cgg atg gag agg cca      3109
Glu Arg Leu Phe Asn Leu Leu Lys Thr Gly His Arg Met Glu Arg Pro
        960                 965                 970 gac aac tgc agc gag gag atg tac cgc ctg atg ctg caa tgc tgg aag      3157
Asp Asn Cys Ser Glu Glu Met Tyr Arg Leu Met Leu Gln Cys Trp Lys
975                 980                 985 cag gag ccg gac aaa agg ccg gtg ttt gcg gac atc agc aaa gac ctg      3205
Gln Glu Pro Asp Lys Arg Pro Val Phe Ala Asp Ile Ser Lys Asp Leu
990                 995                 1000                1005 gag aag atg atg gtt aag agg aga gac tac ttg gac ctt gcg gcg          3250
Glu Lys Met Met Val Lys Arg Arg Asp Tyr Leu Asp Leu Ala Ala
                1010                1015                1020 tcc act cca tct gac tcc ctg att tat gac gac ggc ctc tca gag          3295
Ser Thr Pro Ser Asp Ser Leu Ile Tyr Asp Asp Gly Leu Ser Glu
            1025                1030                1035 gag gag aca ccg ctg gtg gac tgt aat aat gcc ccc ctc cct cga          3340
Glu Glu Thr Pro Leu Val Asp Cys Asn Asn Ala Pro Leu Pro Arg
        1040                1045                1050 gcc ctc cct tcc aca tgg att gaa aac aaa ctc tat ggc atg tca          3385
Ala Leu Pro Ser Thr Trp Ile Glu Asn Lys Leu Tyr Gly Met Ser
    1055                1060                1065 gac ccg aac tgg cct gga gag agt cct gta cca ctc acg aga gct          3430
Asp Pro Asn Trp Pro Gly Glu Ser Pro Val Pro Leu Thr Arg Ala
1070                1075                1080 gat ggc act aac act ggg ttt cca aga tat cca aat gat agt gta          3475
Asp Gly Thr Asn Thr Gly Phe Pro Arg Tyr Pro Asn Asp Ser Val
                1085                1090                1095 tat gct aac tgg atg ctt tca ccc tca gcg gca aaa tta atg gac          3520
Tyr Ala Asn Trp Met Leu Ser Pro Ser Ala Ala Lys Leu Met Asp
            1100                1105                1110 acg ttt gat agt taa catttctttg tgaaaggtaa tggactcaca aggggaagaa      3575
Thr Phe Asp Ser acatgctgag aatggaaagt ctaccggccc tttctttgtg aacgtcacat tggccgagcc    3635
gtgttcagtt cccaggtggc agactcgttt ttggtagttt gttttaactt ccaaggtggt    3695
tttacttctg atagccggtg attttccctc ctagcagaca tgccacaccg ggtaagagct    3755
ctgagtctta gtggttaagc attcctttct cttcagtgcc cagcagcacc cagtgttggt    3815
ctgtgtccat cagtgaccac caacattctg tgttcacatg tgtgggtcca acacttacta    3875
cctggtgtat gaaattggac ctgaactgtt ggatttttct agttgccgcc aaacaaggca    3935
aaaaaattta aacatgaagc acacacacaa aaaaggcagt aggaaaaatg ctggccctga    3995
tgacctgtcc ttattcagaa tgagagactg cgggggggc ctgggggtag tgtcaatgcc     4055
cctccagggc tggaggggaa gagggcccc gaggatgggc ctgggctcag cattcgagat     4115
cttgagaatg attttttttt aatcatgcaa cctttcctta ggaagacatt tggttttcat    4175
```

```
catgattaag atgattccta gatttagcac aatggagaga ttccatgcca tctttactat    4235
gtggatggtg gtatcaggga agagggctca caagacacat tgtccccccg ggcccaccac    4295
atcatcctca cgtgttcggt actgagcagc cactacccct gatgagaaca gtatgaagaa    4355 aggggggctgt tggagtccca gaattgctga cagcagaggc tttgctgctg tgaatcccac    4415
ctgccaccag cctgcagcac accccacagc caagtagagg cgaaagcagt ggctcatcct    4475
acctgttagg agcaggtagg gcttgtactc actttaattt gaatcttatc aacttactca    4535
taaagggaca ggctagctag ctgtgttaga agtagcaatg acaatgacca aggactgcta    4595
cacctctgat tacaattctg atgtgaaaaa gatggtgttt ggctcttata gagcctgtgt    4655
gaaaggccca tggatcagct cttcctgtgt ttgtaattta atgctgctac aagatgtttc    4715
tgtttcttag attctgacca tgactcataa gcttcttgtc attcttcatt gcttgtttgt    4775
ggtcacagat gcacaacact cctccagtct tgtgggggca gcttttggga agtctcagca    4835
gctcttctgg ctgtgttgtc agcactgtaa cttcgcagaa aagagtcgga ttaccaaaac    4895
actgcctgct cttcagactt aaagcactga taggacttaa aatagtctca ttcaaatact    4955
gtattttata taggcatttc acaaaaacag caaaattgtg gcattttgtg aggccaaggc    5015
ttggatgcgt gtgtaataga gccttgtggt gtgtgcgcac acacccagag ggagagtttg    5075
aaaaatgctt attggacacg taacctggct ctaatttggg ctgtttttca gatacactgt    5135
gataagttct tttacaaata tctatagaca tggtaaactt ttggttttca gatatgctta    5195
atgatagtct tactaaatgc agaaataaga ataaactttc tcaaattatt aaaaatgcct    5255
acacagtaag tgtgaattgc tgcaacaggt ttgttctcag gagggtaaga actccaggtc    5315
taaacagctg acccagtgat ggggaattta tccttgacca atttatcctt gaccaataac    5375
ctaattgtct attcctgagt tataaaagtc cccatcctta ttagctctac tggaattttc    5435
atacacgtaa atgcagaagt tactaagtat taagtattac tgagtattaa gtagtaatct    5495
gtcagttatt aaaatttgta aaatctattt atgaaaggtc attaaaccag atcatgttcc    5555 ttttttttgta atcaaggtga ctaagaaaat cagttgtgta aataaaatca tgtatcataa    5615
aaaaaaaaaa aaaa                                                      5629
```

<210> SEQ ID NO 4
<211> LENGTH: 1114
<212> TYPE: PRT
<213> ORGANISM: Homo sapiens

<400> SEQUENCE: 4

```
Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110
```

-continued

```
Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Gly Thr Arg Pro Ser Phe Arg Ile
                165                 170                 175

Arg Glu Asn Arg Pro Pro Gly Thr Phe His Gln Phe Arg Leu Leu Pro
                180                 185                 190

Val Gln Phe Leu Cys Pro Asn Ile Ser Val Ala Tyr Arg Leu Leu Glu
                195                 200                 205

Gly Glu Gly Leu Pro Phe Arg Cys Ala Pro Asp Ser Leu Glu Val Ser
        210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Val Val Met Val
                245                 250                 255

Pro Phe Pro Val Thr Val Tyr Asp Glu Asp Ser Ala Pro Thr Phe
                260                 265                 270

Pro Ala Gly Val Asp Thr Ala Ser Ala Val Val Glu Phe Lys Arg Lys
                275                 280                 285

Glu Asp Thr Val Val Ala Thr Leu Arg Val Phe Asp Ala Asp Val Val
        290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
                340                 345                 350

Asp Tyr Arg Leu Val Leu Asn Arg Asn Leu Ser Ile Ser Glu Asn Arg
                355                 360                 365

Thr Met Gln Leu Ala Val Leu Val Asn Asp Ser Asp Phe Gln Gly Pro
        370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
                420                 425                 430

Phe Ser Gly Ile Asn Val Gln Tyr Lys Leu His Ser Ser Gly Ala Asn
                435                 440                 445

Cys Ser Thr Leu Gly Val Val Thr Ser Ala Glu Asp Thr Ser Gly Ile
        450                 455                 460

Leu Phe Val Asn Asp Thr Lys Ala Leu Arg Arg Pro Lys Cys Ala Glu
465                 470                 475                 480

Leu His Tyr Met Val Ala Thr Asp Gln Gln Thr Ser Arg Gln Ala
                485                 490                 495

Gln Ala Gln Leu Leu Val Thr Val Glu Gly Ser Tyr Val Ala Glu Glu
        500                 505                 510

Ala Gly Cys Pro Leu Ser Cys Ala Val Ser Lys Arg Arg Leu Glu Cys
                515                 520                 525
```

```
Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
                580                 585                 590

Gly His Glu Pro Gly Glu Pro Arg Gly Ile Lys Ala Gly Tyr Gly Thr
        595                 600                 605

Cys Asn Cys Phe Pro Glu Glu Lys Cys Phe Cys Glu Pro Glu Asp
    610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Ser Ala Phe Cys
                645                 650                 655

Ile His Cys Tyr His Lys Phe Ala His Lys Pro Ile Ser Ser Ala
        660                 665                 670

Glu Met Thr Phe Arg Arg Pro Ala Gln Ala Phe Pro Val Ser Tyr Ser
        675                 680                 685

Ser Ser Gly Ala Arg Arg Pro Ser Leu Asp Ser Met Glu Asn Gln Val
690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
                740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
    770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
                820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
                900                 905                 910

Ile Pro Val Lys Trp Met Ala Ile Glu Ser Leu Phe Asp His Ile Tyr
            915                 920                 925

Thr Thr Gln Ser Asp Val Trp Ser Phe Gly Val Leu Leu Trp Glu Ile
        930                 935                 940

Val Thr Leu Gly Gly Asn Pro Tyr Pro Gly Ile Pro Pro Glu Arg Leu
```

```
945              950              955              960
Phe Asn Leu Leu Lys Thr Gly His Arg Met Glu Arg Pro Asp Asn Cys
                965              970              975

Ser Glu Glu Met Tyr Arg Leu Met Leu Gln Cys Trp Lys Gln Glu Pro
                980              985              990

Asp Lys Arg Pro Val Phe Ala Asp  Ile Ser Lys Asp Leu  Glu Lys Met
        995             1000              1005

Met Val  Lys Arg Arg Asp Tyr  Leu Asp Leu Ala Ala  Ser Thr Pro
    1010             1015             1020

Ser Asp  Ser Leu Ile Tyr Asp  Gly Leu Ser Glu  Glu Thr
    1025             1030             1035

Pro Leu  Val Asp Cys Asn Asn  Ala Pro Leu Pro Arg  Ala Leu Pro
    1040             1045             1050

Ser Thr  Trp Ile Glu Asn Lys  Leu Tyr Gly Met Ser  Asp Pro Asn
    1055             1060             1065

Trp Pro  Gly Glu Ser Pro Val  Pro Leu Thr Arg Ala  Asp Gly Thr
    1070             1075             1080

Asn Thr  Gly Phe Pro Arg Tyr  Pro Asn Asp Ser Val  Tyr Ala Asn
    1085             1090             1095

Trp Met  Leu Ser Pro Ser Ala  Ala Lys Leu Met Asp  Thr Phe Asp
    1100             1105             1110

Ser

<210> SEQ ID NO 5
<211> LENGTH: 5498
<212> TYPE: DNA
<213> ORGANISM: Homo sapiens
<220> FEATURE:
<221> NAME/KEY: CDS
<222> LOCATION: (471)..(3401)
<223> OTHER INFORMATION: KIF5B-RET fusion variant1

<400> SEQUENCE: 5
ctcctcccgc accgccctgt cgcccaacgg cggcctcagg agtgatcggg cagcagtcgg      60
ccggccagcg gacggcagag cgggcggacg ggtaggcccg gcctgctctt cgcgaggagg     120
aagaaggtgg ccactctccc ggtccccaga acctccccag ccccgcagt ccgcccagac      180 cgtaaagggg gacgctgagg agccgcggac gctctccccg gtgccgccgc cgctgccgcc     240
gccatggctg ccatgatgga tcggaagtga gcattagggt taacggctgc cggcgccggc     300
tcttcaagtc ccggctcccc ggccgcctcc acccggggaa gcgcagcgcg gcgcagctga     360
ctgctgcctc tcacggccct cgcgaccaca agccctcagg tccggcgcgt tccctgcaag     420
actgagcggc ggggagtggc tcccggccgc cggccccggc tgcgagaaag atg gcg       476
                                                         Met Ala
                                                          1 gac ctg gcc gag tgc aac atc aaa gtg atg tgt cgc ttc aga cct ctc       524
Asp Leu Ala Glu Cys Asn Ile Lys Val Met Cys Arg Phe Arg Pro Leu
        5                  10                 15 aac gag tct gaa gtg aac cgc ggc gac aag tac atc gcc aag ttt cag       572
Asn Glu Ser Glu Val Asn Arg Gly Asp Lys Tyr Ile Ala Lys Phe Gln
     20                 25                 30 gga gaa gac acg gtc gtg atc gcg tcc aag cct tat gca ttt gat cgg       620
Gly Glu Asp Thr Val Val Ile Ala Ser Lys Pro Tyr Ala Phe Asp Arg
 35                 40                 45                 50 gtg ttc cag tca agc aca tct caa gag caa gtg tat aat gac tgt gca       668
Val Phe Gln Ser Ser Thr Ser Gln Glu Gln Val Tyr Asn Asp Cys Ala
                 55                 60                 65
```

| | | |
|---|---|---|
| aag aag att gtt aaa gat gta ctt gaa gga tat aat gga aca ata ttt<br>Lys Lys Ile Val Lys Asp Val Leu Glu Gly Tyr Asn Gly Thr Ile Phe<br>           70                    75                  80 | 716 |
| gca tat gga caa aca tcc tct ggg aag aca cac aca atg gag ggt aaa<br>Ala Tyr Gly Gln Thr Ser Ser Gly Lys Thr His Thr Met Glu Gly Lys<br>          85                    90                  95 | 764 |
| ctt cat gat cca gaa ggc atg gga att att cca aga ata gtg caa gat<br>Leu His Asp Pro Glu Gly Met Gly Ile Ile Pro Arg Ile Val Gln Asp<br>100                        105                110 | 812 |
| att ttt aat tat att tac tcc atg gat gaa aat ttg gaa ttt cat att<br>Ile Phe Asn Tyr Ile Tyr Ser Met Asp Glu Asn Leu Glu Phe His Ile<br>115                      120                  125              130 | 860 |
| aag gtt tca tat ttt gaa ata tat ttg gat aag ata agg gac ctg tta<br>Lys Val Ser Tyr Phe Glu Ile Tyr Leu Asp Lys Ile Arg Asp Leu Leu<br>                135                  140              145 | 908 |
| gat gtt tca aag acc aac ctt tca gtt cat gaa gac aaa aac cga gtt<br>Asp Val Ser Lys Thr Asn Leu Ser Val His Glu Asp Lys Asn Arg Val<br>          150                    155                160 | 956 |
| ccc tat gta aag ggg tgc aca gag cgt ttt gta tgt agt cca gat gaa<br>Pro Tyr Val Lys Gly Cys Thr Glu Arg Phe Val Cys Ser Pro Asp Glu<br>                165                  170              175 | 1004 |
| gtt atg gat acc ata gat gaa gga aaa tcc aac aga cat gta gca gtt<br>Val Met Asp Thr Ile Asp Glu Gly Lys Ser Asn Arg His Val Ala Val<br>180                        185                190 | 1052 |
| aca aat atg aat gaa cat agc tct agg agt cac agt ata ttt ctt att<br>Thr Asn Met Asn Glu His Ser Ser Arg Ser His Ser Ile Phe Leu Ile<br>195                        200                  205              210 | 1100 |
| aat gtc aaa caa gag aac aca caa acg gaa caa aag ctg agt gga aaa<br>Asn Val Lys Gln Glu Asn Thr Gln Thr Glu Gln Lys Leu Ser Gly Lys<br>                215                  220              225 | 1148 |
| ctt tat ctg gtt gat tta gct ggt agt gaa aag gtt agt aaa act gga<br>Leu Tyr Leu Val Asp Leu Ala Gly Ser Glu Lys Val Ser Lys Thr Gly<br>          230                    235                240 | 1196 |
| gct gaa ggt gct gtg ctg gat gaa gct aaa aac atc aac aag tca ctt<br>Ala Glu Gly Ala Val Leu Asp Glu Ala Lys Asn Ile Asn Lys Ser Leu<br>                245                  250              255 | 1244 |
| tct gct ctt gga aat gtt att tct gct ttg gct gag ggt agt aca tat<br>Ser Ala Leu Gly Asn Val Ile Ser Ala Leu Ala Glu Gly Ser Thr Tyr<br>260                        265                270 | 1292 |
| gtt cca tat cga gat agt aaa atg aca aga atc ctt caa gat tca tta<br>Val Pro Tyr Arg Asp Ser Lys Met Thr Arg Ile Leu Gln Asp Ser Leu<br>275                        280                  285              290 | 1340 |
| ggt ggc aac tgt aga acc act att gta att tgc tgc tct cca tca tca<br>Gly Gly Asn Cys Arg Thr Thr Ile Val Ile Cys Cys Ser Pro Ser Ser<br>                295                  300              305 | 1388 |
| tac aat gag tct gaa aca aaa tct aca ctc tta ttt ggc caa agg gcc<br>Tyr Asn Glu Ser Glu Thr Lys Ser Thr Leu Leu Phe Gly Gln Arg Ala<br>          310                    315                320 | 1436 |
| aaa aca att aag aac aca gtt tgt gtc aat gtg gag tta act gca gaa<br>Lys Thr Ile Lys Asn Thr Val Cys Val Asn Val Glu Leu Thr Ala Glu<br>                325                  330              335 | 1484 |
| cag tgg aaa aag aag tat gaa aaa gaa aaa gaa aaa aat aag atc ctg<br>Gln Trp Lys Lys Lys Tyr Glu Lys Glu Lys Glu Lys Asn Lys Ile Leu<br>340                        345                350 | 1532 |
| cgg aac act att cag tgg ctt gaa aat gag ctc aac aga tgg cgt aat<br>Arg Asn Thr Ile Gln Trp Leu Glu Asn Glu Leu Asn Arg Trp Arg Asn<br>355                        360                  365              370 | 1580 |
| ggg gag acg gtg cct att gat gaa cag ttt gac aaa gag aaa gcc aac<br>Gly Glu Thr Val Pro Ile Asp Glu Gln Phe Asp Lys Glu Lys Ala Asn | 1628 |

|   |   |   |   |   |   |   |   |   |   |   |   |   |   |   |   |      |
|---|---|---|---|---|---|---|---|---|---|---|---|---|---|---|---|------|
|   |   |   | 375 |   |   |   |   | 380 |   |   |   |   | 385 |   |   |      |
| ttg | gaa | gct | ttc | aca | gtg | gat | aaa | gat | att | act | ctt | acc | aat | gat | aaa | 1676 |
| Leu | Glu | Ala | Phe | Thr | Val | Asp | Lys | Asp | Ile | Thr | Leu | Thr | Asn | Asp | Lys |      |
|   |   |   | 390 |   |   |   |   | 395 |   |   |   |   | 400 |   |   |      |
| cca | gca | acc | gca | att | gga | gtt | ata | gga | aat | ttt | act | gat | gct | gaa | aga | 1724 |
| Pro | Ala | Thr | Ala | Ile | Gly | Val | Ile | Gly | Asn | Phe | Thr | Asp | Ala | Glu | Arg |      |
|   |   | 405 |   |   |   |   | 410 |   |   |   |   | 415 |   |   |   |      |
| aga | aag | tgt | gaa | gaa | gaa | att | gct | aaa | tta | tac | aaa | cag | ctt | gat | gac | 1772 |
| Arg | Lys | Cys | Glu | Glu | Glu | Ile | Ala | Lys | Leu | Tyr | Lys | Gln | Leu | Asp | Asp |      |
|   | 420 |   |   |   |   | 425 |   |   |   |   | 430 |   |   |   |   |      |
| aag | gat | gaa | gaa | att | aac | cag | caa | agt | caa | ctg | gta | gag | aaa | ctg | aag | 1820 |
| Lys | Asp | Glu | Glu | Ile | Asn | Gln | Gln | Ser | Gln | Leu | Val | Glu | Lys | Leu | Lys |      |
| 435 |   |   |   |   | 440 |   |   |   |   | 445 |   |   |   |   | 450 |      |
| acg | caa | atg | ttg | gat | cag | gag | gag | ctt | ttg | gca | tct | acc | aga | agg | gat | 1868 |
| Thr | Gln | Met | Leu | Asp | Gln | Glu | Glu | Leu | Leu | Ala | Ser | Thr | Arg | Arg | Asp |      |
|   |   |   |   | 455 |   |   |   |   | 460 |   |   |   |   | 465 |   |      |
| caa | gac | aat | atg | caa | gct | gag | ctg | aat | cgc | ctt | caa | gca | gaa | aat | gat | 1916 |
| Gln | Asp | Asn | Met | Gln | Ala | Glu | Leu | Asn | Arg | Leu | Gln | Ala | Glu | Asn | Asp |      |
|   |   |   | 470 |   |   |   |   | 475 |   |   |   |   | 480 |   |   |      |
| gcc | tct | aaa | gaa | gaa | gtg | aaa | gaa | gtt | tta | cag | gcc | cta | gaa | gaa | ctt | 1964 |
| Ala | Ser | Lys | Glu | Glu | Val | Lys | Glu | Val | Leu | Gln | Ala | Leu | Glu | Glu | Leu |      |
|   |   | 485 |   |   |   |   | 490 |   |   |   |   | 495 |   |   |   |      |
| gct | gtc | aat | tat | gat | cag | aag | tct | cag | gaa | gtt | gaa | gac | aaa | act | aag | 2012 |
| Ala | Val | Asn | Tyr | Asp | Gln | Lys | Ser | Gln | Glu | Val | Glu | Asp | Lys | Thr | Lys |      |
|   | 500 |   |   |   |   | 505 |   |   |   |   | 510 |   |   |   |   |      |
| gaa | tat | gaa | ttg | ctt | agt | gat | gaa | ttg | aat | cag | aaa | tcg | gca | act | tta | 2060 |
| Glu | Tyr | Glu | Leu | Leu | Ser | Asp | Glu | Leu | Asn | Gln | Lys | Ser | Ala | Thr | Leu |      |
| 515 |   |   |   |   | 520 |   |   |   |   | 525 |   |   |   |   | 530 |      |
| gcg | agt | ata | gat | gct | gag | ctt | cag | aaa | ctt | aag | gaa | atg | acc | aac | cac | 2108 |
| Ala | Ser | Ile | Asp | Ala | Glu | Leu | Gln | Lys | Leu | Lys | Glu | Met | Thr | Asn | His |      |
|   |   |   |   | 535 |   |   |   |   | 540 |   |   |   |   | 545 |   |      |
| cag | aaa | aaa | cga | gca | gct | gag | atg | atg | gca | tct | tta | cta | aaa | gac | ctt | 2156 |
| Gln | Lys | Lys | Arg | Ala | Ala | Glu | Met | Met | Ala | Ser | Leu | Leu | Lys | Asp | Leu |      |
|   |   |   | 550 |   |   |   |   | 555 |   |   |   |   | 560 |   |   |      |
| gca | gaa | ata | gga | att | gct | gtg | gga | aat | aat | gat | gta | aag | gag | gat | cca | 2204 |
| Ala | Glu | Ile | Gly | Ile | Ala | Val | Gly | Asn | Asn | Asp | Val | Lys | Glu | Asp | Pro |      |
|   |   | 565 |   |   |   |   | 570 |   |   |   |   | 575 |   |   |   |      |
| aag | tgg | gaa | ttc | cct | cgg | aag | aac | ttg | gtt | ctt | gga | aaa | act | cta | gga | 2252 |
| Lys | Trp | Glu | Phe | Pro | Arg | Lys | Asn | Leu | Val | Leu | Gly | Lys | Thr | Leu | Gly |      |
|   | 580 |   |   |   |   | 585 |   |   |   |   | 590 |   |   |   |   |      |
| gaa | ggc | gaa | ttt | gga | aaa | gtg | gtc | aag | gca | acg | gcc | ttc | cat | ctg | aaa | 2300 |
| Glu | Gly | Glu | Phe | Gly | Lys | Val | Val | Lys | Ala | Thr | Ala | Phe | His | Leu | Lys |      |
| 595 |   |   |   |   | 600 |   |   |   |   | 605 |   |   |   |   | 610 |      |
| ggc | aga | gca | ggg | tac | acc | acg | gtg | gcc | gtg | aag | atg | ctg | aaa | gag | aac | 2348 |
| Gly | Arg | Ala | Gly | Tyr | Thr | Thr | Val | Ala | Val | Lys | Met | Leu | Lys | Glu | Asn |      |
|   |   |   |   | 615 |   |   |   |   | 620 |   |   |   |   | 625 |   |      |
| gcc | tcc | ccg | agt | gag | ctt | cga | gac | ctg | ctg | tca | gag | ttc | aac | gtc | ctg | 2396 |
| Ala | Ser | Pro | Ser | Glu | Leu | Arg | Asp | Leu | Leu | Ser | Glu | Phe | Asn | Val | Leu |      |
|   |   |   | 630 |   |   |   |   | 635 |   |   |   |   | 640 |   |   |      |
| aag | cag | gtc | aac | cac | cca | cat | gtc | atc | aaa | ttg | tat | ggg | gcc | tgc | agc | 2444 |
| Lys | Gln | Val | Asn | His | Pro | His | Val | Ile | Lys | Leu | Tyr | Gly | Ala | Cys | Ser |      |
|   |   | 645 |   |   |   |   | 650 |   |   |   |   | 655 |   |   |   |      |
| cag | gat | ggc | ccg | ctc | ctc | ctc | atc | gtg | gag | tac | gcc | aaa | tac | ggc | tcc | 2492 |
| Gln | Asp | Gly | Pro | Leu | Leu | Leu | Ile | Val | Glu | Tyr | Ala | Lys | Tyr | Gly | Ser |      |
|   | 660 |   |   |   |   | 665 |   |   |   |   | 670 |   |   |   |   |      |
| ctg | cgg | ggc | ttc | ctc | cgc | gag | agc | cgc | aaa | gtg | ggg | cct | ggc | tac | ctg | 2540 |
| Leu | Arg | Gly | Phe | Leu | Arg | Glu | Ser | Arg | Lys | Val | Gly | Pro | Gly | Tyr | Leu |      |
| 675 |   |   |   |   | 680 |   |   |   |   | 685 |   |   |   |   | 690 |      |
| ggc | agt | gga | ggc | agc | cgc | aac | tcc | agc | tcc | ctg | gac | cac | ccg | gat | gag | 2588 |

```
                  Gly Ser Gly Gly Ser Arg Asn Ser Ser Ser Leu Asp His Pro Asp Glu
                              695                 700                 705 cgg gcc ctc acc atg ggc gac ctc atc tca ttt gcc tgg cag atc tca        2636
Arg Ala Leu Thr Met Gly Asp Leu Ile Ser Phe Ala Trp Gln Ile Ser
            710                 715                 720 cag ggg atg cag tat ctg gcc gag atg aag ctc gtt cat cgg gac ttg        2684
Gln Gly Met Gln Tyr Leu Ala Glu Met Lys Leu Val His Arg Asp Leu
        725                 730                 735 gca gcc aga aac atc ctg gta gct gag ggg cgg aag atg aag att tcg        2732
Ala Ala Arg Asn Ile Leu Val Ala Glu Gly Arg Lys Met Lys Ile Ser
    740                 745                 750 gat ttc ggc ttg tcc cga gat gtt tat gaa gag gat tcc tac gtg aag        2780
Asp Phe Gly Leu Ser Arg Asp Val Tyr Glu Glu Asp Ser Tyr Val Lys
755                 760                 765                 770 agg agc cag ggt cgg att cca gtt aaa tgg atg gca att gaa tcc ctt        2828
Arg Ser Gln Gly Arg Ile Pro Val Lys Trp Met Ala Ile Glu Ser Leu
                775                 780                 785 ttt gat cat atc tac acc acg caa agt gat gta tgg tct ttt ggt gtc        2876
Phe Asp His Ile Tyr Thr Thr Gln Ser Asp Val Trp Ser Phe Gly Val
            790                 795                 800 ctg ctg tgg gag atc gtg acc cta ggg gga aac ccc tat cct ggg att        2924
Leu Leu Trp Glu Ile Val Thr Leu Gly Gly Asn Pro Tyr Pro Gly Ile
        805                 810                 815 cct cct gag cgg ctc ttc aac ctt ctg aag acc ggc cac cgg atg gag        2972
Pro Pro Glu Arg Leu Phe Asn Leu Leu Lys Thr Gly His Arg Met Glu
    820                 825                 830 agg cca gac aac tgc agc gag gag atg tac cgc ctg atg ctg caa tgc        3020
Arg Pro Asp Asn Cys Ser Glu Glu Met Tyr Arg Leu Met Leu Gln Cys
835                 840                 845                 850 tgg aag cag gag ccg gac aaa agg ccg gtg ttt gcg gac atc agc aaa        3068
Trp Lys Gln Glu Pro Asp Lys Arg Pro Val Phe Ala Asp Ile Ser Lys
                855                 860                 865 gac ctg gag aag atg atg gtt aag agg aga gac tac ttg gac ctt gcg        3116
Asp Leu Glu Lys Met Met Val Lys Arg Arg Asp Tyr Leu Asp Leu Ala
            870                 875                 880 gcg tcc act cca tct gac tcc ctg att tat gac gac ggc ctc tca gag        3164
Ala Ser Thr Pro Ser Asp Ser Leu Ile Tyr Asp Asp Gly Leu Ser Glu
        885                 890                 895 gag gag aca ccg ctg gtg gac tgt aat aat gcc ccc ctc cct cga gcc        3212
Glu Glu Thr Pro Leu Val Asp Cys Asn Asn Ala Pro Leu Pro Arg Ala
    900                 905                 910 ctc cct tcc aca tgg att gaa aac aaa ctc tat ggc atg tca gac ccg        3260
Leu Pro Ser Thr Trp Ile Glu Asn Lys Leu Tyr Gly Met Ser Asp Pro
915                 920                 925                 930 aac tgg cct gga gag agt cct gta cca ctc acg aga gct gat ggc act        3308
Asn Trp Pro Gly Glu Ser Pro Val Pro Leu Thr Arg Ala Asp Gly Thr
                935                 940                 945 aac act ggg ttt cca aga tat cca aat gat agt gta tat gct aac tgg        3356
Asn Thr Gly Phe Pro Arg Tyr Pro Asn Asp Ser Val Tyr Ala Asn Trp
            950                 955                 960 atg ctt tca ccc tca gcg gca aaa tta atg gac acg ttt gat agt            3401
Met Leu Ser Pro Ser Ala Ala Lys Leu Met Asp Thr Phe Asp Ser
        965                 970                 975 taacatttct ttgtgaaagg taatggactc acaaggggaa gaaacatgct gagaatggaa      3461
agtctaccgg cccttttcttt gtgaacgtca cattggccga gccgtgttca gttcccaggt    3521
ggcagactcg ttttttggtag tttgttttaa cttccaaggt ggttttactt ctgatagccg    3581 gtgatttttcc ctcctagcag acatgccaca ccgggtaaga gctctgagtc ttagtggtta   3641
```

-continued

```
agcattcctt tctcttcagt gcccagcagc acccagtgtt ggtctgtgtc catcagtgac   3701
caccaacatt ctgtgttcac atgtgtgggt ccaacactta ctacctggtg tatgaaattg   3761
gacctgaact gttggatttt tctagttgcc gccaaacaag gcaaaaaaat ttaaacatga   3821
agcacacaca caaaaaaggc agtaggaaaa atgctggccc tgatgacctg tccttattca   3881
gaatgagaga ctgcgggggg ggcctggggg tagtgtcaat gcccctccag ggctggaggg   3941
gaagaggggc cccgaggatg ggcctgggct cagcattcga gatcttgaga atgatttttt   4001
tttaatcatg caacctttcc ttaggaagac atttggtttt catcatgatt aagatgattc   4061
ctagatttag cacaatggag agattccatg ccatctttac tatgtggatg gtggtatcag   4121
ggaagagggc tcacaagaca catttgtccc ccgggcccac cacatcatcc tcacgtgttc   4181
ggtactgagc agccactacc cctgatgaga acagtatgaa gaaagggggc tgttggagtc   4241
ccagaattgc tgacagcaga ggctttgctg ctgtgaatcc cacctgccac cagcctgcag   4301
cacaccccac agccaagtag aggcgaaagc agtggctcat cctacctgtt aggagcaggt   4361
agggcttgta ctcactttaa tttgaatctt atcaacttac tcataaaggg acaggctagc   4421
tagctgtgtt agaagtagca atgacaatga ccaaggactg ctacacctct gattacaatt   4481
ctgatgtgaa aaagatggtg tttggctctt atagagcctg tgtgaaaggc ccatggatca   4541
gctcttcctg tgtttgtaat ttaatgctgc tacaagatgt ttctgtttct tagattctga   4601
ccatgactca taagcttctt gtcattcttc attgcttgtt tgtggtcaca gatgcacaac   4661
actcctccag tcttgtgggg gcagcttttg ggaagtctca gcagctcttc tggctgtgtt   4721
gtcagcactg taacttcgca gaaaagagtc ggattaccaa aacactgcct gctcttcaga   4781
cttaaagcac tgataggact taaaatagtc tcattcaaat actgtatttt atataggcat   4841
ttcacaaaaa cagcaaaatt gtggcatttt gtgaggccaa ggcttggatg cgtgtgtaat   4901
agagccttgt ggtgtgtgcg cacacaccca gagggagagt ttgaaaaatg cttattggac   4961
acgtaacctg gctctaattt gggctgtttt tcagatacac tgtgataagt tcttttacaa   5021
atatctatag acatggtaaa cttttggttt tcagatatgc ttaatgatag tcttactaaa   5081
tgcagaaata agaataaact ttctcaaatt attaaaaatg cctacacagt aagtgtgaat   5141
tgctgcaaca ggtttgttct caggagggta agaactccag gtctaaacag ctgacccagt   5201
gatggggaat ttatccttga ccaatttatc cttgaccaat aacctaattg tctattcctg   5261
agttataaaa gtccccatcc ttattagctc tactggaatt ttcatacacg taaatgcaga   5321
agttactaag tattaagtat tactgagtat taagtagtaa tctgtcagtt attaaaattt   5381
gtaaaatcta tttatgaaag gtcattaaac cagatcatgt tccttttttt gtaatcaagg   5441
tgactaagaa aatcagttgt gtaaataaaa tcatgtatca taaaaaaaaa aaaaaaa      5498
```

<210> SEQ ID NO 6
<211> LENGTH: 977
<212> TYPE: PRT
<213> ORGANISM: Homo sapiens

<400> SEQUENCE: 6
```

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45
```

-continued

```
Asp Arg Val Phe Gln Ser Ser Thr Ser Gln Glu Gln Val Tyr Asn Asp
     50                  55                  60

Cys Ala Lys Lys Ile Val Lys Asp Val Leu Glu Gly Tyr Asn Gly Thr
 65                  70                  75                  80

Ile Phe Ala Tyr Gly Gln Thr Ser Ser Gly Lys Thr His Thr Met Glu
                     85                  90                  95

Gly Lys Leu His Asp Pro Glu Gly Met Gly Ile Ile Pro Arg Ile Val
                100                 105                 110

Gln Asp Ile Phe Asn Tyr Ile Tyr Ser Met Asp Glu Asn Leu Glu Phe
            115                 120                 125

His Ile Lys Val Ser Tyr Phe Glu Ile Tyr Leu Asp Lys Ile Arg Asp
        130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
```

```
         465                 470                 475                 480
Asn Asp Ala Ser Lys Glu Glu Val Lys Glu Val Leu Gln Ala Leu Glu
                    485                 490                 495
Glu Leu Ala Val Asn Tyr Asp Gln Lys Ser Gln Val Glu Asp Lys
            500                 505                 510
Thr Lys Glu Tyr Glu Leu Leu Ser Asp Glu Leu Asn Gln Lys Ser Ala
                515                 520                 525
Thr Leu Ala Ser Ile Asp Ala Glu Leu Gln Lys Leu Lys Glu Met Thr
        530                 535                 540
Asn His Gln Lys Lys Arg Ala Ala Glu Met Met Ala Ser Leu Leu Lys
545                 550                 555                 560
Asp Leu Ala Glu Ile Gly Ile Ala Val Gly Asn Asn Asp Val Lys Glu
                565                 570                 575
Asp Pro Lys Trp Glu Phe Pro Arg Lys Asn Leu Val Leu Gly Lys Thr
                580                 585                 590
Leu Gly Glu Gly Glu Phe Gly Lys Val Val Lys Ala Thr Ala Phe His
            595                 600                 605
Leu Lys Gly Arg Ala Gly Tyr Thr Thr Val Ala Val Lys Met Leu Lys
        610                 615                 620
Glu Asn Ala Ser Pro Ser Glu Leu Arg Asp Leu Leu Ser Glu Phe Asn
625                 630                 635                 640
Val Leu Lys Gln Val Asn His Pro His Val Ile Lys Leu Tyr Gly Ala
                645                 650                 655
Cys Ser Gln Asp Gly Pro Leu Leu Leu Ile Val Glu Tyr Ala Lys Tyr
                660                 665                 670
Gly Ser Leu Arg Gly Phe Leu Arg Glu Ser Arg Lys Val Gly Pro Gly
            675                 680                 685
Tyr Leu Gly Ser Gly Gly Ser Arg Asn Ser Ser Leu Asp His Pro
        690                 695                 700
Asp Glu Arg Ala Leu Thr Met Gly Asp Leu Ile Ser Phe Ala Trp Gln
705                 710                 715                 720
Ile Ser Gln Gly Met Gln Tyr Leu Ala Glu Met Lys Leu Val His Arg
                725                 730                 735
Asp Leu Ala Ala Arg Asn Ile Leu Val Ala Glu Gly Arg Lys Met Lys
                740                 745                 750
Ile Ser Asp Phe Gly Leu Ser Arg Asp Val Tyr Glu Glu Asp Ser Tyr
            755                 760                 765
Val Lys Arg Ser Gln Gly Arg Ile Pro Val Lys Trp Met Ala Ile Glu
        770                 775                 780
Ser Leu Phe Asp His Ile Tyr Thr Thr Gln Ser Asp Val Trp Ser Phe
785                 790                 795                 800
Gly Val Leu Leu Trp Glu Ile Val Thr Leu Gly Gly Asn Pro Tyr Pro
                805                 810                 815
Gly Ile Pro Pro Glu Arg Leu Phe Asn Leu Leu Lys Thr Gly His Arg
            820                 825                 830
Met Glu Arg Pro Asp Asn Cys Ser Glu Glu Met Tyr Arg Leu Met Leu
        835                 840                 845
Gln Cys Trp Lys Gln Glu Pro Asp Lys Arg Pro Val Phe Ala Asp Ile
850                 855                 860
Ser Lys Asp Leu Glu Lys Met Met Val Lys Arg Arg Asp Tyr Leu Asp
865                 870                 875                 880
Leu Ala Ala Ser Thr Pro Ser Asp Ser Leu Ile Tyr Asp Asp Gly Leu
                885                 890                 895
```

```
Ser Glu Glu Glu Thr Pro Leu Val Asp Cys Asn Asn Ala Pro Leu Pro
            900                 905                 910

Arg Ala Leu Pro Ser Thr Trp Ile Glu Asn Lys Leu Tyr Gly Met Ser
        915                 920                 925

Asp Pro Asn Trp Pro Gly Glu Ser Pro Val Pro Leu Thr Arg Ala Asp
    930                 935                 940

Gly Thr Asn Thr Gly Phe Pro Arg Tyr Pro Asn Asp Ser Val Tyr Ala
945                 950                 955                 960

Asn Trp Met Leu Ser Pro Ser Ala Ala Lys Leu Met Asp Thr Phe Asp
                965                 970                 975

Ser

<210> SEQ ID NO 7
<211> LENGTH: 5687
<212> TYPE: DNA
<213> ORGANISM: Homo sapiens
<220> FEATURE:
<221> NAME/KEY: CDS
<222> LOCATION: (471)..(3590)
<223> OTHER INFORMATION: KIF5B-RET fusion variant2

<400> SEQUENCE: 7
ctcctcccgc accgccctgt cgcccaacgg cggcctcagg agtgatcggg cagcagtcgg      60
ccggccagcg gacggcagag cgggcggacg ggtaggcccg gcctgctctt cgcgaggagg     120
aagaaggtgg ccactctccc ggtccccaga acctccccag ccccgcagt ccgcccagac      180 cgtaaagggg gacgctgagg agccgcggac gctctccccg gtgccgccgc cgctgccgcc     240
gccatggctg ccatgatgga tcggaagtga gcattagggt taacggctgc cggcgccggc     300
tcttcaagtc ccggctcccc ggccgcctcc acccggggaa gcgcagcgcg gcgcagctga     360
ctgctgcctc tcacggccct cgcgaccaca agccctcagg tccggcgcgt tccctgcaag     420
actgagcggc ggggagtggc tcccggccgc cggccccggc tgcagaaaag atg gcg       476
                                                         Met Ala
                                                           1 gac ctg gcc gag tgc aac atc aaa gtg atg tgt cgc ttc aga cct ctc      524
Asp Leu Ala Glu Cys Asn Ile Lys Val Met Cys Arg Phe Arg Pro Leu
        5                   10                  15 aac gag tct gaa gtg aac cgc ggc gac aag tac atc gcc aag ttt cag     572
Asn Glu Ser Glu Val Asn Arg Gly Asp Lys Tyr Ile Ala Lys Phe Gln
    20                  25                  30 gga gaa gac acg gtc gtg atc gcg tcc aag cct tat gca ttt gat cgg     620
Gly Glu Asp Thr Val Val Ile Ala Ser Lys Pro Tyr Ala Phe Asp Arg
35                  40                  45                  50 gtg ttc cag tca agc aca tct caa gag caa gtg tat aat gac tgt gca     668
Val Phe Gln Ser Ser Thr Ser Gln Glu Gln Val Tyr Asn Asp Cys Ala
                55                  60                  65 aag aag att gtt aaa gat gta ctt gaa gga tat aat gga aca ata ttt     716
Lys Lys Ile Val Lys Asp Val Leu Glu Gly Tyr Asn Gly Thr Ile Phe
            70                  75                  80 gca tat gga caa aca tcc tct ggg aag aca cac aca atg gag ggt aaa     764
Ala Tyr Gly Gln Thr Ser Ser Gly Lys Thr His Thr Met Glu Gly Lys
        85                  90                  95 ctt cat gat cca gaa ggc atg gga att att cca aga ata gtg caa gat     812
Leu His Asp Pro Glu Gly Met Gly Ile Ile Pro Arg Ile Val Gln Asp
    100                 105                 110 att ttt aat tat att tac tcc atg gat gaa aat ttg gaa ttt cat att    860
Ile Phe Asn Tyr Ile Tyr Ser Met Asp Glu Asn Leu Glu Phe His Ile
115                 120                 125                 130
```

-continued

```
aag gtt tca tat ttt gaa ata tat ttg gat aag ata agg gac ctg tta     908
Lys Val Ser Tyr Phe Glu Ile Tyr Leu Asp Lys Ile Arg Asp Leu Leu
            135                 140                 145 gat gtt tca aag acc aac ctt tca gtt cat gaa gac aaa aac cga gtt     956
Asp Val Ser Lys Thr Asn Leu Ser Val His Glu Asp Lys Asn Arg Val
        150                 155                 160 ccc tat gta aag ggg tgc aca gag cgt ttt gta tgt agt cca gat gaa    1004
Pro Tyr Val Lys Gly Cys Thr Glu Arg Phe Val Cys Ser Pro Asp Glu
            165                 170                 175 gtt atg gat acc ata gat gaa gga aaa tcc aac aga cat gta gca gtt    1052
Val Met Asp Thr Ile Asp Glu Gly Lys Ser Asn Arg His Val Ala Val
        180                 185                 190 aca aat atg aat gaa cat agc tct agg agt cac agt ata ttt ctt att    1100
Thr Asn Met Asn Glu His Ser Ser Arg Ser His Ser Ile Phe Leu Ile
195                 200                 205                 210 aat gtc aaa caa gag aac aca caa acg gaa caa aag ctg agt gga aaa    1148
Asn Val Lys Gln Glu Asn Thr Gln Thr Glu Gln Lys Leu Ser Gly Lys
                215                 220                 225 ctt tat ctg gtt gat tta gct ggt agt gaa aag gtt agt aaa act gga    1196
Leu Tyr Leu Val Asp Leu Ala Gly Ser Glu Lys Val Ser Lys Thr Gly
            230                 235                 240 gct gaa ggt gct gtg ctg gat gaa gct aaa aac atc aac aag tca ctt    1244
Ala Glu Gly Ala Val Leu Asp Glu Ala Lys Asn Ile Asn Lys Ser Leu
        245                 250                 255 tct gct ctt gga aat gtt att tct gct ttg gct gag ggt agt aca tat    1292
Ser Ala Leu Gly Asn Val Ile Ser Ala Leu Ala Glu Gly Ser Thr Tyr
    260                 265                 270 gtt cca tat cga gat agt aaa atg aca aga atc ctt caa gat tca tta    1340
Val Pro Tyr Arg Asp Ser Lys Met Thr Arg Ile Leu Gln Asp Ser Leu
275                 280                 285                 290 ggt ggc aac tgt aga acc act att gta att tgc tgc tct cca tca tca    1388
Gly Gly Asn Cys Arg Thr Thr Ile Val Ile Cys Cys Ser Pro Ser Ser
                295                 300                 305 tac aat gag tct gaa aca aaa tct aca ctc tta ttt ggc caa agg gcc    1436
Tyr Asn Glu Ser Glu Thr Lys Ser Thr Leu Leu Phe Gly Gln Arg Ala
            310                 315                 320 aaa aca att aag aac aca gtt tgt gtc aat gtg gag tta act gca gaa    1484
Lys Thr Ile Lys Asn Thr Val Cys Val Asn Val Glu Leu Thr Ala Glu
        325                 330                 335 cag tgg aaa aag aag tat gaa aaa gaa aaa gaa aaa aat aag atc ctg    1532
Gln Trp Lys Lys Lys Tyr Glu Lys Glu Lys Glu Lys Asn Lys Ile Leu
    340                 345                 350 cgg aac act att cag tgg ctt gaa aat gag ctc aac aga tgg cgt aat    1580
Arg Asn Thr Ile Gln Trp Leu Glu Asn Glu Leu Asn Arg Trp Arg Asn
355                 360                 365                 370 ggg gag acg gtg cct att gat gaa cag ttt gac aaa gag aaa gcc aac    1628
Gly Glu Thr Val Pro Ile Asp Glu Gln Phe Asp Lys Glu Lys Ala Asn
                375                 380                 385 ttg gaa gct ttc aca gtg gat aaa gat att act ctt acc aat gat aaa    1676
Leu Glu Ala Phe Thr Val Asp Lys Asp Ile Thr Leu Thr Asn Asp Lys
            390                 395                 400 cca gca acc gca att gga gtt ata gga aat ttt act gat gct gaa aga    1724
Pro Ala Thr Ala Ile Gly Val Ile Gly Asn Phe Thr Asp Ala Glu Arg
        405                 410                 415 aga aag tgt gaa gaa gaa att gct aaa tta tac aaa cag ctt gat gac    1772
Arg Lys Cys Glu Glu Glu Ile Ala Lys Leu Tyr Lys Gln Leu Asp Asp
    420                 425                 430 aag gat gaa gaa att aac cag caa agt caa ctg gta gag aaa ctg aag    1820
Lys Asp Glu Glu Ile Asn Gln Gln Ser Gln Leu Val Glu Lys Leu Lys
```

```
                             435                 440                 445                 450
acg caa atg ttg gat cag gag gag ctt ttg gca tct acc aga agg gat              1868
Thr Gln Met Leu Asp Gln Glu Glu Leu Leu Ala Ser Thr Arg Arg Asp
                 455                 460                 465 caa gac aat atg caa gct gag ctg aat cgc ctt caa gca gaa aat gat              1916
Gln Asp Asn Met Gln Ala Glu Leu Asn Arg Leu Gln Ala Glu Asn Asp
         470                 475                 480 gcc tct aaa gaa gaa gtg aaa gaa gtt tta cag gcc cta gaa gaa ctt              1964
Ala Ser Lys Glu Glu Val Lys Glu Val Leu Gln Ala Leu Glu Glu Leu
                 485                 490                 495 gct gtc aat tat gat cag aag tct cag gaa gtt gaa gac aaa act aag              2012
Ala Val Asn Tyr Asp Gln Lys Ser Gln Glu Val Glu Asp Lys Thr Lys
     500                 505                 510 gaa tat gaa ttg ctt agt gat gaa ttg aat cag aaa tcg gca act tta              2060
Glu Tyr Glu Leu Leu Ser Asp Glu Leu Asn Gln Lys Ser Ala Thr Leu
515                 520                 525                 530 gcg agt ata gat gct gag ctt cag aaa ctt aag gaa atg acc aac cac              2108
Ala Ser Ile Asp Ala Glu Leu Gln Lys Leu Lys Glu Met Thr Asn His
                 535                 540                 545 cag aaa aaa cga gca gct gag atg atg gca tct tta cta aaa gac ctt              2156
Gln Lys Lys Arg Ala Ala Glu Met Met Ala Ser Leu Leu Lys Asp Leu
         550                 555                 560 gca gaa ata gga att gct gtg gga aat aat gat gta aag cag cct gag              2204
Ala Glu Ile Gly Ile Ala Val Gly Asn Asn Asp Val Lys Gln Pro Glu
                 565                 570                 575 gga act ggc atg ata gat gaa gag ttc act gtt gca aga ctc tac att              2252
Gly Thr Gly Met Ile Asp Glu Glu Phe Thr Val Ala Arg Leu Tyr Ile
     580                 585                 590 agc aaa atg aag tca gaa gta aaa acc atg gtg aaa cgt tgc aag cag              2300
Ser Lys Met Lys Ser Glu Val Lys Thr Met Val Lys Arg Cys Lys Gln
595                 600                 605                 610 tta gaa agc aca caa act gag agc aac aaa aaa atg gaa gaa aat gaa              2348
Leu Glu Ser Thr Gln Thr Glu Ser Asn Lys Lys Met Glu Glu Asn Glu
                 615                 620                 625 aag gag tta gca gca tgt cag ctt cgt atc tct caa gag gat cca aag              2396
Lys Glu Leu Ala Ala Cys Gln Leu Arg Ile Ser Gln Glu Asp Pro Lys
         630                 635                 640 tgg gaa ttc cct cgg aag aac ttg gtt ctt gga aaa act cta gga gaa              2444
Trp Glu Phe Pro Arg Lys Asn Leu Val Leu Gly Lys Thr Leu Gly Glu
                 645                 650                 655 ggc gaa ttt gga aaa gtg gtc aag gca acg gcc ttc cat ctg aaa ggc              2492
Gly Glu Phe Gly Lys Val Val Lys Ala Thr Ala Phe His Leu Lys Gly
     660                 665                 670 aga gca ggg tac acc acg gtg gcc gtg aag atg ctg aaa gag aac gcc              2540
Arg Ala Gly Tyr Thr Thr Val Ala Val Lys Met Leu Lys Glu Asn Ala
675                 680                 685                 690 tcc ccg agt gag ctt cga gac ctg ctg tca gag ttc aac gtc ctg aag              2588
Ser Pro Ser Glu Leu Arg Asp Leu Leu Ser Glu Phe Asn Val Leu Lys
                 695                 700                 705 cag gtc aac cac cca cat gtc atc aaa ttg tat ggg gcc tgc agc cag              2636
Gln Val Asn His Pro His Val Ile Lys Leu Tyr Gly Ala Cys Ser Gln
         710                 715                 720 gat ggc ccg ctc ctc ctc atc gtg gag tac gcc aaa tac ggc tcc ctg              2684
Asp Gly Pro Leu Leu Leu Ile Val Glu Tyr Ala Lys Tyr Gly Ser Leu
                 725                 730                 735 cgg ggc ttc ctc cgc gag agc cgc aaa gtg ggg cct ggc tac ctg ggc              2732
Arg Gly Phe Leu Arg Glu Ser Arg Lys Val Gly Pro Gly Tyr Leu Gly
     740                 745                 750 agt gga ggc agc cgc aac tcc agc tcc ctg gac cac ccg gat gag cgg              2780
```

```
Ser Gly Gly Ser Arg Asn Ser Ser Ser Leu Asp His Pro Asp Glu Arg
755                 760                 765                 770 gcc ctc acc atg ggc gac ctc atc tca ttt gcc tgg cag atc tca cag    2828
Ala Leu Thr Met Gly Asp Leu Ile Ser Phe Ala Trp Gln Ile Ser Gln
            775                 780                 785 ggg atg cag tat ctg gcc gag atg aag ctc gtt cat cgg gac ttg gca    2876
Gly Met Gln Tyr Leu Ala Glu Met Lys Leu Val His Arg Asp Leu Ala
        790                 795                 800 gcc aga aac atc ctg gta gct gag ggg cgg aag atg aag att tcg gat    2924
Ala Arg Asn Ile Leu Val Ala Glu Gly Arg Lys Met Lys Ile Ser Asp
        805                 810                 815 ttc ggc ttg tcc cga gat gtt tat gaa gag gat tcc tac gtg aag agg    2972
Phe Gly Leu Ser Arg Asp Val Tyr Glu Glu Asp Ser Tyr Val Lys Arg
        820                 825                 830 agc cag ggt cgg att cca gtt aaa tgg atg gca att gaa tcc ctt ttt    3020
Ser Gln Gly Arg Ile Pro Val Lys Trp Met Ala Ile Glu Ser Leu Phe
835                 840                 845                 850 gat cat atc tac acc acg caa agt gat gta tgg tct ttt ggt gtc ctg    3068
Asp His Ile Tyr Thr Thr Gln Ser Asp Val Trp Ser Phe Gly Val Leu
            855                 860                 865 ctg tgg gag atc gtg acc cta ggg gga aac ccc tat cct ggg att cct    3116
Leu Trp Glu Ile Val Thr Leu Gly Gly Asn Pro Tyr Pro Gly Ile Pro
        870                 875                 880 cct gag cgg ctc ttc aac ctt ctg aag acc ggc cac cgg atg gag agg    3164
Pro Glu Arg Leu Phe Asn Leu Leu Lys Thr Gly His Arg Met Glu Arg
        885                 890                 895 cca gac aac tgc agc gag gag atg tac cgc ctg atg ctg caa tgc tgg    3212
Pro Asp Asn Cys Ser Glu Glu Met Tyr Arg Leu Met Leu Gln Cys Trp
900                 905                 910 aag cag gag ccg gac aaa agg ccg gtg ttt gcg gac atc agc aaa gac    3260
Lys Gln Glu Pro Asp Lys Arg Pro Val Phe Ala Asp Ile Ser Lys Asp
915                 920                 925                 930 ctg gag aag atg atg gtt aag agg aga gac tac ttg gac ctt gcg gcg    3308
Leu Glu Lys Met Met Val Lys Arg Arg Asp Tyr Leu Asp Leu Ala Ala
                935                 940                 945 tcc act cca tct gac tcc ctg att tat gac gac ggc ctc tca gag gag    3356
Ser Thr Pro Ser Asp Ser Leu Ile Tyr Asp Asp Gly Leu Ser Glu Glu
            950                 955                 960 gag aca ccg ctg gtg gac tgt aat aat gcc ccc ctc cct cga gcc ctc    3404
Glu Thr Pro Leu Val Asp Cys Asn Asn Ala Pro Leu Pro Arg Ala Leu
        965                 970                 975 cct tcc aca tgg att gaa aac aaa ctc tat ggc atg tca gac ccg aac    3452
Pro Ser Thr Trp Ile Glu Asn Lys Leu Tyr Gly Met Ser Asp Pro Asn
        980                 985                 990 tgg cct gga gag agt cct  gta cca ctc acg aga  gct gat ggc act       3497
Trp Pro Gly Glu Ser Pro  Val Pro Leu Thr Arg  Ala Asp Gly Thr
995                 1000                 1005 aac  act ggg ttt cca aga  tat cca aat gat agt  gta tat gct aac      3542
Asn  Thr Gly Phe Pro Arg  Tyr Pro Asn Asp Ser  Val Tyr Ala Asn
1010                 1015                 1020 tgg  atg ctt tca ccc tca  gcg gca aaa tta atg  gac acg ttt gat      3587
Trp  Met Leu Ser Pro Ser  Ala Ala Lys Leu Met  Asp Thr Phe Asp
1025                 1030                 1035 agt      taacatttct ttgtgaaagg taatggactc acaaggggaa gaaacatgct    3640
Ser
1040 gagaatggaa agtctaccgg ccctttcttt gtgaacgtca cattggccga gccgtgttca    3700 gttcccaggt ggcagactcg tttttggtag tttgttttaa cttccaaggt ggttttactt    3760
```

```
ctgatagccg gtgattttcc ctcctagcag acatgccaca ccgggtaaga gctctgagtc    3820
ttagtggtta agcattcctt tctcttcagt gcccagcagc acccagtgtt ggtctgtgtc    3880
catcagtgac caccaacatt ctgtgttcac atgtgtgggt ccaacactta ctacctggtg    3940
tatgaaattg gacctgaact gttggatttt tctagttgcc gccaaacaag gcaaaaaaat    4000
ttaaacatga agcacacaca caaaaaaggc agtaggaaaa atgctggccc tgatgacctg    4060
tccttattca gaatgagaga ctgcgggggg ggcctggggg tagtgtcaat gcccctccag    4120
ggctggaggg gaagaggggc cccgaggatg ggcctgggct cagcattcga gatcttgaga    4180 atgattttt tttaatcatg caacctttcc ttaggaagac atttggtttt catcatgatt    4240
aagatgattc ctagatttag cacaatggag agattccatg ccatctttac tatgtggatg    4300
gtggtatcag ggaagagggc tcacaagaca catttgtccc ccgggcccac acatcatcc    4360 tcacgtgttc ggtactgagc agccactacc cctgatgaga acagtatgaa gaaggggc    4420 tgttggagtc ccagaattgc tgacagcaga ggctttgctg ctgtgaatcc cacctgccac    4480
cagcctgcag cacaccccac agccaagtag aggcgaaagc agtggctcat cctacctgtt    4540
aggagcaggt agggcttgta ctcactttaa tttgaatctt atcaacttac tcataaaggg    4600
acaggctagc tagctgtgtt agaagtagca atgacaatga ccaaggactg ctacacctct    4660
gattacaatt ctgatgtgaa aaagatggtg tttggctctt atagagcctg tgtgaaaggc    4720
ccatggatca gctcttcctg tgtttgtaat ttaatgctgc tacaagatgt ttctgtttct    4780
tagattctga ccatgactca taagcttctt gtcattcttc attgcttgtt tgtggtcaca    4840
gatgcacaac actcctccag tcttgtgggg gcagcttttg ggaagtctca gcagctcttc    4900
tggctgtgtt gtcagcactg taacttcgca gaaaagagtc ggattaccaa aacactgcct    4960
gctcttcaga cttaaagcac tgataggact taaaatagtc tcattcaaat actgtattt    5020 atataggcat ttcacaaaaa cagcaaaatt gtggcatttt gtgaggccaa ggcttggatg    5080
cgtgtgtaat agagccttgt ggtgtgtgcg cacacaccca gagggagagt ttgaaaaatg    5140
cttattggac acgtaacctg gctctaattt gggctgtttt tcagatacac tgtgataagt    5200
tcttttacaa atatctatag acatggtaaa cttttggttt tcagatatgc ttaatgatag    5260
tcttactaaa tgcagaaata agaataaact ttctcaaatt attaaaaatg cctacacagt    5320
aagtgtgaat tgctgcaaca ggtttgttct caggagggta agaactccag gtctaaacag    5380
ctgacccagt gatggggaat ttatccttga ccaatttatc cttgaccaat aacctaattg    5440
tctattcctg agttataaaa gtccccatcc ttattagctc tactggaatt ttcatacacg    5500
taaatgcaga agttactaag tattaagtat tactgagtat taagtagtaa tctgtcagtt    5560
attaaaattt gtaaaatcta tttatgaaag gtcattaaac cagatcatgt tccttttttt    5620
gtaatcaagg tgactaagaa aatcagttgt gtaaataaaa tcatgtatca taaaaaaaaa    5680
aaaaaaa                                                              5687
```

<210> SEQ ID NO 8
<211> LENGTH: 1040
<212> TYPE: PRT
<213> ORGANISM: Homo sapiens

<400> SEQUENCE: 8

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Ile Ala Ser Lys Pro Tyr Ala Phe
          35                  40                  45

Asp Arg Val Phe Gln Ser Ser Thr Ser Gln Glu Gln Val Tyr Asn Asp
 50                      55                  60

Cys Ala Lys Lys Ile Val Lys Asp Val Leu Glu Gly Tyr Asn Gly Thr
 65                  70                  75                  80

Ile Phe Ala Tyr Gly Gln Thr Ser Ser Gly Lys Thr His Thr Met Glu
                     85                  90                  95

Gly Lys Leu His Asp Pro Glu Gly Met Gly Ile Ile Pro Arg Ile Val
             100                 105                 110

Gln Asp Ile Phe Asn Tyr Ile Tyr Ser Met Asp Glu Asn Leu Glu Phe
             115                 120                 125

His Ile Lys Val Ser Tyr Phe Glu Ile Tyr Leu Asp Lys Ile Arg Asp
         130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                 165                 170                 175

Asp Glu Val Met Asp Thr Ile Asp Glu Gly Lys Ser Asn Arg His Val
             180                 185                 190

Ala Val Thr Asn Met Asn Glu His Ser Ser Arg Ser His Ser Ile Phe
         195                 200                 205

Leu Ile Asn Val Lys Gln Glu Asn Thr Gln Thr Glu Gln Lys Leu Ser
210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                 245                 250                 255

Ser Leu Ser Ala Leu Gly Asn Val Ile Ser Ala Leu Ala Glu Gly Ser
             260                 265                 270

Thr Tyr Val Pro Tyr Arg Asp Ser Lys Met Thr Arg Ile Leu Gln Asp
         275                 280                 285

Ser Leu Gly Gly Asn Cys Arg Thr Thr Ile Val Ile Cys Cys Ser Pro
290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                 325                 330                 335

Ala Glu Gln Trp Lys Lys Tyr Glu Lys Glu Lys Glu Lys Asn Lys
             340                 345                 350

Ile Leu Arg Asn Thr Ile Gln Trp Leu Glu Asn Glu Leu Asn Arg Trp
         355                 360                 365

Arg Asn Gly Glu Thr Val Pro Ile Asp Glu Gln Phe Asp Lys Glu Lys
370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                 405                 410                 415

Glu Arg Arg Lys Cys Glu Glu Glu Ile Ala Lys Leu Tyr Lys Gln Leu
             420                 425                 430

Asp Asp Lys Asp Glu Glu Ile Asn Gln Gln Ser Gln Leu Val Glu Lys
         435                 440                 445

```
Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
                565                 570                 575

Pro Glu Gly Thr Gly Met Ile Asp Glu Glu Phe Thr Val Ala Arg Leu
            580                 585                 590

Tyr Ile Ser Lys Met Lys Ser Glu Val Lys Thr Met Val Lys Arg Cys
        595                 600                 605

Lys Gln Leu Glu Ser Thr Gln Thr Glu Ser Asn Lys Lys Met Glu Glu
        610                 615                 620

Asn Glu Lys Glu Leu Ala Ala Cys Gln Leu Arg Ile Ser Gln Glu Asp
625                 630                 635                 640

Pro Lys Trp Glu Phe Pro Arg Lys Asn Leu Val Leu Gly Lys Thr Leu
                645                 650                 655

Gly Glu Gly Glu Phe Gly Lys Val Val Lys Ala Thr Ala Phe His Leu
            660                 665                 670

Lys Gly Arg Ala Gly Tyr Thr Thr Val Ala Val Lys Met Leu Lys Glu
        675                 680                 685

Asn Ala Ser Pro Ser Glu Leu Arg Asp Leu Leu Ser Glu Phe Asn Val
        690                 695                 700

Leu Lys Gln Val Asn His Pro His Val Ile Lys Leu Tyr Gly Ala Cys
705                 710                 715                 720

Ser Gln Asp Gly Pro Leu Leu Leu Ile Val Glu Tyr Ala Lys Tyr Gly
                725                 730                 735

Ser Leu Arg Gly Phe Leu Arg Glu Ser Arg Lys Val Gly Pro Gly Tyr
            740                 745                 750

Leu Gly Ser Gly Gly Ser Arg Asn Ser Ser Leu Asp His Pro Asp
        755                 760                 765

Glu Arg Ala Leu Thr Met Gly Asp Leu Ile Ser Phe Ala Trp Gln Ile
        770                 775                 780

Ser Gln Gly Met Gln Tyr Leu Ala Glu Met Lys Leu Val His Arg Asp
785                 790                 795                 800

Leu Ala Ala Arg Asn Ile Leu Val Ala Glu Gly Arg Lys Met Lys Ile
                805                 810                 815

Ser Asp Phe Gly Leu Ser Arg Asp Val Tyr Glu Glu Asp Ser Tyr Val
            820                 825                 830

Lys Arg Ser Gln Gly Arg Ile Pro Val Lys Trp Met Ala Ile Glu Ser
        835                 840                 845

Leu Phe Asp His Ile Tyr Thr Thr Gln Ser Asp Val Trp Ser Phe Gly
850                 855                 860

Val Leu Leu Trp Glu Ile Val Thr Leu Gly Gly Asn Pro Tyr Pro Gly
```

```
                865                 870                 875                 880
Ile Pro Pro Glu Arg Leu Phe Asn Leu Leu Lys Thr Gly His Arg Met
                    885                 890                 895
Glu Arg Pro Asp Asn Cys Ser Glu Glu Met Tyr Arg Leu Met Leu Gln
                900                 905                 910
Cys Trp Lys Gln Glu Pro Asp Lys Arg Pro Val Phe Ala Asp Ile Ser
            915                 920                 925
Lys Asp Leu Glu Lys Met Met Val Lys Arg Arg Asp Tyr Leu Asp Leu
    930                 935                 940
Ala Ala Ser Thr Pro Ser Asp Ser Leu Ile Tyr Asp Asp Gly Leu Ser
945                 950                 955                 960
Glu Glu Glu Thr Pro Leu Val Asp Cys Asn Asn Ala Pro Leu Pro Arg
                965                 970                 975
Ala Leu Pro Ser Thr Trp Ile Glu Asn Lys Leu Tyr Gly Met Ser Asp
            980                 985                 990
Pro Asn Trp Pro Gly Glu Ser Pro  Val Pro Leu Thr Arg Ala Asp Gly
        995                 1000                1005
Thr Asn  Thr Gly Phe Pro Arg  Tyr Pro Asn Asp Ser  Val Tyr Ala
    1010                1015                1020
Asn Trp  Met Leu Ser Pro Ser  Ala Ala Lys Leu Met  Asp Thr Phe
    1025                1030                1035
Asp Ser
    1040

<210> SEQ ID NO 9
<211> LENGTH: 6317
<212> TYPE: DNA
<213> ORGANISM: Homo sapiens
<220> FEATURE:
<221> NAME/KEY: CDS
<222> LOCATION: (471)..(4220)
<223> OTHER INFORMATION: KIF5B-RET fusion variant3

<400> SEQUENCE: 9
ctcctcccgc accgccctgt cgcccaacgg cggcctcagg agtgatcggg cagcagtcgg      60
ccggccagcg gacggcagag cgggcggacg ggtaggcccg gcctgctctt cgcgaggagg     120
aagaaggtgg ccactctccc ggtccccaga acctccccag cccccgcagt ccgcccagac     180
cgtaaagggg gacgctgagg agccgcggac gctctccccg gtgccgccgc cgctgccgcc     240
gccatggctg ccatgatgga tcggaagtga gcattagggt taacggctgc ggcgccggc      300 tcttcaagtc ccggctcccc ggccgcctcc acccggggaa gcgcagcgcg gcgcagctga     360
ctgctgcctc tcacggccct cgcgaccaca agccctcagg tccggcgcgt tccctgcaag     420
actgagcggc ggggagtggc tcccggccgc cggccccggc tgcagagaaag atg gcg     476
                                                         Met Ala
                                                         1 gac ctg gcc gag tgc aac atc aaa gtg atg tgt cgc ttc aga cct ctc      524
Asp Leu Ala Glu Cys Asn Ile Lys Val Met Cys Arg Phe Arg Pro Leu
        5                  10                  15 aac gag tct gaa gtg aac cgc ggc gac aag tac atc gcc aag ttt cag      572
Asn Glu Ser Glu Val Asn Arg Gly Asp Lys Tyr Ile Ala Lys Phe Gln
    20                  25                  30 gga gaa gac acg gtc gtg atc gcg tcc aag cct tat gca ttt gat cgg      620
Gly Glu Asp Thr Val Val Ile Ala Ser Lys Pro Tyr Ala Phe Asp Arg
35                  40                  45                  50 gtg ttc cag tca agc aca tct caa gag caa gtg tat aat gac tgt gca      668
Val Phe Gln Ser Ser Thr Ser Gln Glu Gln Val Tyr Asn Asp Cys Ala
```

```
                        55                  60                      65
aag aag att gtt aaa gat gta ctt gaa gga tat aat gga aca ata ttt        716
Lys Lys Ile Val Lys Asp Val Leu Glu Gly Tyr Asn Gly Thr Ile Phe
            70                  75                      80 gca tat gga caa aca tcc tct ggg aag aca cac aca atg gag ggt aaa        764
Ala Tyr Gly Gln Thr Ser Ser Gly Lys Thr His Thr Met Glu Gly Lys
        85                  90                      95 ctt cat gat cca gaa ggc atg gga att att cca aga ata gtg caa gat        812
Leu His Asp Pro Glu Gly Met Gly Ile Ile Pro Arg Ile Val Gln Asp
100                 105                     110 att ttt aat tat att tac tcc atg gat gaa aat ttg gaa ttt cat att        860
Ile Phe Asn Tyr Ile Tyr Ser Met Asp Glu Asn Leu Glu Phe His Ile
115                 120                     125                 130 aag gtt tca tat ttt gaa ata tat ttg gat aag ata agg gac ctg tta        908
Lys Val Ser Tyr Phe Glu Ile Tyr Leu Asp Lys Ile Arg Asp Leu Leu
                135                 140                     145 gat gtt tca aag acc aac ctt tca gtt cat gaa gac aaa aac cga gtt        956
Asp Val Ser Lys Thr Asn Leu Ser Val His Glu Asp Lys Asn Arg Val
            150                 155                     160 ccc tat gta aag ggg tgc aca gag cgt ttt gta tgt agt cca gat gaa       1004
Pro Tyr Val Lys Gly Cys Thr Glu Arg Phe Val Cys Ser Pro Asp Glu
        165                 170                     175 gtt atg gat acc ata gat gaa gga aaa tcc aac aga cat gta gca gtt       1052
Val Met Asp Thr Ile Asp Glu Gly Lys Ser Asn Arg His Val Ala Val
180                 185                     190 aca aat atg aat gaa cat agc tct agg agt cac agt ata ttt ctt att       1100
Thr Asn Met Asn Glu His Ser Ser Arg Ser His Ser Ile Phe Leu Ile
195                 200                     205                 210 aat gtc aaa caa gag aac aca caa acg gaa caa aag ctg agt gga aaa       1148
Asn Val Lys Gln Glu Asn Thr Gln Thr Glu Gln Lys Leu Ser Gly Lys
                215                 220                     225 ctt tat ctg gtt gat tta gct ggt agt gaa aag gtt agt aaa act gga       1196
Leu Tyr Leu Val Asp Leu Ala Gly Ser Glu Lys Val Ser Lys Thr Gly
            230                 235                     240 gct gaa ggt gct gtg ctg gat gaa gct aaa aac atc aac aag tca ctt       1244
Ala Glu Gly Ala Val Leu Asp Glu Ala Lys Asn Ile Asn Lys Ser Leu
        245                 250                     255 tct gct ctt gga aat gtt att tct gct ttg gct gag ggt agt aca tat       1292
Ser Ala Leu Gly Asn Val Ile Ser Ala Leu Ala Glu Gly Ser Thr Tyr
260                 265                     270 gtt cca tat cga gat agt aaa atg aca aga atc ctt caa gat tca tta       1340
Val Pro Tyr Arg Asp Ser Lys Met Thr Arg Ile Leu Gln Asp Ser Leu
275                 280                     285                 290 ggt ggc aac tgt aga acc act att gta att tgc tgc tct cca tca tca       1388
Gly Gly Asn Cys Arg Thr Thr Ile Val Ile Cys Cys Ser Pro Ser Ser
                295                 300                     305 tac aat gag tct gaa aca aaa tct aca ctc tta ttt ggc caa agg gcc       1436
Tyr Asn Glu Ser Glu Thr Lys Ser Thr Leu Leu Phe Gly Gln Arg Ala
            310                 315                     320 aaa aca att aag aac aca gtt tgt gtc aat gtg gag tta act gca gaa       1484
Lys Thr Ile Lys Asn Thr Val Cys Val Asn Val Glu Leu Thr Ala Glu
        325                 330                     335 cag tgg aaa aag aag tat gaa aaa gaa aaa gaa aaa aat aag atc ctg       1532
Gln Trp Lys Lys Lys Tyr Glu Lys Glu Lys Glu Lys Asn Lys Ile Leu
340                 345                     350 cgg aac act att cag tgg ctt gaa aat gag ctc aac aga tgg cgt aat       1580
Arg Asn Thr Ile Gln Trp Leu Glu Asn Glu Leu Asn Arg Trp Arg Asn
355                 360                     365                 370 ggg gag acg gtg cct att gat gaa cag ttt gac aaa gag aaa gcc aac       1628
```

-continued

```
Gly Glu Thr Val Pro Ile Asp Glu Gln Phe Asp Lys Glu Lys Ala Asn
            375                 380                 385 ttg gaa gct ttc aca gtg gat aaa gat att act ctt acc aat gat aaa      1676
Leu Glu Ala Phe Thr Val Asp Lys Asp Ile Thr Leu Thr Asn Asp Lys
            390                 395                 400 cca gca acc gca att gga gtt ata gga aat ttt act gat gct gaa aga      1724
Pro Ala Thr Ala Ile Gly Val Ile Gly Asn Phe Thr Asp Ala Glu Arg
            405                 410                 415 aga aag tgt gaa gaa gaa att gct aaa tta tac aaa cag ctt gat gac      1772
Arg Lys Cys Glu Glu Glu Ile Ala Lys Leu Tyr Lys Gln Leu Asp Asp
        420                 425                 430 aag gat gaa gaa att aac cag caa agt caa ctg gta gag aaa ctg aag      1820
Lys Asp Glu Glu Ile Asn Gln Gln Ser Gln Leu Val Glu Lys Leu Lys
435                 440                 445                 450 acg caa atg ttg gat cag gag gag ctt ttg gca tct acc aga agg gat      1868
Thr Gln Met Leu Asp Gln Glu Glu Leu Leu Ala Ser Thr Arg Arg Asp
                455                 460                 465 caa gac aat atg caa gct gag ctg aat cgc ctt caa gca gaa aat gat      1916
Gln Asp Asn Met Gln Ala Glu Leu Asn Arg Leu Gln Ala Glu Asn Asp
            470                 475                 480 gcc tct aaa gaa gaa gtg aaa gaa gtt tta cag gcc cta gaa gaa ctt      1964
Ala Ser Lys Glu Glu Val Lys Glu Val Leu Gln Ala Leu Glu Glu Leu
        485                 490                 495 gct gtc aat tat gat cag aag tct cag gaa gtt gaa gac aaa act aag      2012
Ala Val Asn Tyr Asp Gln Lys Ser Gln Glu Val Glu Asp Lys Thr Lys
    500                 505                 510 gaa tat gaa ttg ctt agt gat gaa ttg aat cag aaa tcg gca act tta      2060
Glu Tyr Glu Leu Leu Ser Asp Glu Leu Asn Gln Lys Ser Ala Thr Leu
515                 520                 525                 530 gcg agt ata gat gct gag ctt cag aaa ctt aag gaa atg acc aac cac      2108
Ala Ser Ile Asp Ala Glu Leu Gln Lys Leu Lys Glu Met Thr Asn His
                535                 540                 545 cag aaa aaa cga gca gct gag atg atg gca tct tta cta aaa gac ctt      2156
Gln Lys Lys Arg Ala Ala Glu Met Met Ala Ser Leu Leu Lys Asp Leu
            550                 555                 560 gca gaa ata gga att gct gtg gga aat aat gat gta aag cag cct gag      2204
Ala Glu Ile Gly Ile Ala Val Gly Asn Asn Asp Val Lys Gln Pro Glu
        565                 570                 575 gga act ggc atg ata gat gaa gag ttc act gtt gca aga ctc tac att      2252
Gly Thr Gly Met Ile Asp Glu Glu Phe Thr Val Ala Arg Leu Tyr Ile
    580                 585                 590 agc aaa atg aag tca gaa gta aaa acc atg gtg aaa cgt tgc aag cag      2300
Ser Lys Met Lys Ser Glu Val Lys Thr Met Val Lys Arg Cys Lys Gln
595                 600                 605                 610 tta gaa agc aca caa act gag agc aac aaa aaa atg gaa gaa aat gaa      2348
Leu Glu Ser Thr Gln Thr Glu Ser Asn Lys Lys Met Glu Glu Asn Glu
                615                 620                 625 aag gag tta gca gca tgt cag ctt cgt atc tct caa cat gaa gcc aaa      2396
Lys Glu Leu Ala Ala Cys Gln Leu Arg Ile Ser Gln His Glu Ala Lys
            630                 635                 640 atc aag tca ttg act gaa tac ctt caa aat gtg gaa caa aag aaa aga      2444
Ile Lys Ser Leu Thr Glu Tyr Leu Gln Asn Val Glu Gln Lys Lys Arg
        645                 650                 655 cag ttg gag gaa tct gtc gat gcc ctc agt gaa gaa cta gtc cag ctt      2492
Gln Leu Glu Glu Ser Val Asp Ala Leu Ser Glu Glu Leu Val Gln Leu
    660                 665                 670 cga gca caa gag aaa gtc cat gaa atg gaa aag gag cac tta aat aag      2540
Arg Ala Gln Glu Lys Val His Glu Met Glu Lys Glu His Leu Asn Lys
675                 680                 685                 690
```

| | |
|---|---|
| gtt cag act gca aat gaa gtt aag caa gct gtt gaa cag cag atc cag<br>Val Gln Thr Ala Asn Glu Val Lys Gln Ala Val Glu Gln Gln Ile Gln<br>                      695                      700                  705 | 2588 |
| agc cat aga gaa act cat caa aaa cag atc agt agt ttg aga gat gaa<br>Ser His Arg Glu Thr His Gln Lys Gln Ile Ser Ser Leu Arg Asp Glu<br>            710                    715                    720 | 2636 |
| gta gaa gca aaa gca aaa ctt att act gat ctt caa gac caa aac cag<br>Val Glu Ala Lys Ala Lys Leu Ile Thr Asp Leu Gln Asp Gln Asn Gln<br>        725                    730                    735 | 2684 |
| aaa atg atg tta gag cag gaa cgt cta aga gta gaa cat gag aag ttg<br>Lys Met Met Leu Glu Gln Glu Arg Leu Arg Val Glu His Glu Lys Leu<br>            740                    745                    750 | 2732 |
| aaa gcc aca gat cag gaa aag agc aga aaa cta cat gaa ctt acg gtt<br>Lys Ala Thr Asp Gln Glu Lys Ser Arg Lys Leu His Glu Leu Thr Val<br>755                    760                    765                    770 | 2780 |
| atg caa gat aga cga gaa caa gca aga caa gac ttg aag ggt ttg gaa<br>Met Gln Asp Arg Arg Glu Gln Ala Arg Gln Asp Leu Lys Gly Leu Glu<br>                    775                    780                    785 | 2828 |
| gag aca gtg gca aaa gaa ctt cag act tta cac aac ctg cgc aaa ctc<br>Glu Thr Val Ala Lys Glu Leu Gln Thr Leu His Asn Leu Arg Lys Leu<br>            790                    795                    800 | 2876 |
| ttt gtt cag gac ctg gct aca aga gtt aaa aag agt gct gag att gat<br>Phe Val Gln Asp Leu Ala Thr Arg Val Lys Lys Ser Ala Glu Ile Asp<br>        805                    810                    815 | 2924 |
| tct gat gac acc gga ggc agc gct gct cag aag caa aaa atc tcc ttt<br>Ser Asp Asp Thr Gly Gly Ser Ala Ala Gln Lys Gln Lys Ile Ser Phe<br>            820                    825                    830 | 2972 |
| ctt gaa aat aat ctt gaa cag ctc act aaa gtg cac aaa cag gag gat<br>Leu Glu Asn Asn Leu Glu Gln Leu Thr Lys Val His Lys Gln Glu Asp<br>835                    840                    845                    850 | 3020 |
| cca aag tgg gaa ttc cct cgg aag aac ttg gtt ctt gga aaa act cta<br>Pro Lys Trp Glu Phe Pro Arg Lys Asn Leu Val Leu Gly Lys Thr Leu<br>                    855                    860                    865 | 3068 |
| gga gaa ggc gaa ttt gga aaa gtg gtc aag gca acg gcc ttc cat ctg<br>Gly Glu Gly Glu Phe Gly Lys Val Val Lys Ala Thr Ala Phe His Leu<br>              870                    875                    880 | 3116 |
| aaa ggc aga gca ggg tac acc acg gtg gcc gtg aag atg ctg aaa gag<br>Lys Gly Arg Ala Gly Tyr Thr Thr Val Ala Val Lys Met Leu Lys Glu<br>        885                    890                    895 | 3164 |
| aac gcc tcc ccg agt gag ctt cga gac ctg ctg tca gag ttc aac gtc<br>Asn Ala Ser Pro Ser Glu Leu Arg Asp Leu Leu Ser Glu Phe Asn Val<br>            900                    905                    910 | 3212 |
| ctg aag cag gtc aac cac cca cat gtc atc aaa ttg tat ggg gcc tgc<br>Leu Lys Gln Val Asn His Pro His Val Ile Lys Leu Tyr Gly Ala Cys<br>915                    920                    925                    930 | 3260 |
| agc cag gat ggc ccg ctc ctc ctc atc gtg gag tac gcc aaa tac ggc<br>Ser Gln Asp Gly Pro Leu Leu Leu Ile Val Glu Tyr Ala Lys Tyr Gly<br>              935                    940                    945 | 3308 |
| tcc ctg cgg ggc ttc ctc cgc gag agc cgc aaa gtg ggg cct ggc tac<br>Ser Leu Arg Gly Phe Leu Arg Glu Ser Arg Lys Val Gly Pro Gly Tyr<br>            950                    955                    960 | 3356 |
| ctg ggc agt gga ggc agc cgc aac tcc agc tcc ctg gac cac ccg gat<br>Leu Gly Ser Gly Gly Ser Arg Asn Ser Ser Ser Leu Asp His Pro Asp<br>        965                    970                    975 | 3404 |
| gag cgg gcc ctc acc atg ggc gac ctc atc tca ttt gcc tgg cag atc<br>Glu Arg Ala Leu Thr Met Gly Asp Leu Ile Ser Phe Ala Trp Gln Ile<br>            980                    985                    990 | 3452 |
| tca cag ggg atg cag tat ctg gcc gag atg aag ctc gtt cat cgg<br>Ser Gln Gly Met Gln Tyr Leu Ala Glu Met Lys Leu Val His Arg<br>995                    1000                    1005 | 3497 |

-continued

| | | | | | | | | | | | | |
|---|---|---|---|---|---|---|---|---|---|---|---|---|
| gac | ttg | gca | gcc | aga | aac | atc | ctg | gta | gct | gag | ggg | cgg | aag | atg | 3542 |
| Asp | Leu | Ala | Ala | Arg | Asn | Ile | Leu | Val | Ala | Glu | Gly | Arg | Lys | Met | |
| 1010 | | | | 1015 | | | | | 1020 | | | | | | |

```
gac ttg gca gcc aga aac atc ctg gta gct gag ggg cgg aag atg      3542
Asp Leu Ala Ala Arg Asn Ile Leu Val Ala Glu Gly Arg Lys Met
1010                1015                1020 aag att tcg gat ttc ggc ttg tcc cga gat gtt tat gaa gag gat      3587
Lys Ile Ser Asp Phe Gly Leu Ser Arg Asp Val Tyr Glu Glu Asp
1025                1030                1035 tcc tac gtg aag agg agc cag ggt cgg att cca gtt aaa tgg atg      3632
Ser Tyr Val Lys Arg Ser Gln Gly Arg Ile Pro Val Lys Trp Met
1040                1045                1050 gca att gaa tcc ctt ttt gat cat atc tac acc acg caa agt gat      3677
Ala Ile Glu Ser Leu Phe Asp His Ile Tyr Thr Thr Gln Ser Asp
1055                1060                1065 gta tgg tct ttt ggt gtc ctg ctg tgg gag atc gtg acc cta ggg      3722
Val Trp Ser Phe Gly Val Leu Leu Trp Glu Ile Val Thr Leu Gly
1070                1075                1080 gga aac ccc tat cct ggg att cct cct gag cgg ctc ttc aac ctt      3767
Gly Asn Pro Tyr Pro Gly Ile Pro Pro Glu Arg Leu Phe Asn Leu
1085                1090                1095 ctg aag acc ggc cac cgg atg gag agg cca gac aac tgc agc gag      3812
Leu Lys Thr Gly His Arg Met Glu Arg Pro Asp Asn Cys Ser Glu
1100                1105                1110 gag atg tac cgc ctg atg ctg caa tgc tgg aag cag gag ccg gac      3857
Glu Met Tyr Arg Leu Met Leu Gln Cys Trp Lys Gln Glu Pro Asp
1115                1120                1125 aaa agg ccg gtg ttt gcg gac atc agc aaa gac ctg gag aag atg      3902
Lys Arg Pro Val Phe Ala Asp Ile Ser Lys Asp Leu Glu Lys Met
1130                1135                1140 atg gtt aag agg aga gac tac ttg gac ctt gcg gcg tcc act cca      3947
Met Val Lys Arg Arg Asp Tyr Leu Asp Leu Ala Ala Ser Thr Pro
1145                1150                1155 tct gac tcc ctg att tat gac gac ggc ctc tca gag gag gag aca      3992
Ser Asp Ser Leu Ile Tyr Asp Asp Gly Leu Ser Glu Glu Glu Thr
1160                1165                1170 ccg ctg gtg gac tgt aat aat gcc ccc ctc cct cga gcc ctc cct      4037
Pro Leu Val Asp Cys Asn Asn Ala Pro Leu Pro Arg Ala Leu Pro
1175                1180                1185 tcc aca tgg att gaa aac aaa ctc tat ggc atg tca gac ccg aac      4082
Ser Thr Trp Ile Glu Asn Lys Leu Tyr Gly Met Ser Asp Pro Asn
1190                1195                1200 tgg cct gga gag agt cct gta cca ctc acg aga gct gat ggc act      4127
Trp Pro Gly Glu Ser Pro Val Pro Leu Thr Arg Ala Asp Gly Thr
1205                1210                1215 aac act ggg ttt cca aga tat cca aat gat agt gta tat gct aac      4172
Asn Thr Gly Phe Pro Arg Tyr Pro Asn Asp Ser Val Tyr Ala Asn
1220                1225                1230 tgg atg ctt tca ccc tca gcg gca aaa tta atg gac acg ttt gat      4217
Trp Met Leu Ser Pro Ser Ala Ala Lys Leu Met Asp Thr Phe Asp
1235                1240                1245 agt    taacatttct ttgtgaaagg taatggactc acaaggggaa gaaacatgct   4270
Ser
1250 gagaatggaa agtctaccgg cccttctttt gtgaacgtca cattggccga gccgtgttca   4330 gttcccaggt ggcagactcg tttttggtag tttgttttaa cttccaaggt ggttttactt   4390 ctgatagccg gtgattttcc ctcctagcag acatgccaca ccgggtaaga gctctgagtc   4450 ttagtggtta agcattcctt tctcttcagt gcccagcagc acccagtgtt ggtctgtgtc   4510 catcagtgac caccaacatt ctgtgttcac atgtgtgggt ccaacactta ctacctggtg   4570
```

| | |
|---|---|
| tatgaaattg gacctgaact gttggatttt tctagttgcc gccaaacaag gcaaaaaaat | 4630 |
| ttaaacatga agcacacaca caaaaaaggc agtaggaaaa atgctggccc tgatgacctg | 4690 |
| tccttattca gaatgagaga ctgcgggggg ggcctggggg tagtgtcaat gcccctccag | 4750 |
| ggctggaggg gaagagggc cccgaggatg ggcctgggct cagcattcga gatcttgaga | 4810 |
| atgattttttt tttaatcatg caacctttcc ttaggaagac atttggtttt catcatgatt | 4870 |
| aagatgattc ctagatttag cacaatggag agattccatg ccatctttac tatgtggatg | 4930 |
| gtggtatcag ggaagagggc tcacaagaca catttgtccc ccgggcccac cacatcatcc | 4990 |
| tcacgtgttc ggtactgagc agccactacc cctgatgaga acagtatgaa gaaagggggc | 5050 |
| tgttggagtc ccagaattgc tgacagcaga ggctttgctg ctgtgaatcc cacctgccac | 5110 |
| cagcctgcag cacaccccac agccaagtag aggcgaaagc agtggctcat cctacctgtt | 5170 |
| aggagcaggt agggcttgta ctcactttaa tttgaatctt atcaacttac tcataaaggg | 5230 |
| acaggctagc tagctgtgtt agaagtagca atgacaatga ccaaggactg ctacacctct | 5290 |
| gattacaatt ctgatgtgaa aaagatggtg tttggctctt atagagcctg tgtgaaaggc | 5350 |
| ccatggatca gctcttcctg tgtttgtaat ttaatgctgc tacaagatgt ttctgtttct | 5410 |
| tagattctga ccatgactca taagcttctt gtcattcttc attgcttgtt tgtggtcaca | 5470 |
| gatgcacaac actcctccag tcttgtgggg gcagcttttg ggaagtctca gcagctcttc | 5530 |
| tggctgtgtt gtcagcactg taacttcgca gaaaagagtc ggattaccaa aacactgcct | 5590 |
| gctcttcaga cttaaagcac tgataggact aaaatagtc tcattcaaat actgtatttt | 5650 |
| ataggcat ttcacaaaaa cagcaaaatt gtggcatttt tgtgaggccaa ggcttggatg | 5710 |
| cgtgtgtaat agagccttgt ggtgtgtgcg cacacaccca gagggagagt ttgaaaaatg | 5770 |
| cttattggac acgtaacctg gctctaattt gggctgtttt tcagatacac tgtgataagt | 5830 |
| tctttacaa atatctatag acatggtaaa cttttggttt tcagatatgc ttaatgatag | 5890 |
| tcttactaaa tgcagaaata agaataaact ttctcaaatt attaaaaatg cctacacagt | 5950 |
| aagtgtgaat tgctgcaaca ggtttgttct caggagggta agaactccag gtctaaacag | 6010 |
| ctgacccagt gatggggaat ttatccttga ccaatttatc cttgaccaat aacctaattg | 6070 |
| tctattcctg agttataaaa gtccccatcc ttattagctc tactggaatt ttcatacacg | 6130 |
| taaatgcaga agttactaag tattaagtat tactgagtat taagtagtaa tctgtcagtt | 6190 |
| attaaatttt gtaaaatcta tttatgaaag gtcattaaac cagatcatgt tccttttttt | 6250 |
| gtaatcaagg tgactaagaa aatcagttgt gtaaataaaa tcatgtatca taaaaaaaaa | 6310 |
| aaaaaaa | 6317 |

<210> SEQ ID NO 10
<211> LENGTH: 1250
<212> TYPE: PRT
<213> ORGANISM: Homo sapiens

<400> SEQUENCE: 10

Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

```
Cys Ala Lys Lys Ile Val Lys Asp Val Leu Glu Gly Tyr Asn Gly Thr
 65                  70                  75                  80

Ile Phe Ala Tyr Gly Gln Thr Ser Ser Gly Lys Thr His Thr Met Glu
                 85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
            115                 120                 125

His Ile Lys Val Ser Tyr Phe Glu Ile Tyr Leu Asp Lys Ile Arg Asp
            130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
            195                 200                 205

Leu Ile Asn Val Lys Gln Glu Asn Thr Gln Thr Glu Gln Lys Leu Ser
210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
            275                 280                 285

Ser Leu Gly Gly Asn Cys Arg Thr Thr Ile Val Ile Cys Cys Ser Pro
290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
            355                 360                 365

Arg Asn Gly Glu Thr Val Pro Ile Asp Glu Gln Phe Asp Lys Glu Lys
            370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Glu Ile Ala Lys Leu Tyr Lys Gln Leu
            420                 425                 430

Asp Asp Lys Asp Glu Glu Ile Asn Gln Gln Ser Gln Leu Val Glu Lys
            435                 440                 445

Leu Lys Thr Gln Met Leu Asp Gln Glu Glu Leu Leu Ala Ser Thr Arg
450                 455                 460

Arg Asp Gln Asp Asn Met Gln Ala Glu Leu Asn Arg Leu Gln Ala Glu
465                 470                 475                 480
```

```
Asn Asp Ala Ser Lys Glu Glu Val Lys Glu Val Leu Gln Ala Leu Glu
            485                 490                 495
Glu Leu Ala Val Asn Tyr Asp Gln Lys Ser Gln Glu Val Glu Asp Lys
        500                 505                 510
Thr Lys Glu Tyr Glu Leu Leu Ser Asp Glu Leu Asn Gln Lys Ser Ala
    515                 520                 525
Thr Leu Ala Ser Ile Asp Ala Glu Leu Gln Lys Leu Lys Glu Met Thr
530                 535                 540
Asn His Gln Lys Lys Arg Ala Ala Glu Met Met Ala Ser Leu Leu Lys
545                 550                 555                 560
Asp Leu Ala Glu Ile Gly Ile Ala Val Gly Asn Asn Asp Val Lys Gln
                565                 570                 575
Pro Glu Gly Thr Gly Met Ile Asp Glu Glu Phe Thr Val Ala Arg Leu
            580                 585                 590
Tyr Ile Ser Lys Met Lys Ser Glu Val Lys Thr Met Val Lys Arg Cys
        595                 600                 605
Lys Gln Leu Glu Ser Thr Gln Thr Glu Ser Asn Lys Lys Met Glu Glu
    610                 615                 620
Asn Glu Lys Glu Leu Ala Ala Cys Gln Leu Arg Ile Ser Gln His Glu
625                 630                 635                 640
Ala Lys Ile Lys Ser Leu Thr Glu Tyr Leu Gln Asn Val Glu Gln Lys
                645                 650                 655
Lys Arg Gln Leu Glu Glu Ser Val Asp Ala Leu Ser Glu Glu Leu Val
            660                 665                 670
Gln Leu Arg Ala Gln Glu Lys Val His Glu Met Glu Lys Glu His Leu
        675                 680                 685
Asn Lys Val Gln Thr Ala Asn Glu Val Lys Gln Ala Val Glu Gln Gln
    690                 695                 700
Ile Gln Ser His Arg Glu Thr His Gln Lys Gln Ile Ser Ser Leu Arg
705                 710                 715                 720
Asp Glu Val Glu Ala Lys Ala Lys Leu Ile Thr Asp Leu Gln Asp Gln
                725                 730                 735
Asn Gln Lys Met Met Leu Glu Gln Glu Arg Leu Arg Val Glu His Glu
            740                 745                 750
Lys Leu Lys Ala Thr Asp Gln Glu Lys Ser Arg Lys Leu His Glu Leu
        755                 760                 765
Thr Val Met Gln Asp Arg Arg Glu Gln Ala Arg Gln Asp Leu Lys Gly
    770                 775                 780
Leu Glu Glu Thr Val Ala Lys Glu Leu Gln Thr Leu His Asn Leu Arg
785                 790                 795                 800
Lys Leu Phe Val Gln Asp Leu Ala Thr Arg Val Lys Lys Ser Ala Glu
                805                 810                 815
Ile Asp Ser Asp Asp Thr Gly Gly Ser Ala Ala Gln Lys Gln Lys Ile
            820                 825                 830
Ser Phe Leu Glu Asn Asn Leu Glu Gln Leu Thr Lys Val His Lys Gln
        835                 840                 845
Glu Asp Pro Lys Trp Glu Phe Pro Arg Lys Asn Leu Val Leu Gly Lys
    850                 855                 860
Thr Leu Gly Glu Gly Glu Phe Gly Lys Val Val Lys Ala Thr Ala Phe
865                 870                 875                 880
His Leu Lys Gly Arg Ala Gly Tyr Thr Thr Val Ala Val Lys Met Leu
                885                 890                 895
Lys Glu Asn Ala Ser Pro Ser Glu Leu Arg Asp Leu Leu Ser Glu Phe
```

900                 905                 910
Asn Val Leu Lys Gln Val Asn His Pro His Val Ile Lys Leu Tyr Gly
                915                 920                 925

Ala Cys Ser Gln Asp Gly Pro Leu Leu Leu Ile Val Glu Tyr Ala Lys
        930                 935                 940

Tyr Gly Ser Leu Arg Gly Phe Leu Arg Glu Ser Arg Lys Val Gly Pro
945                 950                 955                 960

Gly Tyr Leu Gly Ser Gly Gly Ser Arg Asn Ser Ser Leu Asp His
                965                 970                 975

Pro Asp Glu Arg Ala Leu Thr Met Gly Asp Leu Ile Ser Phe Ala Trp
            980                 985                 990

Gln Ile Ser Gln Gly Met Gln Tyr Leu Ala Glu Met Lys Leu Val His
                995                 1000                1005

Arg Asp Leu Ala Ala Arg Asn Ile Leu Val Ala Glu Gly Arg Lys
        1010                1015                1020

Met Lys Ile Ser Asp Phe Gly Leu Ser Arg Asp Val Tyr Glu Glu
        1025                1030                1035

Asp Ser Tyr Val Lys Arg Ser Gln Gly Arg Ile Pro Val Lys Trp
        1040                1045                1050

Met Ala Ile Glu Ser Leu Phe Asp His Ile Tyr Thr Thr Gln Ser
        1055                1060                1065

Asp Val Trp Ser Phe Gly Val Leu Leu Trp Glu Ile Val Thr Leu
        1070                1075                1080

Gly Gly Asn Pro Tyr Pro Gly Ile Pro Pro Glu Arg Leu Phe Asn
        1085                1090                1095

Leu Leu Lys Thr Gly His Arg Met Glu Arg Pro Asp Asn Cys Ser
        1100                1105                1110

Glu Glu Met Tyr Arg Leu Met Leu Gln Cys Trp Lys Gln Glu Pro
        1115                1120                1125

Asp Lys Arg Pro Val Phe Ala Asp Ile Ser Lys Asp Leu Glu Lys
        1130                1135                1140

Met Met Val Lys Arg Arg Asp Tyr Leu Asp Leu Ala Ala Ser Thr
        1145                1150                1155

Pro Ser Asp Ser Leu Ile Tyr Asp Asp Gly Leu Ser Glu Glu Glu
        1160                1165                1170

Thr Pro Leu Val Asp Cys Asn Asn Ala Pro Leu Pro Arg Ala Leu
        1175                1180                1185

Pro Ser Thr Trp Ile Glu Asn Lys Leu Tyr Gly Met Ser Asp Pro
        1190                1195                1200

Asn Trp Pro Gly Glu Ser Pro Val Pro Leu Thr Arg Ala Asp Gly
        1205                1210                1215

Thr Asn Thr Gly Phe Pro Arg Tyr Pro Asn Asp Ser Val Tyr Ala
        1220                1225                1230

Asn Trp Met Leu Ser Pro Ser Ala Ala Lys Leu Met Asp Thr Phe
        1235                1240                1245

Asp Ser
1250

<210> SEQ ID NO 11
<211> LENGTH: 7148
<212> TYPE: DNA
<213> ORGANISM: Homo sapiens
<220> FEATURE:
<221> NAME/KEY: CDS
<222> LOCATION: (471)..(5051)

<223> OTHER INFORMATION: KIF5B-RET fusion variant4

<400> SEQUENCE: 11

```
ctcctcccgc accgccctgt cgcccaacgg cggcctcagg agtgatcggg cagcagtcgg    60
ccggccagcg gacggcagag cgggcggacg ggtaggcccg gcctgctctt cgcgaggagg   120
aagaaggtgg ccactctccc ggtccccaga acctccccag ccccgcagt ccgcccagac    180 cgtaaagggg gacgctgagg agccgcggac gctctccccg gtgccgccgc cgctgccgcc   240
gccatggctg ccatgatgga tcggaagtga gcattagggt taacggctgc cggcgccggc   300
tcttcaagtc ccggctcccc ggccgcctcc acccggggaa gcgcagcgcg gcgcagctga   360
ctgctgcctc tcacggccct cgcgaccaca agccctcagg tccggcgcgt tccctgcaag   420
actgagcggc ggggagtggc tcccggccgc cggccccggc tgcgagaaag atg gcg     476
                                                         Met Ala
                                                         1
```

| | | | | | | | | | | | | | | | |
|---|---|---|---|---|---|---|---|---|---|---|---|---|---|---|---|
| gac | ctg | gcc | gag | tgc | aac | atc | aaa | gtg | atg | tgt | cgc | ttc | aga | cct | ctc | 524 |
| Asp | Leu | Ala | Glu | Cys | Asn | Ile | Lys | Val | Met | Cys | Arg | Phe | Arg | Pro | Leu | |
| | | 5 | | | | | 10 | | | | | 15 | | | | |

```
aac gag tct gaa gtg aac cgc ggc gac aag tac atc gcc aag ttt cag   572
Asn Glu Ser Glu Val Asn Arg Gly Asp Lys Tyr Ile Ala Lys Phe Gln
        20                  25                  30 gga gaa gac acg gtc gtg atc gcg tcc aag cct tat gca ttt gat cgg   620
Gly Glu Asp Thr Val Val Ile Ala Ser Lys Pro Tyr Ala Phe Asp Arg
35                  40                  45                  50 gtg ttc cag tca agc aca tct caa gag caa gtg tat aat gac tgt gca   668
Val Phe Gln Ser Ser Thr Ser Gln Glu Gln Val Tyr Asn Asp Cys Ala
                55                  60                  65 aag aag att gtt aaa gat gta ctt gaa gga tat aat gga aca ata ttt   716
Lys Lys Ile Val Lys Asp Val Leu Glu Gly Tyr Asn Gly Thr Ile Phe
            70                  75                  80 gca tat gga caa aca tcc tct ggg aag aca cac aca atg gag ggt aaa   764
Ala Tyr Gly Gln Thr Ser Ser Gly Lys Thr His Thr Met Glu Gly Lys
        85                  90                  95 ctt cat gat cca gaa ggc atg gga att att cca aga ata gtg caa gat   812
Leu His Asp Pro Glu Gly Met Gly Ile Ile Pro Arg Ile Val Gln Asp
    100                 105                 110 att ttt aat tat att tac tcc atg gat gaa aat ttg gaa ttt cat att   860
Ile Phe Asn Tyr Ile Tyr Ser Met Asp Glu Asn Leu Glu Phe His Ile
115                 120                 125                 130 aag gtt tca tat ttt gaa ata tat ttg gat aag ata agg gac ctg tta   908
Lys Val Ser Tyr Phe Glu Ile Tyr Leu Asp Lys Ile Arg Asp Leu Leu
                135                 140                 145 gat gtt tca aag acc aac ctt tca gtt cat gaa gac aaa aac cga gtt   956
Asp Val Ser Lys Thr Asn Leu Ser Val His Glu Asp Lys Asn Arg Val
            150                 155                 160 ccc tat gta aag ggg tgc aca gag cgt ttt gta tgt agt cca gat gaa  1004
Pro Tyr Val Lys Gly Cys Thr Glu Arg Phe Val Cys Ser Pro Asp Glu
        165                 170                 175 gtt atg gat acc ata gat gaa gga aaa tcc aac aga cat gta gca gtt  1052
Val Met Asp Thr Ile Asp Glu Gly Lys Ser Asn Arg His Val Ala Val
    180                 185                 190 aca aat atg aat gaa cat agc tct agg agt cac agt ata ttt ctt att  1100
Thr Asn Met Asn Glu His Ser Ser Arg Ser His Ser Ile Phe Leu Ile
195                 200                 205                 210 aat gtc aaa caa gag aac aca caa acg gaa caa aag ctg agt gga aaa  1148
Asn Val Lys Gln Glu Asn Thr Gln Thr Glu Gln Lys Leu Ser Gly Lys
                215                 220                 225 ctt tat ctg gtt gat tta gct ggt agt gaa aag gtt agt aaa act gga  1196
```

```
                Leu Tyr Leu Val Asp Leu Ala Gly Ser Glu Lys Val Ser Lys Thr Gly
                            230                 235                 240 gct gaa ggt gct gtg ctg gat gaa gct aaa aac atc aac aag tca ctt        1244
Ala Glu Gly Ala Val Leu Asp Glu Ala Lys Asn Ile Asn Lys Ser Leu
            245                 250                 255 tct gct ctt gga aat gtt att tct gct ttg gct gag ggt agt aca tat        1292
Ser Ala Leu Gly Asn Val Ile Ser Ala Leu Ala Glu Gly Ser Thr Tyr
        260                 265                 270 gtt cca tat cga gat agt aaa atg aca aga atc ctt caa gat tca tta        1340
Val Pro Tyr Arg Asp Ser Lys Met Thr Arg Ile Leu Gln Asp Ser Leu
275                 280                 285                 290 ggt ggc aac tgt aga acc act att gta att tgc tgc tct cca tca tca        1388
Gly Gly Asn Cys Arg Thr Thr Ile Val Ile Cys Cys Ser Pro Ser Ser
                295                 300                 305 tac aat gag tct gaa aca aaa tct aca ctc tta ttt ggc caa agg gcc        1436
Tyr Asn Glu Ser Glu Thr Lys Ser Thr Leu Leu Phe Gly Gln Arg Ala
            310                 315                 320 aaa aca att aag aac aca gtt tgt gtc aat gtg gag tta act gca gaa        1484
Lys Thr Ile Lys Asn Thr Val Cys Val Asn Val Glu Leu Thr Ala Glu
        325                 330                 335 cag tgg aaa aag aag tat gaa aaa gaa aaa gaa aaa aat aag atc ctg        1532
Gln Trp Lys Lys Lys Tyr Glu Lys Glu Lys Glu Lys Asn Lys Ile Leu
    340                 345                 350 cgg aac act att cag tgg ctt gaa aat gag ctc aac aga tgg cgt aat        1580
Arg Asn Thr Ile Gln Trp Leu Glu Asn Glu Leu Asn Arg Trp Arg Asn
355                 360                 365                 370 ggg gag acg gtg cct att gat gaa cag ttt gac aaa gag aaa gcc aac        1628
Gly Glu Thr Val Pro Ile Asp Glu Gln Phe Asp Lys Glu Lys Ala Asn
                375                 380                 385 ttg gaa gct ttc aca gtg gat aaa gat att act ctt acc aat gat aaa        1676
Leu Glu Ala Phe Thr Val Asp Lys Asp Ile Thr Leu Thr Asn Asp Lys
            390                 395                 400 cca gca acc gca att gga gtt ata gga aat ttt act gat gct gaa aga        1724
Pro Ala Thr Ala Ile Gly Val Ile Gly Asn Phe Thr Asp Ala Glu Arg
        405                 410                 415 aga aag tgt gaa gaa gaa att gct aaa tta tac aaa cag ctt gat gac        1772
Arg Lys Cys Glu Glu Glu Ile Ala Lys Leu Tyr Lys Gln Leu Asp Asp
    420                 425                 430 aag gat gaa gaa att aac cag caa agt caa ctg gta gag aaa ctg aag        1820
Lys Asp Glu Glu Ile Asn Gln Gln Ser Gln Leu Val Glu Lys Leu Lys
435                 440                 445                 450 acg caa atg ttg gat cag gag gag ctt ttg gca tct acc aga agg gat        1868
Thr Gln Met Leu Asp Gln Glu Glu Leu Leu Ala Ser Thr Arg Arg Asp
                455                 460                 465 caa gac aat atg caa gct gag ctg aat cgc ctt caa gca gaa aat gat        1916
Gln Asp Asn Met Gln Ala Glu Leu Asn Arg Leu Gln Ala Glu Asn Asp
            470                 475                 480 gcc tct aaa gaa gaa gtg aaa gaa gtt tta cag gcc cta gaa gaa ctt        1964
Ala Ser Lys Glu Glu Val Lys Glu Val Leu Gln Ala Leu Glu Glu Leu
        485                 490                 495 gct gtc aat tat gat cag aag tct cag gaa gtt gaa gac aaa act aag        2012
Ala Val Asn Tyr Asp Gln Lys Ser Gln Glu Val Glu Asp Lys Thr Lys
    500                 505                 510 gaa tat gaa ttg ctt agt gat gaa ttg aat cag aaa tcg gca act tta        2060
Glu Tyr Glu Leu Leu Ser Asp Glu Leu Asn Gln Lys Ser Ala Thr Leu
515                 520                 525                 530 gcg agt ata gat gct gag ctt cag aaa ctt aag gaa atg acc aac cac        2108
Ala Ser Ile Asp Ala Glu Leu Gln Lys Leu Lys Glu Met Thr Asn His
                535                 540                 545
```

```
cag aaa aaa cga gca gct gag atg atg gca tct tta cta aaa gac ctt         2156
Gln Lys Lys Arg Ala Ala Glu Met Met Ala Ser Leu Leu Lys Asp Leu
            550                 555                 560 gca gaa ata gga att gct gtg gga aat aat gat gta aag cag cct gag         2204
Ala Glu Ile Gly Ile Ala Val Gly Asn Asn Asp Val Lys Gln Pro Glu
                565                 570                 575 gga act ggc atg ata gat gaa gag ttc act gtt gca aga ctc tac att         2252
Gly Thr Gly Met Ile Asp Glu Glu Phe Thr Val Ala Arg Leu Tyr Ile
        580                 585                 590 agc aaa atg aag tca gaa gta aaa acc atg gtg aaa cgt tgc aag cag         2300
Ser Lys Met Lys Ser Glu Val Lys Thr Met Val Lys Arg Cys Lys Gln
595                 600                 605                 610 tta gaa agc aca caa act gag agc aac aaa aaa atg gaa gaa aat gaa         2348
Leu Glu Ser Thr Gln Thr Glu Ser Asn Lys Lys Met Glu Glu Asn Glu
            615                 620                 625 aag gag tta gca gca tgt cag ctt cgt atc tct caa cat gaa gcc aaa         2396
Lys Glu Leu Ala Ala Cys Gln Leu Arg Ile Ser Gln His Glu Ala Lys
                630                 635                 640 atc aag tca ttg act gaa tac ctt caa aat gtg gaa caa aag aaa aga         2444
Ile Lys Ser Leu Thr Glu Tyr Leu Gln Asn Val Glu Gln Lys Lys Arg
        645                 650                 655 cag ttg gag gaa tct gtc gat gcc ctc agt gaa gaa cta gtc cag ctt         2492
Gln Leu Glu Glu Ser Val Asp Ala Leu Ser Glu Glu Leu Val Gln Leu
660                 665                 670 cga gca caa gag aaa gtc cat gaa atg gaa aag gag cac tta aat aag         2540
Arg Ala Gln Glu Lys Val His Glu Met Glu Lys Glu His Leu Asn Lys
675                 680                 685                 690 gtt cag act gca aat gaa gtt aag caa gct gtt gaa cag cag atc cag         2588
Val Gln Thr Ala Asn Glu Val Lys Gln Ala Val Glu Gln Gln Ile Gln
            695                 700                 705 agc cat aga gaa act cat caa aaa cag atc agt agt ttg aga gat gaa         2636
Ser His Arg Glu Thr His Gln Lys Gln Ile Ser Ser Leu Arg Asp Glu
                710                 715                 720 gta gaa gca aaa gca aaa ctt att act gat ctt caa gac caa aac cag         2684
Val Glu Ala Lys Ala Lys Leu Ile Thr Asp Leu Gln Asp Gln Asn Gln
        725                 730                 735 aaa atg atg tta gag cag gaa cgt cta aga gta gaa cat gag aag ttg         2732
Lys Met Met Leu Glu Gln Glu Arg Leu Arg Val Glu His Glu Lys Leu
740                 745                 750 aaa gcc aca gat cag gaa aag agc aga aaa cta cat gaa ctt acg gtt         2780
Lys Ala Thr Asp Gln Glu Lys Ser Arg Lys Leu His Glu Leu Thr Val
755                 760                 765                 770 atg caa gat aga cga gaa caa gca aga caa gac ttg aag ggt ttg gaa         2828
Met Gln Asp Arg Arg Glu Gln Ala Arg Gln Asp Leu Lys Gly Leu Glu
            775                 780                 785 gag aca gtg gca aaa gaa ctt cag act tta cac aac ctg cgc aaa ctc         2876
Glu Thr Val Ala Lys Glu Leu Gln Thr Leu His Asn Leu Arg Lys Leu
                790                 795                 800 ttt gtt cag gac ctg gct aca aga gtt aaa aag agt gct gag att gat         2924
Phe Val Gln Asp Leu Ala Thr Arg Val Lys Lys Ser Ala Glu Ile Asp
        805                 810                 815 tct gat gac acc gga ggc agc gct gct cag aag caa aaa atc tcc ttt         2972
Ser Asp Asp Thr Gly Gly Ser Ala Ala Gln Lys Gln Lys Ile Ser Phe
820                 825                 830 ctt gaa aat aat ctt gaa cag ctc act aaa gtg cac aaa cag ttg gta         3020
Leu Glu Asn Asn Leu Glu Gln Leu Thr Lys Val His Lys Gln Leu Val
835                 840                 845                 850 cgt gat aat gca gat ctc cgc tgt gaa ctt cct aag ttg gaa aag cga         3068
Arg Asp Asn Ala Asp Leu Arg Cys Glu Leu Pro Lys Leu Glu Lys Arg
            855                 860                 865
```

```
ctt cga gct aca gct gag aga gtg aaa gct ttg gaa tca gca ctg aaa      3116
Leu Arg Ala Thr Ala Glu Arg Val Lys Ala Leu Glu Ser Ala Leu Lys
            870                 875                 880 gaa gct aaa gaa aat gca tct cgt gat cgc aaa cgc tat cag caa gaa      3164
Glu Ala Lys Glu Asn Ala Ser Arg Asp Arg Lys Arg Tyr Gln Gln Glu
        885                 890                 895 gta gat cgc ata aag gaa gca gtc agg tca aag aat atg gcc aga aga      3212
Val Asp Arg Ile Lys Glu Ala Val Arg Ser Lys Asn Met Ala Arg Arg
    900                 905                 910 ggg cat tct gca cag att gat gtg gcc gag gag gcg ggc tgc ccc ctg      3260
Gly His Ser Ala Gln Ile Asp Val Ala Glu Glu Ala Gly Cys Pro Leu
915                 920                 925                 930 tcc tgt gca gtc agc aag aga cgg ctg gag tgt gag gag tgt ggc ggc      3308
Ser Cys Ala Val Ser Lys Arg Arg Leu Glu Cys Glu Glu Cys Gly Gly
                935                 940                 945 ctg ggc tcc cca aca ggc agg tgt gag tgg agg caa gga gat ggc aaa      3356
Leu Gly Ser Pro Thr Gly Arg Cys Glu Trp Arg Gln Gly Asp Gly Lys
            950                 955                 960 ggg atc acc agg aac ttc tcc acc tgc tct ccc agc acc aag acc tgc      3404
Gly Ile Thr Arg Asn Phe Ser Thr Cys Ser Pro Ser Thr Lys Thr Cys
        965                 970                 975 ccc gac ggc cac tgc gat gtt gtg gag acc caa gac atc aac att tgc      3452
Pro Asp Gly His Cys Asp Val Val Glu Thr Gln Asp Ile Asn Ile Cys
    980                 985                 990 cct cag gac tgc ctc cgg ggc agc att gtt ggg gga cac gag cct           3497
Pro Gln Asp Cys Leu Arg Gly Ser Ile Val Gly Gly His Glu Pro
995                 1000                1005 ggg gag ccc cgg ggg att aaa gct ggc tat ggc acc tgc aac tgc          3542
Gly Glu Pro Arg Gly Ile Lys Ala Gly Tyr Gly Thr Cys Asn Cys
1010                1015                1020 ttc cct gag gag gag aag tgc ttc tgc gag ccc gaa gac atc cag          3587
Phe Pro Glu Glu Glu Lys Cys Phe Cys Glu Pro Glu Asp Ile Gln
1025                1030                1035 gat cca ctg tgc gac gag ctg tgc cgc acg gtg atc gca gcc gct          3632
Asp Pro Leu Cys Asp Glu Leu Cys Arg Thr Val Ile Ala Ala Ala
1040                1045                1050 gtc ctc ttc tcc ttc atc gtc tcg gtg ctg ctg tct gcc ttc tgc          3677
Val Leu Phe Ser Phe Ile Val Ser Val Leu Leu Ser Ala Phe Cys
1055                1060                1065 atc cac tgc tac cac aag ttt gcc cac aag cca ccc atc tcc tca          3722
Ile His Cys Tyr His Lys Phe Ala His Lys Pro Pro Ile Ser Ser
1070                1075                1080 gct gag atg acc ttc cgg agg ccc gcc cag gcc ttc ccg gtc agc          3767
Ala Glu Met Thr Phe Arg Arg Pro Ala Gln Ala Phe Pro Val Ser
1085                1090                1095 tac tcc tct tcc ggt gcc cgc cgg ccc tcg ctg gac tcc atg gag          3812
Tyr Ser Ser Ser Gly Ala Arg Arg Pro Ser Leu Asp Ser Met Glu
1100                1105                1110 aac cag gtc tcc gtg gat gcc ttc aag atc ctg gag gat cca aag          3857
Asn Gln Val Ser Val Asp Ala Phe Lys Ile Leu Glu Asp Pro Lys
1115                1120                1125 tgg gaa ttc cct cgg aag aac ttg gtt ctt gga aaa act cta gga          3902
Trp Glu Phe Pro Arg Lys Asn Leu Val Leu Gly Lys Thr Leu Gly
1130                1135                1140 gaa ggc gaa ttt gga aaa gtg gtc aag gca acg gcc ttc cat ctg          3947
Glu Gly Glu Phe Gly Lys Val Val Lys Ala Thr Ala Phe His Leu
1145                1150                1155 aaa ggc aga gca ggg tac acc acg gtg gcc gtg aag atg ctg aaa          3992
Lys Gly Arg Ala Gly Tyr Thr Thr Val Ala Val Lys Met Leu Lys
```

|  |  |  |  |  |  |  |  |  |  |  |
|---|---|---|---|---|---|---|---|---|---|---|
| 1160 | | | | 1165 | | | | 1170 | | |
| gag | aac | gcc | tcc | ccg | agt | gag | ctt | cga | gac | ctg | ctg | tca | gag | ttc | 4037 |
| Glu | Asn | Ala | Ser | Pro | Ser | Glu | Leu | Arg | Asp | Leu | Leu | Ser | Glu | Phe |
| 1175 | | | | 1180 | | | | 1185 | | |
| aac | gtc | ctg | aag | cag | gtc | aac | cac | cca | cat | gtc | atc | aaa | ttg | tat | 4082 |
| Asn | Val | Leu | Lys | Gln | Val | Asn | His | Pro | His | Val | Ile | Lys | Leu | Tyr |
| 1190 | | | | 1195 | | | | 1200 | | |
| ggg | gcc | tgc | agc | cag | gat | ggc | ccg | ctc | ctc | atc | gtg | gag | tac | 4127 |
| Gly | Ala | Cys | Ser | Gln | Asp | Gly | Pro | Leu | Leu | Ile | Val | Glu | Tyr |
| 1205 | | | | 1210 | | | | 1215 | | |
| gcc | aaa | tac | ggc | tcc | ctg | cgg | ggc | ttc | ctc | cgc | gag | agc | cgc | aaa | 4172 |
| Ala | Lys | Tyr | Gly | Ser | Leu | Arg | Gly | Phe | Leu | Arg | Glu | Ser | Arg | Lys |
| 1220 | | | | 1225 | | | | 1230 | | |
| gtg | ggg | cct | ggc | tac | ctg | ggc | agt | gga | ggc | agc | cgc | aac | tcc | agc | 4217 |
| Val | Gly | Pro | Gly | Tyr | Leu | Gly | Ser | Gly | Gly | Ser | Arg | Asn | Ser | Ser |
| 1235 | | | | 1240 | | | | 1245 | | |
| tcc | ctg | gac | cac | ccg | gat | gag | cgg | gcc | ctc | acc | atg | ggc | gac | ctc | 4262 |
| Ser | Leu | Asp | His | Pro | Asp | Glu | Arg | Ala | Leu | Thr | Met | Gly | Asp | Leu |
| 1250 | | | | 1255 | | | | 1260 | | |
| atc | tca | ttt | gcc | tgg | cag | atc | tca | cag | ggg | atg | cag | tat | ctg | gcc | 4307 |
| Ile | Ser | Phe | Ala | Trp | Gln | Ile | Ser | Gln | Gly | Met | Gln | Tyr | Leu | Ala |
| 1265 | | | | 1270 | | | | 1275 | | |
| gag | atg | aag | ctc | gtt | cat | cgg | gac | ttg | gca | gcc | aga | aac | atc | ctg | 4352 |
| Glu | Met | Lys | Leu | Val | His | Arg | Asp | Leu | Ala | Ala | Arg | Asn | Ile | Leu |
| 1280 | | | | 1285 | | | | 1290 | | |
| gta | gct | gag | ggg | cgg | aag | atg | aag | att | tcg | gat | ttc | ggc | ttg | tcc | 4397 |
| Val | Ala | Glu | Gly | Arg | Lys | Met | Lys | Ile | Ser | Asp | Phe | Gly | Leu | Ser |
| 1295 | | | | 1300 | | | | 1305 | | |
| cga | gat | gtt | tat | gaa | gag | gat | tcc | tac | gtg | aag | agg | agc | cag | ggt | 4442 |
| Arg | Asp | Val | Tyr | Glu | Glu | Asp | Ser | Tyr | Val | Lys | Arg | Ser | Gln | Gly |
| 1310 | | | | 1315 | | | | 1320 | | |
| cgg | att | cca | gtt | aaa | tgg | atg | gca | att | gaa | tcc | ctt | ttt | gat | cat | 4487 |
| Arg | Ile | Pro | Val | Lys | Trp | Met | Ala | Ile | Glu | Ser | Leu | Phe | Asp | His |
| 1325 | | | | 1330 | | | | 1335 | | |
| atc | tac | acc | acg | caa | agt | gat | gta | tgg | tct | ttt | ggt | gtc | ctg | ctg | 4532 |
| Ile | Tyr | Thr | Thr | Gln | Ser | Asp | Val | Trp | Ser | Phe | Gly | Val | Leu | Leu |
| 1340 | | | | 1345 | | | | 1350 | | |
| tgg | gag | atc | gtg | acc | cta | ggg | gga | aac | ccc | tat | cct | ggg | att | cct | 4577 |
| Trp | Glu | Ile | Val | Thr | Leu | Gly | Gly | Asn | Pro | Tyr | Pro | Gly | Ile | Pro |
| 1355 | | | | 1360 | | | | 1365 | | |
| cct | gag | cgg | ctc | ttc | aac | ctt | ctg | aag | acc | ggc | cac | cgg | atg | gag | 4622 |
| Pro | Glu | Arg | Leu | Phe | Asn | Leu | Leu | Lys | Thr | Gly | His | Arg | Met | Glu |
| 1370 | | | | 1375 | | | | 1380 | | |
| agg | cca | gac | aac | tgc | agc | gag | gag | atg | tac | cgc | ctg | atg | ctg | caa | 4667 |
| Arg | Pro | Asp | Asn | Cys | Ser | Glu | Glu | Met | Tyr | Arg | Leu | Met | Leu | Gln |
| 1385 | | | | 1390 | | | | 1395 | | |
| tgc | tgg | aag | cag | gag | ccg | gac | aaa | agg | ccg | gtg | ttt | gcg | gac | atc | 4712 |
| Cys | Trp | Lys | Gln | Glu | Pro | Asp | Lys | Arg | Pro | Val | Phe | Ala | Asp | Ile |
| 1400 | | | | 1405 | | | | 1410 | | |
| agc | aaa | gac | ctg | gag | aag | atg | atg | gtt | aag | agg | aga | gac | tac | ttg | 4757 |
| Ser | Lys | Asp | Leu | Glu | Lys | Met | Met | Val | Lys | Arg | Arg | Asp | Tyr | Leu |
| 1415 | | | | 1420 | | | | 1425 | | |
| gac | ctt | gcg | gcg | tcc | act | cca | tct | gac | tcc | ctg | att | tat | gac | gac | 4802 |
| Asp | Leu | Ala | Ala | Ser | Thr | Pro | Ser | Asp | Ser | Leu | Ile | Tyr | Asp | Asp |
| 1430 | | | | 1435 | | | | 1440 | | |
| ggc | ctc | tca | gag | gag | gag | aca | ccg | ctg | gtg | gac | tgt | aat | aat | gcc | 4847 |
| Gly | Leu | Ser | Glu | Glu | Glu | Thr | Pro | Leu | Val | Asp | Cys | Asn | Asn | Ala |
| 1445 | | | | 1450 | | | | 1455 | | |
| ccc | ctc | cct | cga | gcc | ctc | cct | tcc | aca | tgg | att | gaa | aac | aaa | ctc | 4892 |

```
Pro Leu Pro Arg Ala Leu Pro Ser Thr Trp Ile Glu Asn Lys Leu
1460            1465                1470 tat ggc atg tca gac ccg aac tgg cct gga gag agt cct gta cca    4937
Tyr Gly Met Ser Asp Pro Asn Trp Pro Gly Glu Ser Pro Val Pro
1475            1480                1485 ctc acg aga gct gat ggc act aac act ggg ttt cca aga tat cca    4982
Leu Thr Arg Ala Asp Gly Thr Asn Thr Gly Phe Pro Arg Tyr Pro
1490            1495                1500 aat gat agt gta tat gct aac tgg atg ctt tca ccc tca gcg gca    5027
Asn Asp Ser Val Tyr Ala Asn Trp Met Leu Ser Pro Ser Ala Ala
1505            1510                1515 aaa tta atg gac acg ttt gat agt taacattct tgtgaaagg            5071
Lys Leu Met Asp Thr Phe Asp Ser
1520            1525
```

| | | |
|---|---|---|
| taatggactc acaaggggaa gaaacatgct gagaatggaa agtctaccgg cccttctttt | 5131 |
| gtgaacgtca cattggccga gccgtgttca gttcccaggt ggcagactcg ttttttggtag | 5191 |
| tttgttttaa cttccaaggt ggttttactt ctgatagccg gtgattttcc ctcctagcag | 5251 |
| acatgccaca ccgggtaaga gctctgagtc ttagtggtta agcattcctt tctcttcagt | 5311 |
| gcccagcagc acccagtgtt ggtctgtgtc catcagtgac caccaacatt ctgtgttcac | 5371 |
| atgtgtgggt ccaacactta ctacctggtg tatgaaattg gacctgaact gttggatttt | 5431 |
| tctagttgcc gccaaacaag gcaaaaaaat ttaaacatga agcacacaca caaaaaggc | 5491 |
| agtaggaaaa atgctggccc tgatgacctg tccttattca gaatgagaga ctgcgggggg | 5551 |
| ggcctggggg tagtgtcaat gcccctccag ggctggaggg gaagagggggc cccgaggatg | 5611 |
| ggcctgggct cagcattcga gatcttgaga atgattttt tttaatcatg caacctttcc | 5671 |
| ttaggaagac atttggtttt catcatgatt aagatgattc ctagatttag cacaatggag | 5731 |
| agattccatg ccatctttac tatgtggatg gtggtatcag ggaagagggc tcacaagaca | 5791 |
| catttgtccc ccgggcccac cacatcatcc tcacgtgttc ggtactgagc agccactacc | 5851 |
| cctgatgaga acagtatgaa gaaagggggc tgttggagtc ccagaattgc tgacagcaga | 5911 |
| ggctttgctg ctgtgaatcc cacctgccac cagcctgcag cacacccac agccaagtag | 5971 |
| aggcgaaagc agtggctcat cctacctgtt aggagcaggt agggcttgta ctcactttaa | 6031 |
| tttgaatctt atcaacttac tcataaaggg acaggctagc tagctgtgtt agaagtagca | 6091 |
| atgacaatga ccaaggactg ctacacctct gattacaatt ctgatgtgaa aaagatggtg | 6151 |
| tttggctctt atagagcctg tgtgaaaggc ccatggatca gctcttcctg tgtttgtaat | 6211 |
| ttaatgctgc tacaagatgt ttctgtttct tagattctga ccatgactca taagcttctt | 6271 |
| gtcattcttc attgcttgtt tgtggtcaca gatgcacaac actcctccag tcttgtgggg | 6331 |
| gcagcttttg ggaagtctca gcagctcttc tggctgtgtt gtcagcactg taacttcgca | 6391 |
| gaaaagagtc ggattaccaa aacactgcct gctcttcaga cttaaagcac tgataggact | 6451 |
| taaaatagtc tcattcaaat actgtatttt atataggcat ttcacaaaaa cagcaaaatt | 6511 |
| gtggcatttt gtgaggccaa ggcttggatg cgtgtgtaat agagccttgt ggtgtgtgcg | 6571 |
| cacacaccca gagggagagt ttgaaaaatg cttattggac acgtaacctg gctctaattt | 6631 |
| gggctgtttt tcagatacac tgtgataagt tcttttacaa atatctatag acatggtaaa | 6691 |
| cttttggttt tcagatatgc ttaatgatag tcttactaaa tgcagaaata agaataaact | 6751 |
| ttctcaaatt attaaaaatg cctacacagt aagtgtgaat tgctgcaaca ggtttgttct | 6811 |
| caggagggta agaactccag gtctaaacag ctgacccagt gatggggaat ttatccttga | 6871 |

```
ccaatttatc cttgaccaat aacctaattg tctattcctg agttataaaa gtccccatcc      6931
ttattagctc tactggaatt ttcatacacg taaatgcaga agttactaag tattaagtat      6991
tactgagtat taagtagtaa tctgtcagtt attaaaattt gtaaaatcta tttatgaaag      7051
gtcattaaac cagatcatgt tccttttttt gtaatcaagg tgactaagaa aatcagttgt      7111
gtaaataaaa tcatgtatca taaaaaaaaa aaaaaaa                              7148
```

<210> SEQ ID NO 12
<211> LENGTH: 1527
<212> TYPE: PRT
<213> ORGANISM: Homo sapiens

<400> SEQUENCE: 12

```
Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
```

```
                    325                 330                 335
Ala Glu Gln Trp Lys Lys Tyr Glu Lys Glu Lys Asn Lys
                340                 345                 350
Ile Leu Arg Asn Thr Ile Gln Trp Leu Glu Asn Glu Leu Asn Arg Trp
                355                 360                 365
Arg Asn Gly Glu Thr Val Pro Ile Asp Glu Gln Phe Asp Lys Glu Lys
                370                 375                 380
Ala Asn Leu Glu Ala Phe Thr Val Asp Lys Asp Ile Thr Leu Thr Asn
385                 390                 395                 400
Asp Lys Pro Ala Thr Ala Ile Gly Val Ile Gly Asn Phe Thr Asp Ala
                405                 410                 415
Glu Arg Arg Lys Cys Glu Glu Ile Ala Lys Leu Tyr Lys Gln Leu
                420                 425                 430
Asp Asp Lys Asp Glu Glu Ile Asn Gln Gln Ser Gln Leu Val Glu Lys
                435                 440                 445
Leu Lys Thr Gln Met Leu Asp Gln Glu Glu Leu Leu Ala Ser Thr Arg
        450                 455                 460
Arg Asp Gln Asp Asn Met Gln Ala Glu Leu Asn Arg Leu Gln Ala Glu
465                 470                 475                 480
Asn Asp Ala Ser Lys Glu Val Lys Glu Val Leu Gln Ala Leu Glu
                485                 490                 495
Glu Leu Ala Val Asn Tyr Asp Gln Lys Ser Gln Glu Val Glu Asp Lys
                500                 505                 510
Thr Lys Glu Tyr Glu Leu Leu Ser Asp Glu Leu Asn Gln Lys Ser Ala
            515                 520                 525
Thr Leu Ala Ser Ile Asp Ala Glu Leu Gln Lys Leu Lys Glu Met Thr
        530                 535                 540
Asn His Gln Lys Lys Arg Ala Ala Glu Met Met Ala Ser Leu Leu Lys
545                 550                 555                 560
Asp Leu Ala Glu Ile Gly Ile Ala Val Gly Asn Asn Asp Val Lys Gln
                565                 570                 575
Pro Glu Gly Thr Gly Met Ile Asp Glu Glu Phe Thr Val Ala Arg Leu
                580                 585                 590
Tyr Ile Ser Lys Met Lys Ser Glu Val Lys Thr Met Val Lys Arg Cys
            595                 600                 605
Lys Gln Leu Glu Ser Thr Gln Thr Glu Ser Asn Lys Lys Met Glu Glu
        610                 615                 620
Asn Glu Lys Glu Leu Ala Ala Cys Gln Leu Arg Ile Ser Gln His Glu
625                 630                 635                 640
Ala Lys Ile Lys Ser Leu Thr Glu Tyr Leu Gln Asn Val Glu Gln Lys
                645                 650                 655
Lys Arg Gln Leu Glu Glu Ser Val Asp Ala Leu Ser Glu Glu Leu Val
                660                 665                 670
Gln Leu Arg Ala Gln Glu Lys Val His Glu Met Glu Lys Glu His Leu
            675                 680                 685
Asn Lys Val Gln Thr Ala Asn Glu Val Lys Gln Ala Val Glu Gln Gln
        690                 695                 700
Ile Gln Ser His Arg Glu Thr His Gln Lys Gln Ile Ser Ser Leu Arg
705                 710                 715                 720
Asp Glu Val Glu Ala Lys Ala Lys Leu Ile Thr Asp Leu Gln Asp Gln
                725                 730                 735
Asn Gln Lys Met Met Leu Glu Gln Glu Arg Leu Arg Val Glu His Glu
                740                 745                 750
```

-continued

Lys Leu Lys Ala Thr Asp Gln Glu Lys Ser Arg Lys Leu His Glu Leu
        755                 760                 765

Thr Val Met Gln Asp Arg Arg Glu Gln Ala Arg Gln Asp Leu Lys Gly
770                 775                 780

Leu Glu Glu Thr Val Ala Lys Glu Leu Gln Thr Leu His Asn Leu Arg
785                 790                 795                 800

Lys Leu Phe Val Gln Asp Leu Ala Thr Arg Val Lys Lys Ser Ala Glu
                805                 810                 815

Ile Asp Ser Asp Asp Thr Gly Gly Ser Ala Ala Gln Lys Gln Lys Ile
            820                 825                 830

Ser Phe Leu Glu Asn Asn Leu Glu Gln Leu Thr Lys Val His Lys Gln
        835                 840                 845

Leu Val Arg Asp Asn Ala Asp Leu Arg Cys Glu Leu Pro Lys Leu Glu
    850                 855                 860

Lys Arg Leu Arg Ala Thr Ala Glu Arg Val Lys Ala Leu Glu Ser Ala
865                 870                 875                 880

Leu Lys Glu Ala Lys Glu Asn Ala Ser Arg Asp Arg Lys Arg Tyr Gln
                885                 890                 895

Gln Glu Val Asp Arg Ile Lys Glu Ala Val Arg Ser Lys Asn Met Ala
            900                 905                 910

Arg Arg Gly His Ser Ala Gln Ile Asp Val Ala Glu Glu Ala Gly Cys
        915                 920                 925

Pro Leu Ser Cys Ala Val Ser Lys Arg Arg Leu Glu Cys Glu Glu Cys
    930                 935                 940

Gly Gly Leu Gly Ser Pro Thr Gly Arg Cys Glu Trp Arg Gln Gly Asp
945                 950                 955                 960

Gly Lys Gly Ile Thr Arg Asn Phe Ser Thr Cys Ser Pro Ser Thr Lys
                965                 970                 975

Thr Cys Pro Asp Gly His Cys Asp Val Val Glu Thr Gln Asp Ile Asn
            980                 985                 990

Ile Cys Pro Gln Asp Cys Leu Arg Gly Ser Ile Val Gly Gly His Glu
        995                 1000                1005

Pro Gly Glu Pro Arg Gly Ile Lys Ala Gly Tyr Gly Thr Cys Asn
    1010                1015                1020

Cys Phe Pro Glu Glu Glu Lys Cys Phe Cys Glu Pro Glu Asp Ile
    1025                1030                1035

Gln Asp Pro Leu Cys Asp Glu Leu Cys Arg Thr Val Ile Ala Ala
    1040                1045                1050

Ala Val Leu Phe Ser Phe Ile Val Ser Val Leu Leu Ser Ala Phe
    1055                1060                1065

Cys Ile His Cys Tyr His Lys Phe Ala His Lys Pro Pro Ile Ser
    1070                1075                1080

Ser Ala Glu Met Thr Phe Arg Pro Ala Gln Ala Phe Pro Val
    1085                1090                1095

Ser Tyr Ser Ser Ser Gly Ala Arg Arg Pro Ser Leu Asp Ser Met
    1100                1105                1110

Glu Asn Gln Val Ser Val Asp Ala Phe Lys Ile Leu Glu Asp Pro
    1115                1120                1125

Lys Trp Glu Phe Pro Arg Lys Asn Leu Val Leu Gly Lys Thr Leu
    1130                1135                1140

Gly Glu Gly Glu Phe Gly Lys Val Val Lys Ala Thr Ala Phe His
    1145                1150                1155

Leu Lys Gly Arg Ala Gly Tyr Thr Thr Val Ala Val Lys Met Leu
1160                1165                1170

Lys Glu Asn Ala Ser Pro Ser Glu Leu Arg Asp Leu Leu Ser Glu
1175                1180                1185

Phe Asn Val Leu Lys Gln Val Asn His Pro His Val Ile Lys Leu
1190                1195                1200

Tyr Gly Ala Cys Ser Gln Asp Gly Pro Leu Leu Leu Ile Val Glu
1205                1210                1215

Tyr Ala Lys Tyr Gly Ser Leu Arg Gly Phe Leu Arg Glu Ser Arg
1220                1225                1230

Lys Val Gly Pro Gly Tyr Leu Gly Ser Gly Gly Ser Arg Asn Ser
1235                1240                1245

Ser Ser Leu Asp His Pro Asp Glu Arg Ala Leu Thr Met Gly Asp
1250                1255                1260

Leu Ile Ser Phe Ala Trp Gln Ile Ser Gln Gly Met Gln Tyr Leu
1265                1270                1275

Ala Glu Met Lys Leu Val His Arg Asp Leu Ala Ala Arg Asn Ile
1280                1285                1290

Leu Val Ala Glu Gly Arg Lys Met Lys Ile Ser Asp Phe Gly Leu
1295                1300                1305

Ser Arg Asp Val Tyr Glu Glu Asp Ser Tyr Val Lys Arg Ser Gln
1310                1315                1320

Gly Arg Ile Pro Val Lys Trp Met Ala Ile Glu Ser Leu Phe Asp
1325                1330                1335

His Ile Tyr Thr Thr Gln Ser Asp Val Trp Ser Phe Gly Val Leu
1340                1345                1350

Leu Trp Glu Ile Val Thr Leu Gly Gly Asn Pro Tyr Pro Gly Ile
1355                1360                1365

Pro Pro Glu Arg Leu Phe Asn Leu Leu Lys Thr Gly His Arg Met
1370                1375                1380

Glu Arg Pro Asp Asn Cys Ser Glu Glu Met Tyr Arg Leu Met Leu
1385                1390                1395

Gln Cys Trp Lys Gln Glu Pro Asp Lys Arg Pro Val Phe Ala Asp
1400                1405                1410

Ile Ser Lys Asp Leu Glu Lys Met Met Val Lys Arg Arg Asp Tyr
1415                1420                1425

Leu Asp Leu Ala Ala Ser Thr Pro Ser Asp Ser Leu Ile Tyr Asp
1430                1435                1440

Asp Gly Leu Ser Glu Glu Glu Thr Pro Leu Val Asp Cys Asn Asn
1445                1450                1455

Ala Pro Leu Pro Arg Ala Leu Pro Ser Thr Trp Ile Glu Asn Lys
1460                1465                1470

Leu Tyr Gly Met Ser Asp Pro Asn Trp Pro Gly Glu Ser Pro Val
1475                1480                1485

Pro Leu Thr Arg Ala Asp Gly Thr Asn Thr Gly Phe Pro Arg Tyr
1490                1495                1500

Pro Asn Asp Ser Val Tyr Ala Asn Trp Met Leu Ser Pro Ser Ala
1505                1510                1515

Ala Lys Leu Met Asp Thr Phe Asp Ser
1520                1525

<210> SEQ ID NO 13
<211> LENGTH: 20
<212> TYPE: DNA

```
<213> ORGANISM: Artificial Sequence
<220> FEATURE:
<223> OTHER INFORMATION: Artificially synthesized primer sequence

<400> SEQUENCE: 13
aggaaatgac caaccaccag                                            20

<210> SEQ ID NO 14
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 14
tccaaattcg ccttctccta                                            20

<210> SEQ ID NO 15
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 15
ccataagtga aatgattgga ac                                         22

<210> SEQ ID NO 16
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 16
gatttgtatg ttgcagtagc tg                                         22

<210> SEQ ID NO 17
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 17
ggagttagca gcatgtcagc                                            20

<210> SEQ ID NO 18
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 18
gctcactaaa gtgcacaaac ag                                         22

<210> SEQ ID NO 19
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 19
gaagagggca ttctgcacag                                            20
```

<210> SEQ ID NO 20
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 20
ggaggctcca ggatactcgg                                           20

<210> SEQ ID NO 21
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 21
cctcctcggc cacatctg                                             18

<210> SEQ ID NO 22
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 22
agagtgctga gattgattct g                                         21

<210> SEQ ID NO 23
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 23
cccgagtagc taggattaca                                           20

<210> SEQ ID NO 24
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 24
atgacaggtg tggtcacagc                                           20

<210> SEQ ID NO 25
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 25
tatccacaca ttgggcccac                                           20

<210> SEQ ID NO 26
<211> LENGTH: 20
<212> TYPE: DNA
<213> ORGANISM: Artificial Sequence
<220> FEATURE:

<223> OTHER INFORMATION: Artificially synthesized primer sequence

<400> SEQUENCE: 26
atggcagctg tgtcagcatg                                                    20

<210> SEQ ID NO 27
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 27
attccctcgg aagaacttgg                                                    20

<210> SEQ ID NO 28
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 28
gatgacatgt gggtggttga                                                    20